United States Patent [19]

Michnick et al.

[11] Patent Number: 5,801,181
[45] Date of Patent: Sep. 1, 1998

[54] AMINO ALCOHOL SUBSTITUTED CYCLIC COMPOUNDS

[75] Inventors: John Michnick, Seattle; Gail E. Underiner, Brier; J. Peter Klein, Vashon Island; Glenn C. Rice, Seattle, all of Wash.

[73] Assignee: Cell Therapeutics, Inc., Seattle, Wash.

[21] Appl. No.: 474,820

[22] Filed: Jun. 7, 1995

Related U.S. Application Data

[60] Division of Ser. No. 152,650, Nov. 12, 1993, abandoned, which is a continuation-in-part of Ser. No. 40,820, Mar. 31, 1993.

[51] Int. Cl.$^6$ .......................... A01N 43/00; A01N 43/90; A01N 43/58; A01N 43/42
[52] U.S. Cl. .......................... 514/263; 514/183; 514/249; 514/259; 514/274; 514/309; 514/315; 514/418; 514/425; 514/617; 514/619; 514/626; 514/668; 514/669
[58] Field of Search .......................... 514/263, 249, 514/259, 265, 274, 309, 315, 418, 425, 617, 619, 626, 668, 669

[56] References Cited

U.S. PATENT DOCUMENTS

| | | | |
|---|---|---|---|
| 3,422,107 | 1/1969 | Mohler et al. | 544/271 |
| 3,737,433 | 6/1973 | Mohler et al. | 544/271 |
| 4,515,795 | 5/1985 | Hinze et al. | 514/263 |
| 4,576,947 | 3/1986 | Hinze et al. | 514/263 |
| 4,636,507 | 1/1987 | Kreutzer et al. | 514/263 |
| 4,668,786 | 5/1987 | Thiele et al. | 54/267 |
| 4,833,146 | 5/1989 | Gebert et al. | 514/263 |
| 4,965,271 | 10/1990 | Mandell et al. | 514/263 |
| 5,039,666 | 8/1991 | Novick et al. | 514/37 |
| 5,096,906 | 3/1992 | Mandell et al. | 514/263 |

FOREIGN PATENT DOCUMENTS

| | | |
|---|---|---|
| 266161 | 3/1982 | Austria . |
| 113102 | 7/1984 | European Pat. Off. . |
| 132366 | 1/1985 | European Pat. Off. . |
| 335723 | 10/1989 | European Pat. Off. . |
| 2000943 | 9/1969 | France . |
| 2659241 | 7/1978 | Germany . |
| 58-96087 | 6/1983 | Japan . |
| 256428 | 2/1990 | Japan . |
| 1356789 | 6/1974 | United Kingdom . |
| 2096606 | 10/1982 | United Kingdom . |

OTHER PUBLICATIONS

Bianco et al., *Blood*, 76:Supplement 1 (522), p. 133a, "Pentoxifylline (PTX) and GM–CSF Decrease Tumor Necrosis Factor–ALPHA (TNF–α) Levels in Patients Undergoing Allogeneic Bone Marrow Transplantation (BMT)," 1991.
Davis et al., *Applied Environment Microbial.*, 48:2, pp. 327–331, "Microbial Models of Mammalian Metabolism: Microbial Reduction and Oxidation of Pentoxifylline," Aug. 1984.

Fuhrer et al., *J. Med. Chem.*, vol. 27, pp. 831–836, "β–Adrenergic Blocking Agents: Substituted Phenylalkanolamines. Effect of Side–Chain Length on β–Blocking Potency in Vitro", 1984.
Bariana et al., *Chimie Thérapeutique*, No. 2, pp. 101–104, "Xanthine Derivatives as Coronary Vasodilators", Mar.–Apr. 1971.

(List continued on next page.)

*Primary Examiner*—José G. Dees
*Assistant Examiner*—Alton Pryor
*Attorney, Agent, or Firm*—McDermott Will & Emery

[57] ABSTRACT

Therapeutic compounds have the formula:

(X)j—(core moiety),

J being an integer from one to three, the core moiety having at least one, five- to seven-membered ring and X being a racemic mixture, R or S enantiomer, slovate, hydrate, or salt of:

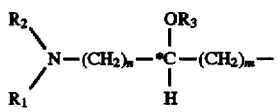

*C is a chiral carbon atom, n is an integer from one to four (preferably from one to three), one or more carbon atoms of $(CH_2)_n$ may be substituted by a keto or hydroxy group, and m is an integer from one to fourteen. Independently, $R_1$ and $R_2$ may be a hydrogen, a straight or branched chain alkane or alkene of up to twelve carbon atoms in length, or —$(CH_2)_w R_5$, w being an integer from two to fourteen and $R_5$ being a mono-, di- or tri-substituted or unsubstituted aryl group, substituents on $R_5$ being hydroxy, chloro, fluoro, bromo, or $C_{1-6}$ alkoxy. Or jointly, $R_1$ and $R_2$ form a substituted or unsubstituted, saturated or unsaturated heterocyclic group having from four to eight carbon atoms, N being a hetero atom. $R_3$ is a hydrogen or $C_{1-3}$. Or, therapeutic compounds may also have the formula:

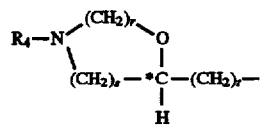

$R_4$ is a hydrogen, a straight or branched chain alkane or alkene of up to eight carbon atoms in length, —$(CH_2)_w R_5$, w being an integer from two to fourteen and $R_5$ being a mono-, di- or tri-substituted or unsubstituted aryl group, substituents on $R_5$ being hydroxy, chloro, fluoro, bromo, or $C_{1-6}$ alkoxy, or a substituted or unsubstituted, saturated or unsaturated heterocyclic group having from four to eight carbon atoms, N being a hetero atom. r and s are independently integers from one to four, the sum (r+s) not being greater than five. t is an integer from one to fourteen and one or more carbon atoms of $(CH_2)_r$ or $(CH_2)_s$ may be substituted by a keto or hydroxy group.

45 Claims, 38 Drawing Sheets

OTHER PUBLICATIONS

*Chemical Abstracts*, vol. 57: col. 13140h–13141b, 1962.
*Chemical Abstracts*, vol. 58: col. 10211c–10214g, 1963.
*Chemical Abstracts*, vol. 60: col. 4140g, 1964.
*Chemical Abstracts*, vol. 70: No. 29155k, p. 350, 1969.
*Chemical Abstracts*, vol. 71: No. 30615n, p. 314, 1969.
*Chemical Abstracts*, vol. 75: No. 129988f, p. 313, 1971.
*Chemical Abstracts*, vol. 99: No. 105059y, p. 568, 1983.

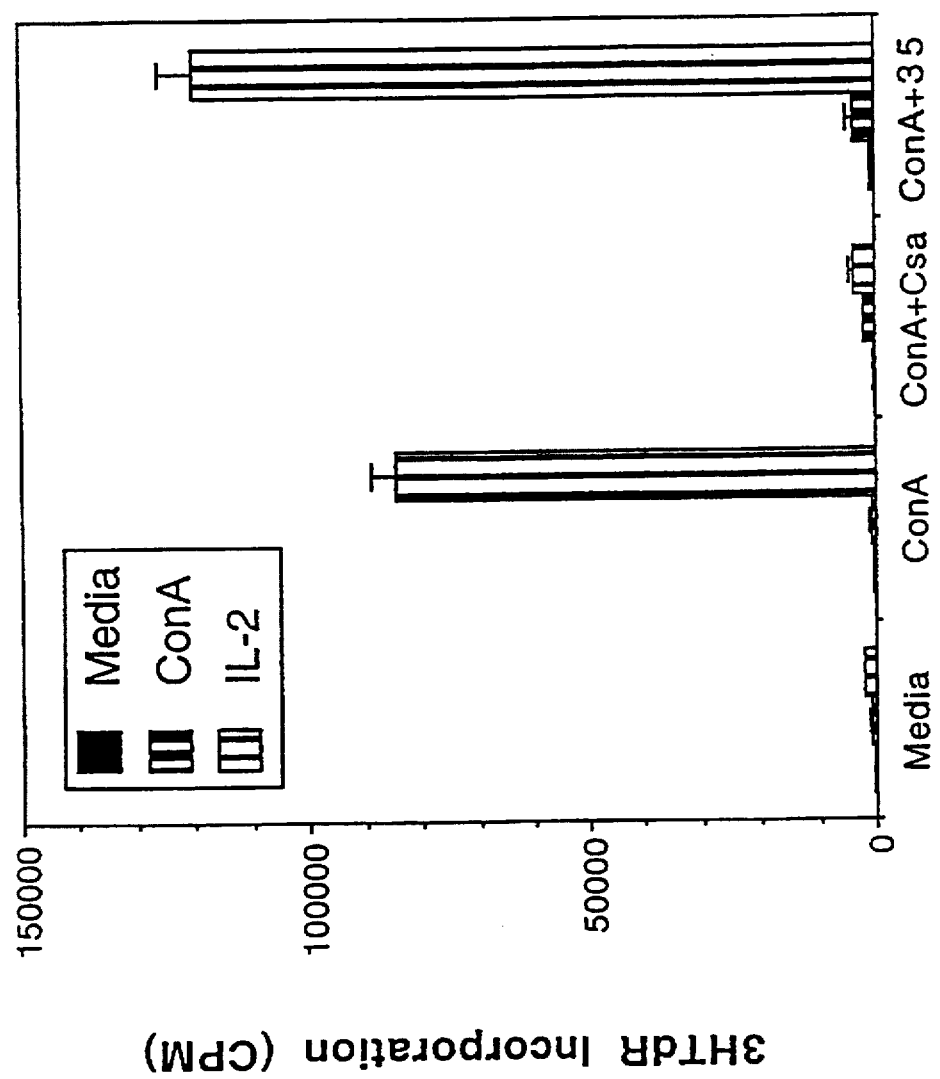

AMINO ALCOHOL SUBSTITUTED CYCLIC COMPOUNDS

CROSS REFERENCE TO RELATED APPLICATION

This is a Division of U.S. application Ser. No. 08/152,650, filed Nov. 12, 1993 now abandoned which is a Continuation-in-Part Application of U.S. application Ser. No. 08/040,820 filed Mar. 31, 1993.

TECHNICAL FIELD OF THE INVENTION

The invention provides a group of amino alcohol substituted cyclic compounds that are effective agents to inhibit specific cellular signaling events often induced by [noxious] or inflammatory stimuli, or to be directly or indirectly (immune stimulation) antimicrobial to yeast or fungal infections. More specifically, the inventive compounds have at least one amino alcohol functional group on a side chain attached to a cyclic core. The inventive compounds are useful antagonists to control intracellular levels of specific sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX and disclosed in U.S. Pat. Nos. 3,422,107 and 3,737,433, is a xanthine derivative which has seen widespread medical use for increasing blood flow. Metabolites of PTX were summarized in Davis et al., *Applied Environment Microbiol.* (1984) 48:327. One such metabolite, 1-(5-hydroxyhexyl)-3,7-dimethylxanthine, designated M1 and disclosed in U.S. Pat. Nos. 4,515,795 and 4,576,947, increases cerebral blood flow. In addition, U.S. Pat. Nos. 4,833,146 and 5,039,666 disclose use of tertiary alcohol analogs of xanthine for enhancing cerebral blood flow.

U.S. Pat. No. 4,636,507 discloses that PTX and M1 stimulate chemotaxis in polymorphonuclear leukocytes in response to a chemotaxis stimulator. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in bone marrow transplant-related complications accompanied reduction in assayable levels of TNF. However, in normal volunteers, TNF levels were higher among PTX recipients. Therefore, elevated levels of TNF are not the primary cause of such complications.

Therefore, effective therapeutic compounds that are safe and effective for human or animal administration and that can maintain cellular homeostasis in the face of a variety of inflammatory stimuli are needed. The invention is a result of research conducted in looking for such compounds.

SUMMARY OF THE INVENTION

We have found inventive compounds useful in a large variety of therapeutic indications for modulating disease by intracellular signaling through one or two specific intracellular signaling pathways. In addition, the inventive compounds and compositions are suitable for normal routes of therapeutic administration (e.g., parenteral, oral, topical, etc.) for providing effective dosages.

The invention provides for a class of amino alcohol substituted compounds, preferably heterocyclic compounds. The inventive compounds and inventive pharmaceutical compositions thereof have the formula:

(X)j—(core moiety), wherein j is an integer from one to three, the core moiety comprises at least one, five- to seven-membered ring and X is a racemic mixture, R or S enantiomer, solvate, hydrate, or salt of:

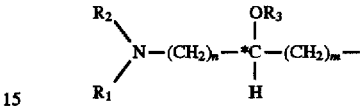

wherein *C is a chiral carbon atom; n is an integer from one to four (preferably from one to three); one or more carbon atoms of $(CH_2)_n$ may be substituted by a keto or hydroxy group; m is an integer from one to fourteen (preferably one to eight or ten to fourteen); independently, $R_1$ and $R_2$ are hydrogen, a straight or branched chain alkane or alkene of up to twelve carbon atoms in length, or $—(CH_2)_wR_5$, w being an integer from two to fourteen and $R_5$ being a mono-, di- or tri-substituted or unsubstituted aryl group, substituents on $R_5$ being hydroxy, chloro, fluoro, bromo, or $C_{1-6}$ alkoxy; or jointly, $R_1$ and $R_2$ form a substituted or unsubstituted, saturated or unsaturated heterocyclic group having from four to eight carbon atoms, N being a hetero atom; and $R_3$ is hydrogen or $C_{1-3}$; or

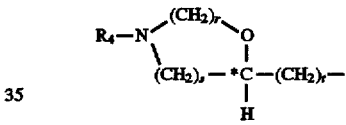

wherein $R_4$ is a hydrogen, a straight or branched chain alkane or alkene of up to eight carbon atoms in length, $—(CH_2)_wR_5$, w being an integer from two to fourteen and $R_5$ being a mono-, di- or tri-substituted or unsubstituted aryl group, substituents on $R_5$ being hydroxy, chloro, fluoro, bromo, or $C_{1-6}$ alkoxy, or a substituted or unsubstituted, saturated or unsaturated heterocyclic group having from four to eight carbon atoms, r and s are independently integers from one to four; the sum (r+s) is not greater than five; t is an integer from one to fourteen; and one or more carbon atoms of $(CH_2)_r$ or $(CH_2)_t$ may be substituted by a keto or hydroxy group.

The core moiety is at least one five- to seven-membered ring, preferably having from one to three, five- to six-membered ring structures in a predominantly planar configuration. Preferably, the amino alcohol substituent (X) is bonded to a ring nitrogen if one exists. For example, the core moiety may be selected from the group consisting of substituted or unsubstituted: barbituric acid; benzamide; benzene; biphenyl; cyclohexanedione; cyclopentanedione; delta-lactam; flutarimide; glutarimide; homophthalimide; imidazole amide; isocarbostyrile; lumazine; napthlalene; pteridine; pthalimide; piperidine; pyridine; pyrimidine; pyrrole amide; quinazolinedione; quinazolinone; quinolone; recorsinol; stilbene; succinimide; theobromine; thymine; triazine; tricyclododecane; uracil or xanthine.

Preferred cores include substituted or unsubstituted glutarimide, methylthymine, methyluracil, thymine, theobromine, uracil and xanthine, most preferably halogen-substituted xanthine. Exemplary preferred cores include, but are not limited to: 1,3-cyclohexanedione, 1,3-cyclopentanedione; 1,3-dihydroxynaphthalene; 1-methyllumazine; methylbarbituric acid; 3,3- dimethylflutarimide; 2-hydroxypyridine; methyldihydroxypyrazolopyrimidine (preferably, 1,3-dimethyldihydroxypyrazolo[4,3-d]pyrimidine); methylpyrrolopyrinmidine (preferably, 1-methylpyrrolo [2,3-d]pyrimidine); 2-pyrrole amides; 3-pyrrole amides; 1,2,3,4-tetrahydroisoquinolone; 1-methyl-2,4(1H,3H)-quinazolinedione (1-methylbenzoyleneurea); quinazolin-4(3H)-one; alkyl-substituted ($C_{1-6}$)thymine; methylthymine; alkyl-substituted ($C_{1-6}$) 6) uracil; 6-aminouracil; 1-methyl-5,6-dihydrouracil; 1-methyluracil; 5- and/or 6-position substituted uracils; 1,7-dimethylxanthine, 3,7-dimethylxanthine; 3-methylxanthine; 3-methyl-7-methylpivaloylxanthine; 8-amino-3-methylxanthine; and 7-methylhypoxanthine.

Preferably, X is bonded to a nitrogen of the core moiety, most preferably the core moiety, is xanthine and X is bonded to an $N_1$ xanthine nitrogen and $N_3$ and $N_7$ xanthine nitrogens are independently substituted by a member selected from the group consisting of hydrogen, methyl, fluoro, chloro and amino.

The invention provides a pharmaceutical composition comprising an inventive compound and a pharmaceutically acceptable excipient. The pharmaceutical composition may be formulated for oral, parenteral or topical administration to a patient.

The invention includes a method for treating an individual having a variety of diseases. The disease is characterized by or can be treated by inhibiting an immune response or a cellular response to external or in situ primary stimuli, the cellular response being mediated through a specific phospholipid-based second messenger acting adjacent to a cell membrane inner leaflet. The second messenger pathway is activated in response to various noxious or proliferative stimuli characteristic of a variety of disease states. Biochemistry of this second messenger pathway is described herein. More specifically, the invention includes methods for treating or preventing clinical symptoms of various disease states or reducing toxicity of other treatments by inhibiting cellular signaling through a second messenger pathway involving signaling through phosphatidic acid and through glycan phosphatidylinostinol (Gly PI).

Gly PI consists of a phosphatidylinositol-1-phosphate (PIP) bound through the carbon 6-hydroxyl to a glucosamine residue, which in turn is bound, usually to 2–5 other glycan residues (1→4 type, linear bonds) containing an additional one to three phosphoethanolamine moieties, the last of which may be bound to an external protein such as Thy-1. Evidence suggests a broad variety of structural variation in the sn-1 and sn-2 positions of the glycerol/lipid moiety of the phosphatidylinositol, as well as fatty acyl addition to the 2-OH group of the inositol. Several functional parameters of structure have been observed, the most remarkable of which point to a minimum presence of at least one myristoyl sidechain in Gly-PI molecules, the presence of both alkyl (ether) and acyl chains in the sn-1 position, and the presence of palmitate (C16:0) in the 2-OH position of the inositol in protein-binding Gly-PI. Thomas et al., *Biochemistry* (1991): 29:5413–5422.

Recent research has demonstrated that 2-OH-acylation of the inositol moiety conveys resistance to hydrolysis with Gly PI-directed phospholipase C ($P_i$G-PLC, a phosphodiesterase which hydrolyzes Gly PI to glycan inositol phosphate and diacylglycerol) but not to Gly PI-directed phospholipase D ($P_i$G-PLD, a phosphodiesterase which hydrolyzes Gly PI to glycan inositol+phosphatidic acid).

Research has identified two functions of Gly-PI: 1) external protein binding, the purpose of which may be simple binding to the cell membrane or placement of conformational constraints on the structure of externally bound membrane proteins (e.g., so that a particular portion of the molecule faces an extracellular environment); and 2) signal transduction, including part of the intracellular signal sent by insulin and a detectable portion of the signal transduced by Interleukin-2 (IL-2). We have found that signal transducing Gly-PI in B lymphocytes is hydrolyzed following anti-mu crosslinking, and then resynthesized rapidly. In these systems, two Gly-PI species are synthesized: a) Gly $PI_1$, containing 1-myristoyl 2-palmitoyl, 1-o-tetradecanyl (myristyl) 2-palmitoyl and 1-myristyl 2-myristyl phosphatidylinositol; and b) Gly $PI_2$, containing 1-myristoyl 2-oleoyl and 1-o-myristyl 2-linoleoyl phosphatidylinositol. Fraction (a) above contains a 1:1 mole content of C22 or C20 acyl groups attached to the inositol phosphate. The Gly-$PI_1$ fraction, identified by glucosamine labeling followed by mass spectrometry, exhibits a characteristic tripartite peak (glycan-inositol: 2-OH-acyl: phosphatidic acid moieties) and is uniformly inositol 2-OH acylated. Therefore, fraction (a) conveys resistance to $P_i$G-PLC but not to $P_i$G-PLD, suggesting that the observed fraction, when hydrolyzed, will generate 1-myristyl and 1-o-myristyl phosphatidic acid species, subsequently observed.

Thus, inventive compounds, useful in treating diseases and reducing toxicity of other disease treatments, would affect cellular signaling through a second messenger pathway by interacting with binding and/or signaling functions of Gly PI.

A disease state or treatment-induced toxicity are selected from the group consisting of: tumor progression involving tumor stimulation of blood supply (angiogenesis) by production of fibroblast growth factor (FGF), vascular endothelial growth factor (VEGF) or platelet-derived growth factor (PDGF); tumor invasion and formation of metastases through adhesion molecule binding, expressed by vascular endothelial cells (VCAM and ICAM); tissue invasion through tumor metalloprotease production such as MMP-9; autoimmune diseases caused by dysregulation of the T cell or B cell immune systems, treatable by suppression of the T cell or B cell responses; acute allergic reactions including, but not limited to, asthma and chronic inflammatory diseases, mediated by pro-inflammatory cytokines including tumor necrosis factor (TNF) and IL-1, and rheumatoid arthritis, osteoarthritis, multiple sclerosis or insulin dependent diabetes mellitus (IDDM), associated with enhanced localization of inflammatory cells and relase of inflammatory cytokines and metalloproteases; smooth muscle cell, endothelial cell, fibroblast and other cell type proliferation in response to growth factors, such as PDGF-AA, BB, FGF, EGF, etc. (i.e., atherosclerosis, restenosis, stroke, and coronary artery disease); activation of human immunodeficiency virus infection (AIDS and AIDS related complex); HIV-associated dementia; kidney mesangial cell proliferation in response to IL-1, MIP-1α, PDGF or FGF; inflammation; kidney glomerular or tubular toxicity in response to cyclosporin A or amphotericin B treatment; organ toxicity (e.g., gastrointestinal or pulmonary epithelial) in response to a cytotoxic therapy (e.g., cytotoxic drug or radiation); effects of non-alkylating anti-tumor agents; inflammation in response to inflammatory stimuli (e.g., TNF, IL-1 and the like) characterized by production of metalloproteases or allergies due to degranulation of mast cells and basophils in response to IgE or RANTES; bone diseases caused by overproduction of osteoclast-activating factor (OAF) by osteoclasts; CNS diseases resulting from over-stimulation by pro-inflammatory neurotransmitters such as, acetylcholine, serotonin, leuenkephalin or glutamate; acute inflammatory diseases such as septic shock, adult respiratory distress syndrome; multi-organ dysfunction associated with inflammatory cytokine cascade; and combinations thereof.

In a large number of cells, signaling is dependent upon generation of a broad variety of PA species, some of which are generated from lyso-PA by the enzyme lyso-PA acyl transferase and some of which are generated from 2-O-acyl glycan-PI by $P_iG$-PLD. Generation of each of these PA species (the predominant forms being: 1-acyl and 1-alkyl 2-linoleoyl PA compounds, generated by LPAAT; and 1-myristyl 2-palmitoyl and 1-o-myristyl 2-palmitoyl, generated by $P_iG$-PLD) serves to effect both proliferative and/or inflammatory signaling in the diseases discussed and cell systems described above.

The inventive compounds are of particular significance for inhibiting IL-2-induced proliferative response. IL-2 signaling inhibition is potentially useful in the treatment of numerous disease states involving T-cell activation and hyperproliferation. Exemplary autoimmune diseases treated by inhibiting IL-2 signaling are lupus, scleroderma, rheumatoid arthritis, multiple sclerosis, glomerula nephritis as well as potential malignancies, including but not limited to, chronic myelogenous leukemia as well as others.

BRIEF DESCRIPTION OF THE DRAWINGS

FIG. 3A reports results obtained for several inventive compounds exhibiting inhibitive effects on murine thymocyte proliferation.

DETAILED DESCRIPTION OF THE INVENTION

Figure 1A:
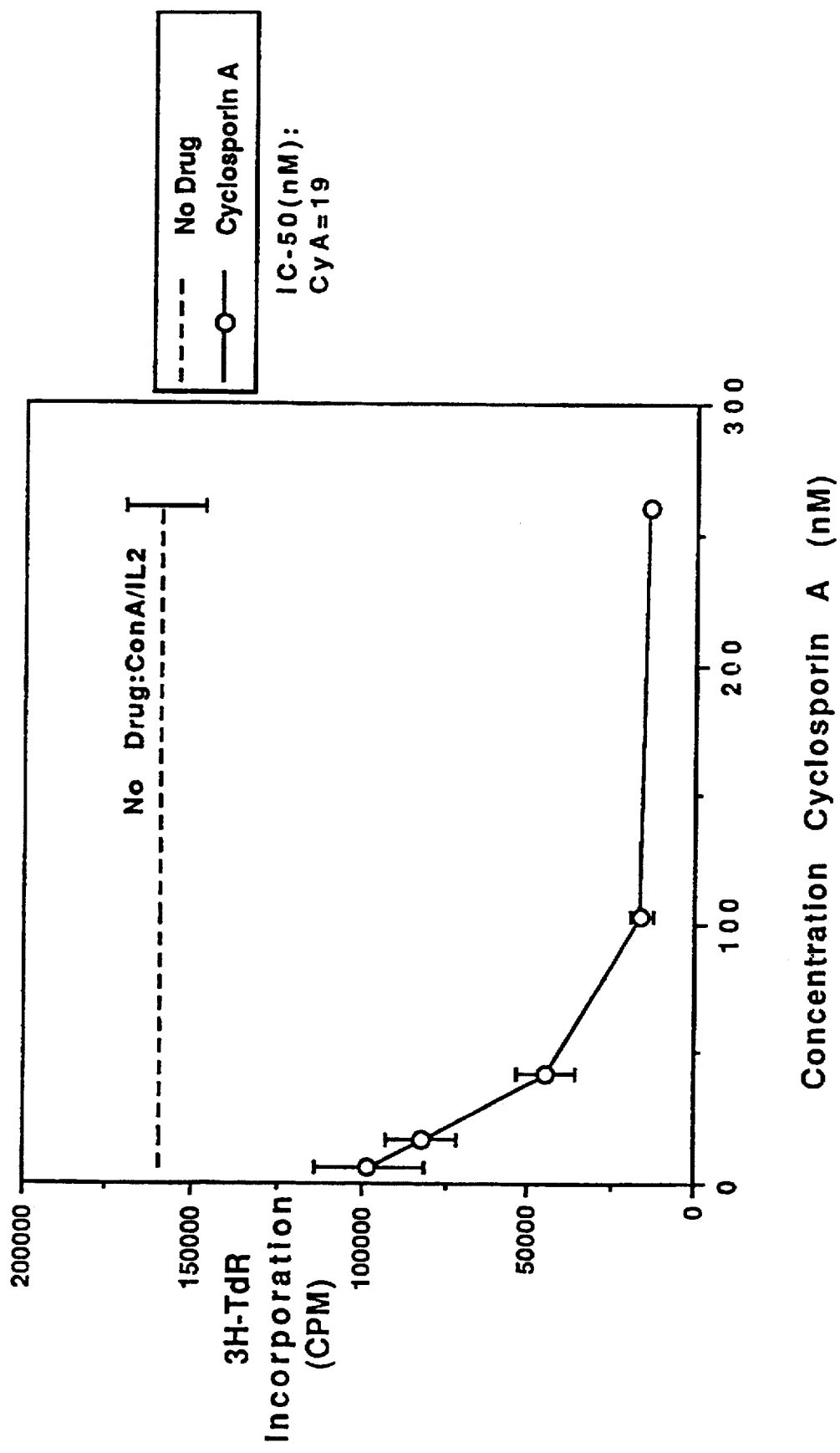
FIGS. 1A and 1B are dose response curves for both cyclosporin A (CsA, FIG. 1A) and various inventive compounds (FIG. 1B) for murine thymocyte proliferation co-stimulated by Concanavalin A (ConA) and interleukin-2 alpha (IL-2).

The invention provides a genus of compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D LPAAT=lysophosphatidic acid acyl transferase
PAPH=phosphatidic acid phosphohydrolase
PLD=phospholipase D
PAA=phosphoarachidonic acid
PLA2=phospholipase A2
PC=phosphatidyl choline "remodeled" PA, cyclic pathway=PAA, LPA, PA and DAG intermediates substituted with 1-saturated, 2-linoleoyl or 1,2-dioleoyl, dioleoy/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl, 2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. However, it is important to know whether or not each phospholipid species passes through a PA form previous to hydrolysis to DAG. The lyso-PA that is converted to PA and thence to DAG may be shown. The complexities of this second messenger pathway can be sorted by suitable analyses by fatty acyl side chain chemistry (i.e., by thin layer chromatography, gas-liquid chromatography, or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through the action of PAPH. Several minutes later, DAG is generated from PI through the classical phosphoinositide pathway. In many cells, DAG is derived from both PA that is being remodeled through a cycle whereby PA is sn-2 hydrolyzed by PLA-2, followed by sn-2 transacylation by LPAAT, and a PLD-pathway from PA that is generated from either PE or PC or both substrates by PLD.

A method described herein permits differentiation of the various subspecies of PA and DAG based upon acyl chain composition. This can differentiate those compounds that activate (and inhibit activation of) the present second messenger pathway from other pathways, such as the classical PI pathway. The present second messenger pathway involves substrates with unsaturated fatty acids in the sn-2 position other than arachidonate and those sub species of PAPH and LPAAT that are not involved in normal cellular housekeeping functions that are part of the classical PI pathway. The PAPH and LPAAT enzymes involved in the present second messenger pathway are exquisitely stereo specific for different acyl side chains and isomeric forms of substrates. Therefore, the inventive compounds are preferably, substantially enantiomerically pure, and preferably are the R enantiomer at the chiral carbon atom bonded to the hydroxyl group.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g., 1,2-sn-dioleoyl DAG, 1-alkyl,2-linoleoyl DAG and 1-alkyl,2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

An additional signaling pathway associated with inflammatory transduction and cell membrane perturbation generates a separate PA species, enriched in myristate and derived from GlyPI, as described above. Under these signaling conditions, the inventive compounds prevent activation of or directly inhibit the PiG-PLD, hydrolyzing GlyPI to PA and glycan inositol. In some tumor cells and TNF-activated cells (i.e., Type II receptors), the inventive compounds' efficacy may be dual inhibition of both LPAAT and GlyPI hydrolysis.

Experimental results confirm this inhibitive effect. Stimulation of CT-6 cells with IL-2 results in rapid hydrolysis of GlyPI species 15–45 seconds after stimulation, followed by rapid resynthesis of GlyPI. The inventive compounds prevent this hydrolysis and stimulate GlyPI synthesis, resulting in a significant GlyPI increase throughout stimulation without evidence of hydrolysis or formation of GlyPI-derived PA. Stimulation of human umbilical vein endothelial cells with TNF results in LPAAT-derived and Gly-PI-derived PA species. The inventive compounds inhibit formation of both PA species. Accumulation of lyso-PA and Gly-PI results.

Therapeutic Uses of the Inventive Compounds

The specific activation and/or inhibition of the second messenger pathway, as described above, activated primarily by various noxious stimuli, suggests that the inventive compounds are useful in treating a wide variety of clinical indications. Moreover, in vitro and in vivo data, presented herein, provides predictive data that a wide variety of clinical indications, having similar effects on the specific second messenger pathway, may be treated by the inventive compounds, which specifically inhibit the pathway, activated by noxious stimuli and mediated through, for example, inflammatory cytokines. In fact, the mechanism of action for the inventive compounds explains why these compounds have a multifarious clinical indications.

Activation of the second messenger pathway is a major mediator of response to noxious stimuli and results in cellular signals that lead to, for example, acute and chronic inflammation, immune response and cancer cell growth. However, all inhibitors do not inhibit all enzymes of this second messenger pathway. Although the inventive compounds may desirably inhibit many other unmentioned, noxious stimuli, they most effectively mediate the conditions discussed herein. Signals mediated by the present second messenger pathway include, for example, those cellular responses of LPS directly, T cell activation by antigen, B cell activation by antigen, cellular responses to IL-1 mediated through the IL-1 Type I receptor (but not the IL-1 Type II receptor), the TNF Type I receptor, growth stimulated by transformations including, but not limited to, activated oncogenes (e.g., ras, abl, her2-neu and the like), smooth muscle cell proliferation stimulated by platelet derived growth factor (PDGF), b-FGF and IL-1; T cell and B cell growth stimulation by IL-2, IL-4 or IL-7 and IL-4 or IL-6, respectively; and more generally, T cell receptor signaling.

In vitro, the inventive compounds: (1) block IL-1 signal transduction through the Type I receptor as shown, for example, by preventing IL-1 and IL-1 plus PDGF induction of proliferation of smooth muscle, endothelial and kidney mesengial cells; (2) suppress up-regulation of adhesion molecules as shown, for example, by blocking VCAM in endothelial cells; (3) inhibit TNF, LPS and IL-1 induced metalloproteases (an inflammation model); (4) block LPS, TNF or IL-1 induced metalloprotease and secondary cytokine production (for prevention and treatment of septic shock); (5) suppress T cell and B cell activation by antigen, for example, IL-2 and IL-4; (6) inhibit mast cell activation by IgE; (7) are cytotoxic for transformed cells and tumor cell lines, yet not for normal cells; and (8) block signaling by IL-2, IL-4, IL-6 and IL-7 on T and B cells.

The foregoing in vitro effects give rise to the following in vivo biologic effects, including, but not limited to, protection and treatment of endotoxic shock and sepsis induced by gram positive or gram negative bacteria, inhibition of tumor cell growth, synergistic immunosuppression, treatment of autoimmune diseases, suppression of allograft reactions, and stimulation of hair growth through reversal of an apoptotic process. The inventive compounds are most potent when used to prevent and treat septic shock, treat acute and chronic inflammatory disease, treat or prevent an autoimmune disease and stimulate hair growth (when applied topically).

The inventive compounds also are useful as an adjuvant to inhibit toxic side effects of drugs whose side effects are mediated through the present second messenger pathway.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/ PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of Interleukin-1 in Disease" (Dinarello et al., N. Engl. J. Med. (1993) 106:328) described the role of IL-1 as "an important rapid and direct determinant of disease." "In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure, and doses of 300 ng or more per kilogram of body weight may cause severe hypotension. The therapeutic advantage of blocking the action of IL-1 resides in preventing its deleterious biologic effects without interfering with the production of molecules that have a role in homeostasis. The present inventive compounds address the need identified by Dinarello and Wolff by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$) and leukotriene $B_4$ ($LTB_4$) and IL-8, an inflammatory cytokine with neutrophil-chemoattractant and neutrophil-stimulating properties. Tissue concentrations of $PGE_2$ and $LTB_4$ correlate with the severity of disease in patients with ulcerative colitis, and tissue concentrations of IL-1 and IL-8 are high in patients with inflammatory bowel disease. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent disease deterioration for acute and chronic myelogenous leukemias.

Insulin-dependent diabetes mellitus (IDDM) is considered to be an autoimmune disease with destruction of beta cells in the islets of Langerhans mediated by immunocompetent cells. Islets of animals with spontaneously occurring IDDM (e.g., BB rats or NOD mice) have inflammatory cells that contain IL-1. Therefore, the inventive compounds should be useful for the prevention of and treatment of IDDM.

IL-1 also plays a role in the development of atherosclerosis. Endothelial cells are a target of IL-1. IL-1 stimulates proliferation of vascular smooth muscle cells. Foam cells isolated from fatty arterial plaques from hypercholesterolemic rabbits contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. Activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and 1-o-alkyl or 1-o-alkenyl acylglycerol (AAG) species. The inventive compounds exert their activity by inhibiting one or both enzymes at an inner leaflet of the plasma membrane. Therefore, appropriate in vitro models for drug activity is to measure inhibition of stimulation caused by a pro-inflammatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of diunsaturated PA, which is about <0.1% of total membrane lipid mass, is sufficient to activate PLD activity. This quantity of PA is similar to that endogeneously synthesized by LPAAT. The PA-stimulated PLD acts upon PE, which should be localized to the inner leaflet of the cell membrane, which is enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 min) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are up-regulated in oncogenically transformed cells. For example, activating ras mutations result in increased generation of DAG on stimulation with mitogens, although the sources of DAG have differed between experimental systems. In non-transformed renal mesangial cells, IL-1β stimulation increased PLA2 and LPAAT activation, resulting in generation of sn-2 unsaturated PA and subsequent hydrolysis to DAG by phosphatidate phosphohydrolase. The ras transformation in NIH/3T3 cells up-regulates serum-stimulated generation of DAG and PA. The specific species of DAG stimulated by serum is dioleoyl and for PA, dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an up-regulation of PA through indirect stimulation of PLA2 and/or LPAAT activity. The inventive compounds inhibit the conversion of the upregulated lysoPA to PA and subsequently block the phenotypic changes induced by PA/DAG in the membrane.

The ability of the inventive compounds to inhibit generation of unsaturated phospholipids is mirrored by the ability of inventive compounds to inhibit proliferation and tumorogenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytes/macrophages is implicated in exacerbating or causing the disease. These include, for example, neurodegenerative diseases such as Alzheimers disease, endotoxemia or toxic shock syndrome (Tracey et al., *Nature* (1987) 330:662 and Hinshaw et al., *Circ. Shock* (1990) 30:279); cachexia (Dezube et al., *Lancet* (1990) 355:662), and adult respiratory distress syndrome (Miller et al., *Lancet* (1989) 2(8665):712). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., *N. Engl. J. Med.* (1989) 320:1585), chronic pulmonary inflammatory diseases such as silicosis and asbestosis (Piguet et al., *Nature* (1990) 344:245, and Bissonnette et al., *Inflammation* (1989) 13:329), and reperfusion injury (Vedder et al., *Proc. Natl. Acad. Sci.* USA (1990) 87:2643).

The inventive compounds provide a method for maintaining homeostasis in cells contacted by primary stimuli by mitigating the effects of these primary stimuli on the secondary signaling pathways invoked within seconds of a primary stimulus. For example, administration of an inventive compound in vivo or ex vivo provides a method to modify cellular behavior, the method comprising contacting cells (in vivo or ex vivo), whose behavior is to be modified, with an effective amount of an inventive compound or a pharmaceutical composition thereof wherein said method is a method to: (1) inhibit proliferation of tumor cells and said amount is sufficient to inhibit said proliferation; (2) suppress activation of T-cells by antigen or IL-2 stimulation, and said amount is sufficient to promote said activation; (3) suppress activation of monocyte/macrophage cells by endotoxin, TNF, IL-1 or GM-CSF stimulation and said amount is sufficient to suppress said activation; (4) suppress antibody production of B-cells in response to an antigen, IL-4 or CD40 ligand and said amount is sufficient to suppress said antibody production; (5) inhibit the proliferation of smooth muscle cells in response to growth factors capable of stimulating said proliferation and said amount is sufficient to inhibit said proliferation; (6) lower systemic vascular resistance conferred by endothelial cells and said amount is sufficient to reduce the release of hypertension-inducing substances; (7) lower systemic vascular resistance induced by endothelial cells and said amount is sufficient to enhance the release of anti-hypertensive substances; (8) lower expression of adhesion molecules induced by enhancers thereof, and said amount is sufficient to lower said expression; (9) suppress the activation of T-cells and macrophages by HIV and said amount is sufficient to suppress said activation thus inhibiting viral replication; (10) inhibit the proliferation of kidney mesangial cells in response to stimulation by IL-1 and/or MIP-1α and/or PDGF and/or FGF and said amount is sufficient to inhibit said proliferation; (11) enhance the resistance of kidney glomerular or tubular cells to cyclosporin A or amphotericin B and said amount is sufficient to enhance said resistance; (12) prevent the release of MIP-1α by IL-1, TNF, or endotoxin stimulated monocytes and macrophages; (13) prevent the release of platelet activating factor by IL-1, TNF, or endotoxin treated megakaryocytes, fibroblastic cells, and macrophages; (14) prevent the down-regulation of receptors for cytokines in TNF-treated hematopoietic progenitor cells and said amount is sufficient to prevent said down-regulation; (15) suppress the production of metalloproteases in IL-1-stimulated or TNF-stimulated glomerular epithelial cells or synovial cells and said amount is sufficient to enhance said production; (16) enhance the resistance of gastrointestinal or pulmonary epithelial cells to cytotoxic drugs or radiation and said amount is sufficient to enhance said resistance; (17) enhance the antitumor effect of a non-alkylating antitumor agent and said amount is sufficient to enhance said effect; (18) to inhibit the production of osteoclast activating factor in response to IL-1, and said amount is sufficient to inhibit said production; (19) inhibit degranulation in response to IgE, and said amount is sufficient to inhibit said degranulation; (20) enhance the release of adrenergic neural transmitters, dopamine, norepinephrine, or epinephrine, or the neurotransmitter acetylcholine, and said amount is sufficient to enhance said release; (21) modulate the post-synaptic "slow current" effects of the adrenergic neurotransmitters dopamine, epinephrine, or norepinephrine, or the neurotransmitter acetylcholine, and said amount is sufficient to modulate such slow currents; (22) suppress signaling by neurotransmitters including acetyl choline, leuenkephalin and serotonin; or (23) increase seizure theshold.

The compounds of the invention can inhibit certain VEGF (vascular endothelial growth factor), FGF (fibroblast growth factor) and PDGF (platelet derived growth factor) effects in vivo, such as inhibition of angiogenesis or restenosis. For example, Ferns et al. (*Science* (1991) 253:1129) have shown that neointimal smooth muscle chemotaxis and angioplasty are inhibited in rats using a neutralizing antibody to PDGF. Also, Jawien et al. (*J. Clin Invest.* (1992) 89:507) have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., *Science* (1990) 248:1009). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., *Int. J. Cancer* (1990) 46:1066), metastatic melanoma cells (Yamanishi et al., *Cancer Res.* (1992) 52:5024), and glial tumors (Fleming et al., *Cancer Res.* (1992) 52:4550).

In Vitro Assays for Physiologic and Pharmacological Effects of the Inventive Compounds Various in vitro assays can be used to measure effects of the inventive compounds to modulate immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluting the drawn blood with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 minutes at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 µl complete medium are co-cultured with approximately $10^5$ autologous (control culture) or allogeneic (stimulated culture) PBMC cells, wherein the allogeneic cells are from HLA disparate individuals. Varying doses of compounds are added at the time of addition of cells to the microtiter plate. The cultures are incubated for 6 days at 37° C. in a 5% $CO_2$ atmosphere. At the conclusion of the incubation, tritiated thymidine is added (for example, 1 µCi/well of 40 to 60 Ci/mmole) and proliferation determined by liquid scintillation counting.

A thymocyte costimulator assay is conducted to evaluate the inventive compounds to inhibit activation and proliferation of thymocytes caused by stimulation with Con A and interleukin-1 (IL-1), or interleukin-2 (IL-2). Thymuses are obtained from mice (e.g., female Balb/C mice) and the thymuses are removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contaminating red cells are lysed, and viable cells are resuspended and counted. Thymocytes are plated (e.g., 96-well plates at a density of $2\times10^5$ cells/well) and a stimulating agent, such as. Con A, IL-1 (e.g., IL-1α) or IL-2 is added to the well. The cells are incubated for 4 days at 37° C. On the fourth day, the cells are pulsed with tritiated thymidine and cell proliferation determined. Inventive compounds are added simultaneously with stimulating agent addition.

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability stain (e.g., 2',7'-bis-(2-carboroxyethyl)-5-(and -6)-carboxyfluorescein acetoxymethyl ester, BCECF excitation 488 nm and emission 525 nm) 24, 48 or 72 hours after addition of the drug.

Another assay for measuring activity of the inventive compounds involves determining PDGF, FGF or VEGF proliferative response using either mouse NIH-3T3 (Balb) cells or human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 µg/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Drug inhibitory activity can also be measured by determining levels of vascular cell adhesion molecule (VCAM) in stimulated cells. Early passage human umbilical vein endothelial cells (HUVEC) (obtained from commercial suppliers such as Cell Systems, Inc. or Clonetics) are cultured in media (e.g., Hepes buffered media, Cell Systems) containing 10% fetal bovine serum, and supplemented with a stimulating agent, such as fibroblast growth factor (acidic FGF, Cell Systems, Inc.) or TNF. The cells are plated into wells of a microtiter plate (e.g., $5\times10^4$ per well) and allowed to incubate at 37° C. for 72 hours. The resting cells are removed (e.g., 20–30 minutes treatment with 0.4% EDTA), washed in media (e.g., phosphate buffered saline plus 0.1% bovine serum albumin with 0.01% sodium azide) and labeled on ice with a monoclonal antibody ("first antibody") recognizing human VCAM (e.g., 1 µg of a murine monoclonal antibody recognizing human VCAM, Genzyme). After 60 minutes on ice, the cells are washed (preferably twice) with cold wash media and incubated with an antibody that recognizes the first antibody (e.g., 1 µg of goat anti-mouse IgG conjugated with phycoerythrin, CalTag, Inc.). After 30 minutes on ice, the cells are washed twice and analyzed on a flow cytometer (Coulter Elite®) at appropriate emission and excitation wavelengths (e.g., for phycoerythrin use excitation at 488 nm and emission at 525 nm).

One in vitro assay measures inhibition of relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of an inventive compound at varying dosage levels. Target cells include, for example, subcellular entities, such as, microsomes derived from mesenchymal and/or ectodermal cells, particularly microsomes from marrow stromal cells or human or rat mesangial cells; microsomes or synaptosomes derived from bovine brain; plasma membrane-enriched microsomes, plasma membranes derived as described in Bursten et al. (*J. Biol. Chem.* (1991) 226:20732–20743), or detergent-solubilized microsomes; synaptosomes, and membranes or other cell preparations solubilized using, for example, NP-40, Miranal, SDS or other neutral detergents; and detergent-solubilized, recombinant, or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, *Biochemistry* (1991) 30:6195–6203. A Rainin® mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

An inventive compound can be assayed for activity protecting TNF-mediated cytotoxicity. In this assay, L929 murine fibroblast cells ($10^4$ cells per well) are incubated with either compounds at varying doses and media control for two hours. TNF-$\alpha$ (R&D Systems) is added at a concentration of 500 pg/ml, which is four times the LD50 of TNF (125 pg/ml). The cells plus (or minus) drug and TNF were incubated for 40 hours at 37° C. The media is removed, replaced with fresh media containing 2% serum and 10 µg/ml of BCECF fluorescent dye and incubated for 30 minutes The fluorescent dye-containing media is removed and replaced with PBS (phosphate buffered saline) and each well was assayed for fluorescence.

Another assay measures the effects of drug to inhibit adhesion of THP-1 cells to TNF-activated HUVEC cells In this experiment, HUVEC cells are induced with human TNF-$\alpha$ (20 ng/ml) and drug at varying concentrations for 14–16 hours. THP-1 cells (a human monocytic leukemia cell line) are incubated and labeled with BCECF (10 µg/ml), a fluorescent dye. The THP-1 cell preparation ($2.5 \times 10^4$ cells per well) is layered on top of the activated HUVEC cells. The cells are reverse spun to remove partially adhering and nonadhering THP-1 cell. The adherent THP-1 cells are measured by fluorescence on a fluorescent plate reader.

Some of the inventive compounds are effective for inhibiting yeast cell growth. This effect can be verified by assaying growth of the yeast strain *Saccharomyces cervisiae*. A control yeast stain *Saccharomyces cervisiae* (BIO 101, Inc.) is grown overnight in YEPD broth at 30° C. A 1:100 dilution of the yeast culture is made with fresh YEPD broth. 100 µl Aliquots of the diluted culture are distributed into 96-wells titer plates. 100 µl Aliquots of drug, diluted in YEPD broth, were then added to the wells. The titer plates are incubated at room temperature with continuous shaking. The cell density of the individual cultures are determined using a mircoplate reader with a A630 filter. The A630 of the individual yeast cultures are compared to control samples without adding drug. This assay is predictive of direct antimicrobial, particularly yeast and fungal, activity of the drugs studied.

A serotonin release assay is utilized to study the utility of the inventive compounds for treatment of asthma and allergy. This assay measures mast cell degranulation, which is an early phase reaction to allergen challenge. Mast cells grown in tissue culture are first loaded with $^3$H serotonin, which is incorporated into the granules in the cells. The mast cells are sensitized with antigen specific monoclonal IgE, and then triggered to degranulate with the specific antigen (dinitorphenol bound to BSA (DNP)). When the cells degranulate, $^3$H Serotonin is released into the medium, and can be measured directly. The ability of the inventive compounds to inhibit the degranulation response is determined by the decrease in $^3$H Serotonin released in the presence of drug and is represented as % INHIBITION. The IC50 of any given compound is determined by the ability of that compound to inhibit degranulation by 50%.

Specifically, the serotonin release assay seeds $2 \times 10^5$ cells in 0.5 ml medium in duplicate for spontaneous release, IgE+DNP, IgE+DNP+EtOH (vehicle control), and inventive compounds. One µCi [$^3$H]-Serotonin/ml (i.e., 0.5 µCi/well) (NEN Research Products, cat. #NET-398 Hydroxytryptamine Binoxalate, 5-[1,2-$^3$H(N)]-(Serotonin Binoxalate, [1,2-$^3$H(N)]-)) and 1 µl/ml IgE is added. The cells are incubated for 18 hours at 37° C. in 5% $CO_2$, washed twice with 0.5 ml Isotonic Buffer (25 mM disodium PIPES pH 7.1,100 mM NaCl, 5 mM KCl, 5 mM glucose, 0.4 mM $MgCl_2$, 1 mM $CaCl_2$, 0.1 % BSA), and sterile filtered. 250 µl Isotonic Buffer is added per well and the plates are equilibrated in an incubator for about 10 minutes. Drug is added and cells are activated with 40 ng/ml DNP-BSA (1 mg/ml Diluted 1:200 in Isotonic Buffer) for 45 minutes using 2 µl/250 µl. Spontaneous release is determined in incubated cells with 250 µl Isotonic Buffer for 45 minutes and the reaction is stopped by removing supernatant and centrifuging at ~4000 rpm in a microfuge for 15 seconds to remove any detached cells. Released radiolableled serotonin is counted. To determine amount of $^3$H-serotonin incorporated into the cells, (a) remove Isotonic Buffer and lyse cells by adding 250 µl 1% Triton-X100 in PBS, (b) add to 5 ml scintillation fluid, (c) wash 2x with Triton/PBS, and (d) add washes to scintillation tube. Percent serotonin release is calculated by dividing the amount of released serotonin by the sum of incorporated plus released serotonin and correcting for spontaneous released serotonin. Compound inhibition is calculated by dividing the percent serotonin release in the presence of a compound by the percent serotonin release in the absence of the compound.

There are a series of in vitro assays that can be used to measure immunosuppressive activity of a particular compound. These assays are predictive models for treatment or prevention of autoimmune diseases, such as diabetes, lupus, arthritis, and the like. A first assay measures immunosuppressive activity of a drug at the B cell level. Spleens from adult mice contain immature B cells that express surface IgM. Cross-linking the surface IgM with an anti-mu antibody results in B cell proliferation. Additionally, this activation results in an increased expression of interleukin-4 receptors(IL-4R) on the surface of such cells. IL-4 acts as a growth factor for B cells and will increase the amount of proliferation induced by anti-mu. In the first assay, a mixture of anti-mu and murine IL-4 is added to murine splenocytes to cause their proliferation. Mice spleens are obtained from adult mice and a single cell suspension is prepared in RPMI 1640 medium supplemented with 10% FCS. Cells (200,000) are plated into flat-bottomed wells and pre-incubated for 1–2 hours with various concentrations of drug or PBS if it is a control well. A mixture of anti-mu and murine is added to the wells at a final concentration of 5 µg/ml anti-mu and 12.5 ng/ml IL-4 and plates are incubated for three days. Proliferation is determined on the third day with a pulse of tritiated thymidine. The IC50 concentration of a particular inventive compound is the concentration of the compound that results in a 50% inhibition of the proliferation obtained from the positive control.

A second immune suppression assay measures a T cell component to the immune reaction. Lymph nodes contain a mixture of cells including T cells, B cells and macrophages. Although the proliferating cells in this assay are T cells, the response is also dependent upon an antigen presenting cell such as a macrophage as well as an elaboration of various immunoregulatory cytokines. Murine T cells will proliferate in vitro in response to a soluble protein antigen if they are first primed with the antigen in vivo. In vivo priming involves emulsifying the antigen (chicken ovalbumin or OVA) in complete Freunds adjuvant and injecting 50 μg of OVA into both hind footpads of adult Balb/c mice. Fourteen days later the draining lymph nodes (popliteal) are removed and a single cell suspension is prepared in RPMI 1640 supplemented with 10% fetal calf serum. The lymph node cells (200,000) are plated into flat-bottom wells and OVA (200 μg/ml) and/or drug is added to appropriate wells and incubated for 5 days. Proliferation is determined and IC50's calculated as above.

A third assay measures an ability of an inventive compound to inhibit IL-2 induced proliferation of murine thymocytes. Thymus glands are obtained from 4–6 week old mice and plated as a single cell suspension into flat bottomed wells in RPMI 1640 medium supplemented with 10% fetal calf serum. The inventive compounds are added to appropriate wells and the cells are incubated for 1–2 hours. Concanavilin A (ConA, 0.25 μg/ml) and IL-1 (20 ng/ml) are added and the plates are incubated for 4 days. Cell proliferation is determined as above.

Compounds of the Invention

The inventive compounds are useful for a large variety of therapeutic indications for modulating disease by intracellular signaling through one or two specific intracellular signaling pathways. In addition, the inventive compounds and compositions are suitable for normal routes of therapeutic administration (e.g., parenteral, oral, topical, etc.).

The invention provides for a class of amino alcohol substituted compounds, preferably heterocyclic compounds. The inventive compounds and inventive pharmaceutical compositions thereof have the formula:

(X)j—(core moiety), wherein j is an integer from one to three, the core moiety comprises at least one, five- to seven-membered ring and X is a racemic mixture, R or S enantiomer, solvate, hydrate, or salt of:

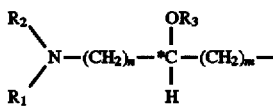

wherein *C is a chiral carbon atom; n is an integer from one to four (preferably from one to three); one or more carbon atoms of $(CH_2)_n$ may be substituted by a keto or hydroxy group; m is an integer from one to fourteen (preferably one to eight or ten to fourteen); independently, $R_1$ and $R_2$ are hydrogen, a straight or branched chain alkane or alkene of up to twelve carbon atoms in length, or $-(CH_2)_w R_5$, w being an integer from two to fourteen and $R_5$ being a mono-, di- or tri-substituted or unsubstituted aryl group, substituents on $R_5$ being hydroxy, chloro, fluoro, bromo, or $C_{1-6}$ alkoxy; or jointly, $R_1$ and $R_2$ form a substituted or unsubstituted, saturated or unsaturated heterocyclic group having from four to eight carbon atoms, N being a hetero atom; and $R_3$ is hydrogen or $C_{1-3}$; or

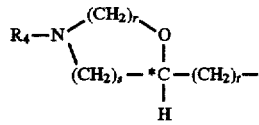

wherein $R_4$ is a hydrogen, a straight or branched chain alkane or alkene of up to eight carbon atoms in length, $-(CH_2)_w R_5$, w being an integer from two to fourteen and $R_5$ being a mono-, di- or tri-substituted or unsubstituted aryl group, substituents on $R_5$ being hydroxy, chloro, fluoro, bromo, or $C_{1-6}$ alkoxy, or a substituted or unsubstituted, saturated or unsaturated heterocyclic group having from four to eight carbon atoms r and s are independently integers from one to four; the sum (r+s) is not greater than five; t is an integer from one to fourteen; and one or more carbon atoms of $(CH_2)_s$ or $(CH_2)_t$ may be substituted by a keto or hydroxy group.

The core moiety is at least one five- to seven-membered ring, preferably having from one to three, five- to six-membered ring structures in a predominantly planar configuration. Preferably, the amino alcohol substituent (X) is bonded to a ring nitrogen if one exists. For example, the core moiety may be selected from the group consisting of substituted or unsubstituted: barbituric acid; benzamide; benzene; biphenyl; cyclohexanedione; cyclopentanedione; delta-lactam; flutarimide; glutarimide; homophthalimide; imidazole amide; isocarbostyrile; lumazine; napthlalene; pteridine; pthalimide; piperidine; pyridine; pyrimidine; pyrrole amide; quinazolinedione; quinazolinone; quinolone; recorsinol; stilbene; succinimide; theobromine; thymine; triazine; tricyclododecane; uracil or xanthine.

Preferred cores include substituted or unsubstituted glutarimide, methylthymine, methyluracil, thymine, theobromine, uracil and xanthine, most preferably halogen-substituted xanthine. Exemplary preferred cores include, but are not limited to: 1,3-cyclohexanedione, 1,3-cyclopentanedione; 1,3-dihydroxynaphthalene; 1-methyllumazine; methylbarbituric acid; 3,3-dimethylflutarimide; 2-hydroxypyridine; methyldihydroxy-pyrazolopyrimidine (preferably, 1,3-dimethyldihydroxypyrazolo[4,3-d]pyrimidine); methylpyrrolopyrimidine (preferably, 1-methylpyrrolo[2,3-d]pyrimidine); 2-pyrrole amides; 3-pyrrole amides; 1,2,3,4-tetrahydroisoquinolone; 1-methyl-2,4(1H,3H)-quinazolinedione (1-methylbenzoyleneurea); quinazolin-4 (3H)-one; alkyl-substituted ($C_{1-6}$) thymine; methylthymine; alkyl-substituted ($C_{1-6}$) uracil; 6-aminouracil; 1-methyl-5,6-dihydrouracil; 1-methyluracil; 5- and/or 6-position substituted uracils; 1,7-dimethylxanthine, 3,7-dimethylxanthine; 3-methylxanthine; 3-methyl-7-methylpivaloylxanthine; 8-amino-3-methylxanthine; and 7-methylhypoxanthine.

Preferably, X is bonded to a nitrogen of the core moiety, most preferably, the core moiety is xanthine and X is bonded to an $N_1$ xanthine nitrogen and $N_3$ and $N_7$ xanthine nitrogens are independently substituted by a member selected from the group consisting of hydrogen, methyl, fluoro, chloro and amino.

The invention provides a pharmaceutical composition comprising an inventive compound and a pharmaceutically acceptable excipient. The pharmaceutical composition may be formulated for oral, parenteral or topical administration to a patient.

The invention includes a method for treating an individual having a variety of diseases, wherein the disease is characterized by or can be treated by inhibiting an immune response or a cellular response to external or in situ primary stimuli, wherein the cellular response is mediated through a specific phospholipid-based second messenger acting adjacent to a cell membrane inner leaflet. The second messenger pathway is activated in response to various noxious or proliferative stimuli, characteristic of a variety of disease states. The biochemistry of this second messenger pathway is described herein.

More specifically, the invention includes methods for treating or preventing clinical symptoms of various disease states or reducing toxicity of other treatments by inhibiting cellular signaling through the second messenger pathway. Disease state or treatment-induced toxicity are selected from the group consisting of proliferation of tumor cells in response to an activated oncogene; hematocytopenia caused by cytoreductive therapies; autoimmune diseases caused by a T cell response or a B cell response and antibody production; septic shock; resistance of mesenchymal cells to tumor necrosis factor (TNF); proliferation of smooth muscle cells endothelial cells, fibroblasts and other cell types in response to growth factors, such as PDGF-AA, BB, FGF, EGF, etc. (i.e., atherosclerosis, restenosis, stroke, and coronary artery disease); human immunodeficiency virus infection (AIDS and AIDS related complex); proliferation of kidney mesangial cells in response to IL-1 MIP-1α, PDGF or FGF; inflammation; kidney glomerular or tubular toxicity in response to cyclosporin A or amphotericin B treatment; organ toxicity (e.g., gastrointestinal or pulmonary epithelial) in response to a cytoreductive therapy (e.g., cytotoxic drug or radiation); enhancing antitumor effects of nonalkylating antitumor agents; allergies in response to inflammatory stimuli (e.g., TNF, IL-1 and the like) characterized by production of cell surface metalloproteases or by degranulation of mast cells and basophils in response to IgE, bone diseases caused by overproduction of osteoclast-activating factor (OAF) by osteoclasts, CNS diseases caused by reduced signal transduction of the neurotransmitters epinephrine and acetylcholine, and combinations thereof. The inventive compounds are also useful as antimicrobial agents to directly treat fungal or yeast infections and to indirectly treat bacterial or viral infections through an immune stimulation and pro-hematopoietic effect.

The invention further provides a pharmaceutical composition comprising an inventive compound and a pharmaceutically acceptable excipient, the pharmaceutical composition being formulated for oral, parenteral or topical administration to a patient. A pharmaceutical composition may alternatively comprise one or a plurality of inventive compounds and a pharmaceutically acceptable carrier or excipient. Treatment of individuals with an inventive compound or pharmaceutical composition may include contacting with the inventive compound in vitro culture, in an extracorporeal treatment, or by administering (oral, parenteral or topical) the inventive compound or pharmaceutical composition to a subject whose cells are to be treated.

Synthesis of the Inventive Compounds

The invention includes a method for preparing the inventive compounds. An exemplary method for preparing the inventive compounds is discussed below and in the following examples. In a synthesis according to the invention, a compound containing a desired core (intended as a "core moiety" in compounds of the invention) undergoes a reaction to produce an anion of the core-containing compound and subsequently reacting the anion with a substituted olefin to displace a targeted functional group on the olefin, resulting in an intermediate product. A predetermined amount of a core-containing compound is reacted with a suitable base, a solvent and a substituted olefin, the substituted olefin having at least one functional group which may be substituted in a displacement reaction by the desired core-containing compound.

Preferred bases include, but are not limited to, sodium hydride, sodium amide, sodium alkoxide, lithium hydride, potassium hydride, lithium amide, sodium amide and potassium amide. An especially preferred base is sodium hydride. Preferred solvents may be dimethylsulfoxide, dimethylformamide, or an alcohol. Exemplary preferred alcohols include, but are not limited to, methanol, ethanol or isopropanol. Any substituted olefin comprising a chain structure of the inventive compounds may be used in the reaction according to the invention. Preferred olefins may be ω-substituted olefins. Preferred substituted olefins include, but are not limited to halo-substituted olefins.

The intermediate product having a composite structure of the core-containing compound and substituted olefin, may subsequently be converted to a corresponding epoxide. In the method according to the invention, the intermediate product may be reacted with an organic peracid to obtain a desired epoxide. Preferred, exemplary organic peracids include 3-chloroperoxybenzoic acid, peracetic acid and trifluoroperacetic acid. An especially preferred peracid is 3-chloroperoxybenzoic acid.

Alternatively, the intermediate product may be converted first to a corresponding diol by reacting the intermediate product with a suitable oxidizing agent. Preferred oxidizing agents include, but are not limited to, osmium tetroxide. Preferred oxidizing agents, such as osmium tetroxide may require a catalytic amount of the oxidizing agent in the presence of a regenerating agent. Exemplary, regenerating agents may be 4-methylmorpholine-N-oxide and trimethylamine-N-oxide. An especially preferred regenerating agent is 4-methylmorpholine-N-oxide. In a subsequent halogenation reaction, the resulting diol is converted to a haloester using a halogenating agent in the presence of an organic acid. Exemplary halogenating agents include hydrogen bromide and hydrogen chloride. Preferred organic acids may be acetic acid and propionic acid. The resulting haloester is subsequently reacted with a basic esterhydrolyzing reagent to obtain a the desired epoxide product. Preferred esterhydrolyzing agents include, but are not limited to metal alkoxides and metal hydroxides. Especially preferred metal alkoxides are sodium methoxide, ethoxide, isopropoxide and pentoxide. A preferred metal hydroxide is sodium hydroxide.

A final step in the inventive method is preparation of the desired inventive compound from a core-containing epoxide, synthesized in the foregoing procedure. The final step may be accomplished by either of two preferred methods. In a first method, the core-containing epoxide is heated in the presence of a substituted or unsubstituted amine having functional groups which are present in the final inventive compound. Preferred amine functional groups are disclosed above.

A second method comprises reacting the unsubstituted or substituted amine with the core-containing epoxide and a reaction activator in a solvent. Exemplary reaction activators include lithium perchlorate. Preferred solvents are disclosed above.

Exemplary, preferred compounds of the invention include both R and S enantiomers and racemic mixtures of the following compounds:

| COMPOUND NO. | NAME |
|---|---|
| 1 | N-(9-Octylamino-8-hydroxynonyl)phthalimide |
| 2 | N-(11-Octylamino-10-hydroxyundecyl)homophthalimide |
| 3 | 1-(5-Hydroxy-6-(N-benzyl)aminohexyl)-3-methylbenzoyleneurea |
| 4 | 3-(11,10-Hydroxyundecyl)quinazoline-4(3H)-one |
| 6 | 2-(11-Octylamino-10-hydroxyundecylcarboxamido)-octylcarboxamidobenzyl |
| 8 | 1-(9-Octylamino-8-hydroxynonyl)-3-methylxanthine |
| 9 | 1-(9-Tetradecylamino-8-hydroxynonyl)-3-methylxanthine |

| COMPOUND NO. | NAME | COMPOUND STRUCTURE |
|---|---|---|
| 10 | 1-(11-Octylamino-10-hydroxyundecyl)-3-methylxanthine | 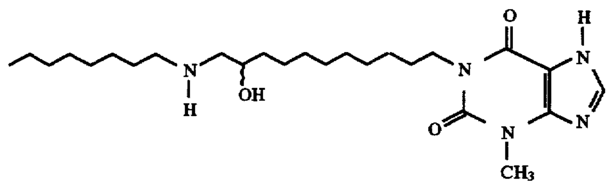 |
| 11 | 7-(11-Octylamino-10-hydroxyundecyl)-1,3-dimethylxanthine | 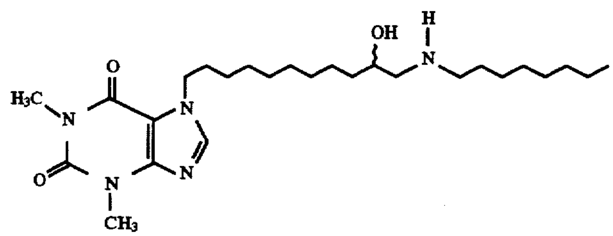 |
| 12 | 1-(11,10-Octylamino-10-hydroxyundecyl)-1-methyl-2,4-dioxotetrahydropteridine | 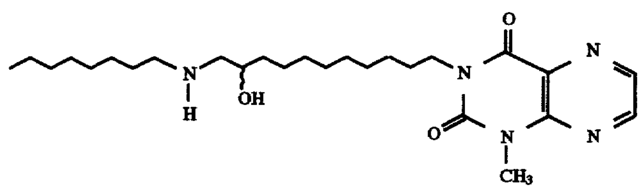 |
| 13 | 1-(5-hydroxy-6-(N-benzyl)aminohexyl)-3,7-dimethylxanthine | 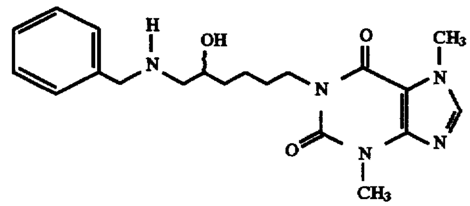 |
| 14 | 1-(5-hydroxy-6-(N-propyl)aminohexyl)-3,7-dimethylxanthine | 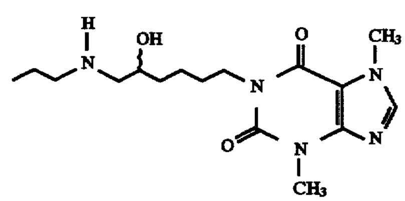 |
| 15 | N-(11-Octylamino-10-hydroxyundecyl)glutarimide | 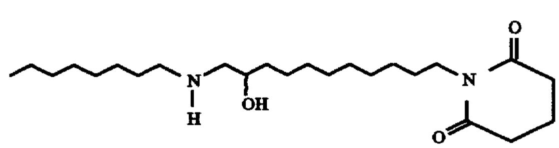 |
| 16 | N-(11-Octylamino-10-hydroxyundecyl)-2-piperidone | 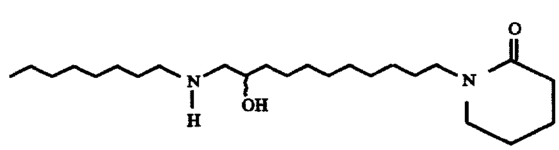 |

| | | |
|---|---|---|
| 17 | N-(11-Octylamino-10-hydroxyundecyl)succinimide | 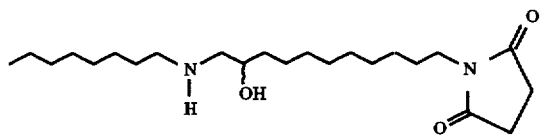 |
| 18 | 2-(11-Octylamino-10-hydroxyundecyl)-1,3-dimethoxybenzene | 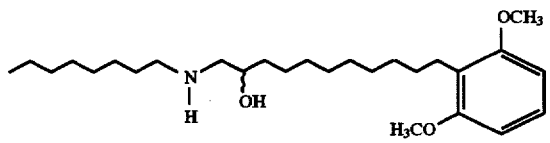 |
| 19 | 3-(5-hydroxy-6-(N-propyl)aminohexyl)-1-methyluracil | 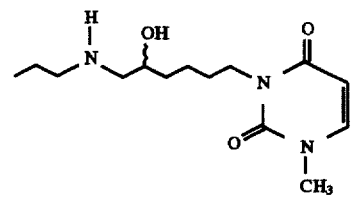 |
| 20 | 3-(9-Octylamino-8-hydroxynonyl)-1-methyluracil | 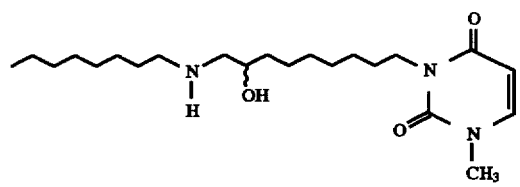 |
| 21 | 3-(11-Octylamino-10-hydroxyundecyl)-1-methyluracil | 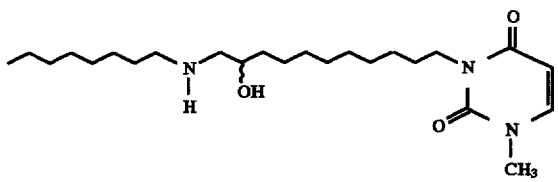 |
| 22 | 3-(11-Octylamino-10-hydroxyundecyl)-1-methyldihydrouracil | 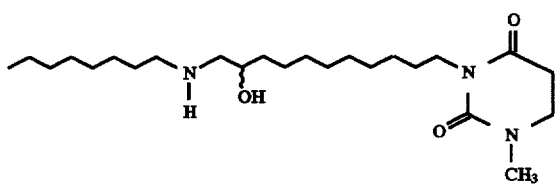 |
| 23 | 3-(9-Octylamino-8-hydroxynonyl)-1-methylthymine | 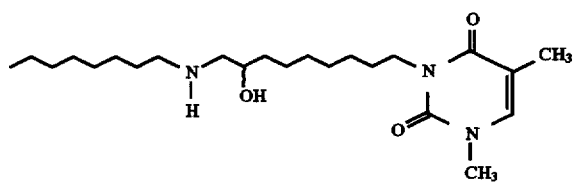 |

24 3-(5-Hydroxy-6-(N-undecyl)aminohexyl)-1-methylthymine
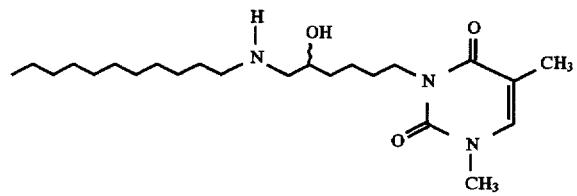
25 3-(11-Octylamino-10-hydroxyundecyl)-1-methylthymine
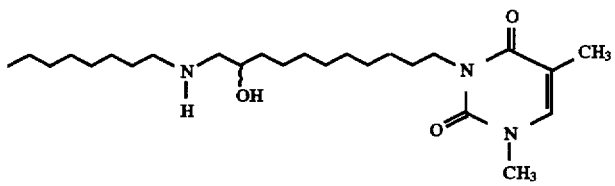
26 3-(6-Propylamino-5-hydroxyhexyl)-1-methylthymine
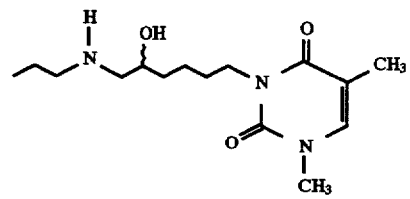
27 1-(8-hydroxy-9-(N-benzyl)aminononyl)-3,7-dimethylxanthine
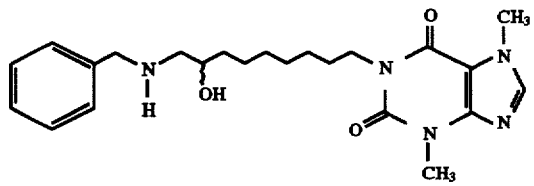
28 1-(5-hydroxy-6-(N-octyl)aminohexyl)-3,7-dimethylxanthine
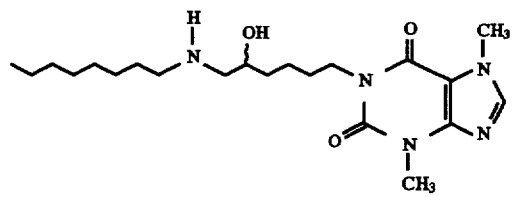
29 1-(5-hydroxy-6-(N-(4-phenyl)butyl)aminohexyl)-3,7-dimethylxanthine
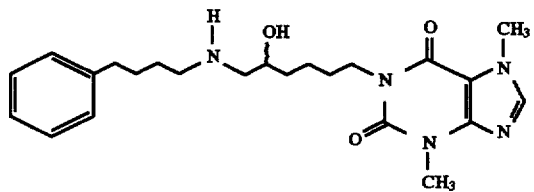
30 1-(6-Undecylamino-5-hydroxyhexyl)-3,7-dimethylxanthine
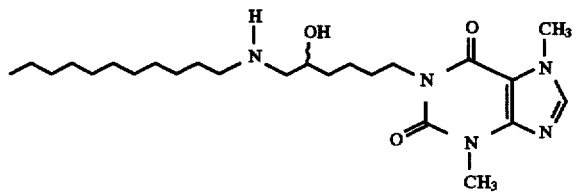

| 31 | 32 |
|---|---|
| 31  1-(5-hydroxy-6-(N-cyclohexylmethyl)aminohexyl)-3,7-dimethylxanthine | 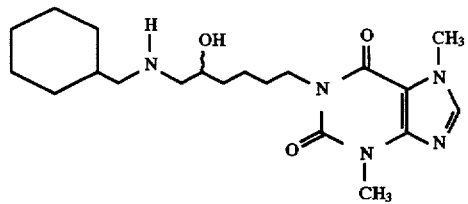 |
| 32  1-(5-hydroxy-6-(N-(6-hydroxy)hexyl)aminohexyl)-3,7-dimethylxanthine | 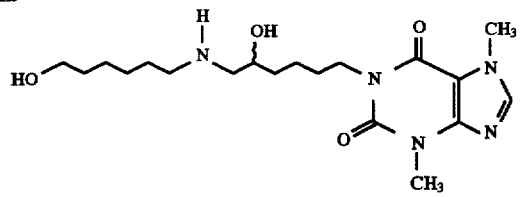 |
| 33  1-(5-hydroxy-6-(N,N-dihexyl)aminohexyl)-3,7-dimethylxanthine | 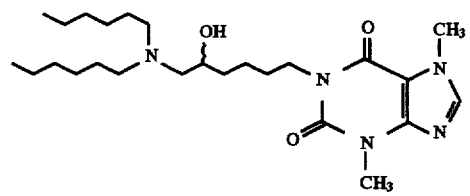 |
| 34  1-(5-hydroxy-6-(N-(4-methoxy)benzyl)aminohexyl)-3,7-dimethylxanthine | 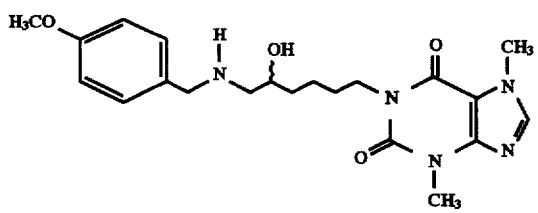 |
| 35  1-(8-hydroxy-9-(N-octyl)aminononyl)-3,7-dimethylxanthine | 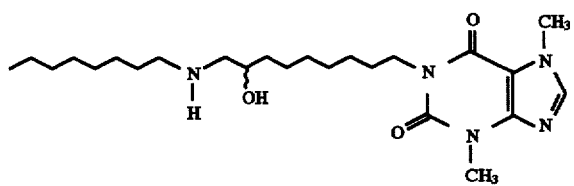 |
| 36  1-(5-hydroxy-6-(N-tetradecyl)aminohexyl)-3,7-dimethylxanthine | 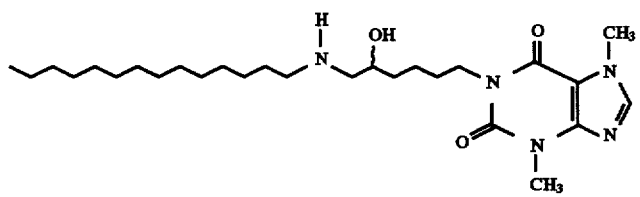 |
| 37  1[6-(Cyclopropylmethylamino)-5-hydroxyhexyl)]-3,7-dimethylxanthine | 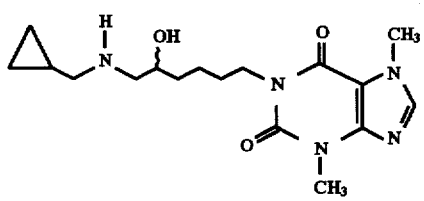 |

38  1-(6-Decylamino-5-hydroxyhexyl)-3,7-dimethylxanthine
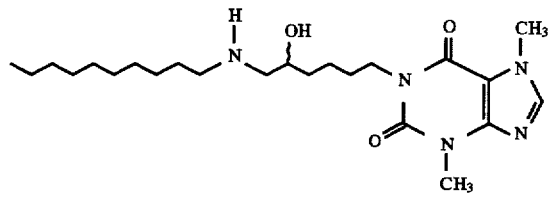
39  1-(6-Dodecylamino-5-hydroxyhexyl)-3,7-dimethylxanthine
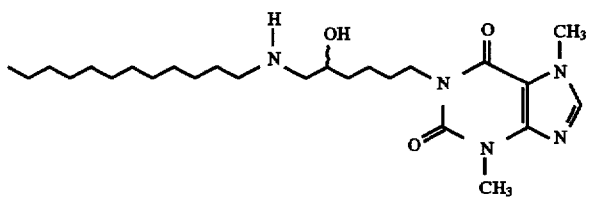
40  1-(11-Benzylamino-10-hydroxyundecyl-3,7-dimethylxanthine
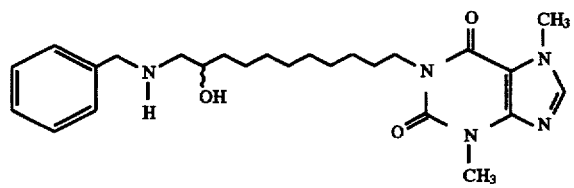
41  1-(9-Decylamino-8-hydroxynonyl)-3,7-dimethylxanthine
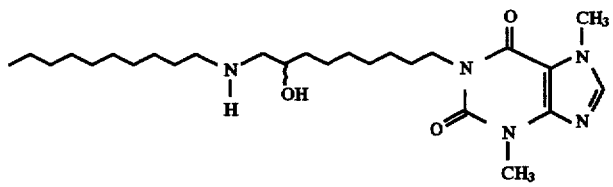
42  1-(9-Dodecylamino-8-hydrononyl)-3,7-dimethylxanthine
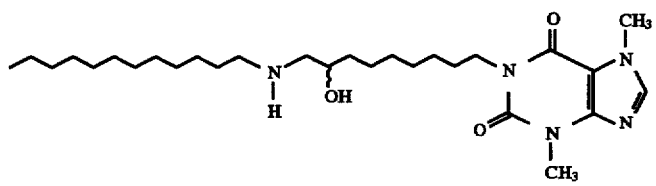
43  1-(9-Tetradecylamino-8-hydroxynonyl)-3,7-dimethylxanthine
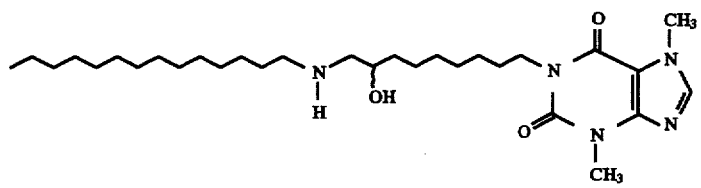
44  1-(11-Hexylamino-10-hydroxyundecyl)-3,7-dimethylxanthine
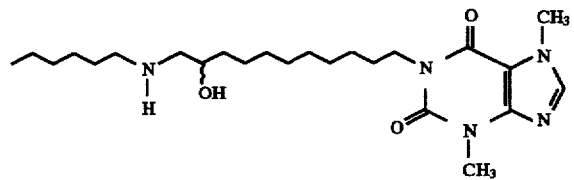

45  1-(11-Octylamino-10-hydroxyundecyl-3,7-dimethylxanthine
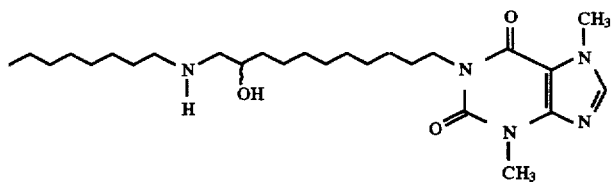
46  1-(6-Allylamino-5-hydroxyhexyl)-3,7-dimethylxanthine
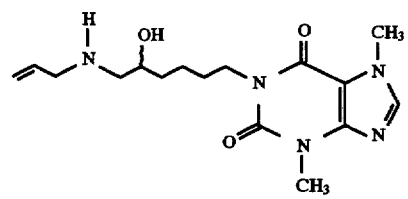
47  1-(11-Allylamino-10-hydroxyundecyl)-3,7-dimethylxanthine
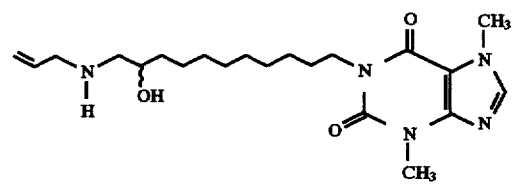
48  1-(6-N-Methyloctadecylamino-5-hydroxyhexyl)-3,7-dimethylxanthine
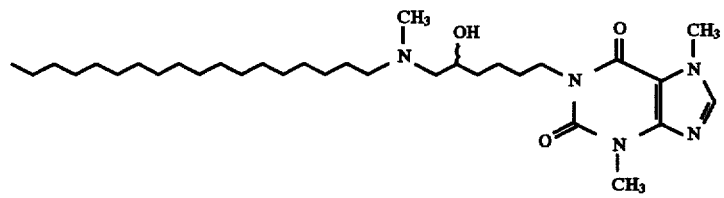
49  1-(11-Decylamino-10-hydroxyundecyl)-3,7-dimethylxanthine
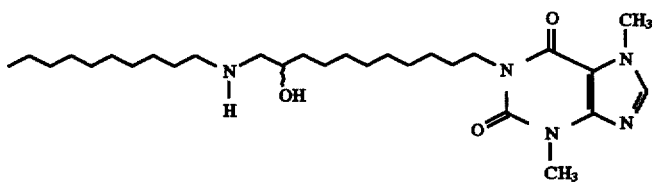
50  1-(11-Dodecylamino-10-hydroxyundecyl)-3,7-dimethylxanthine
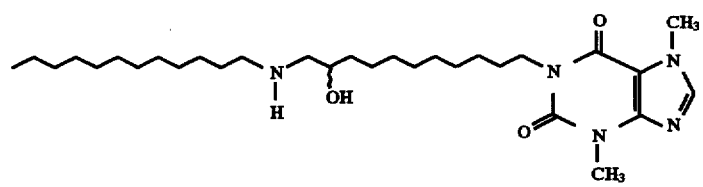
51  1-(11-Tetradecylamino-10-hydroxyundecyl)-3,7-dimethylxanthine
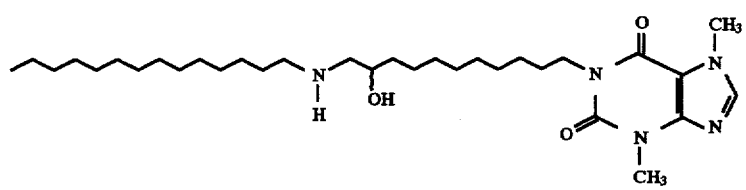

52  1-[11-(4-Fluorobenzylamino)-10-hydroxyundecyl]-3,7-dimethylxanthine

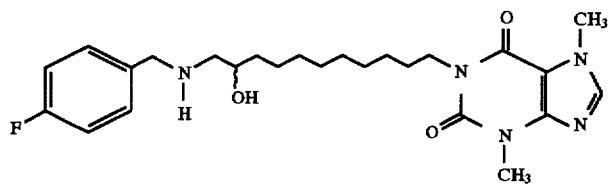

53  1-[11-(4-Trifluoromethylbenzylamino)-10-hydroxyundecyl]3,7-dimethylxanthine

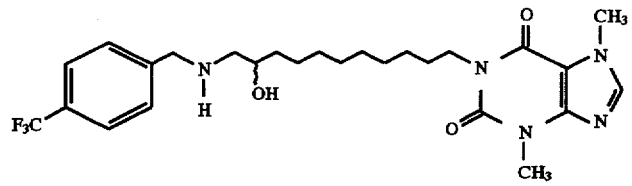

54  1-[11-(3-Diethylaminopropylamino)-10-hydroxyundecyl]-3,7-dimethylxanthine

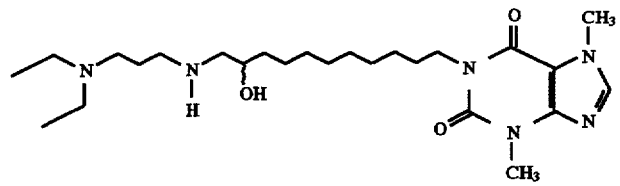

55  N,N'-bis[(10-yl-9-hydroxydecyl)-3,7-dimethylxanthine]diaminododecane

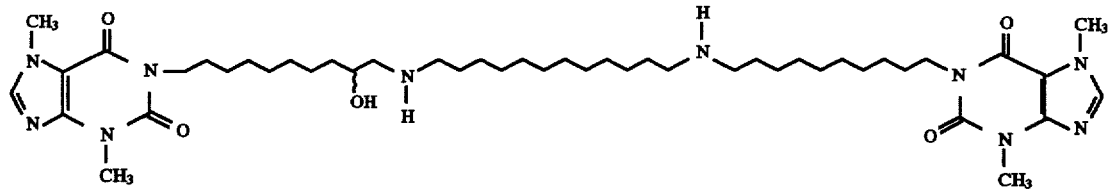

56  1-(14-Bromo-13-hydroxytetradecyl)-3,7-dimethylxanthine

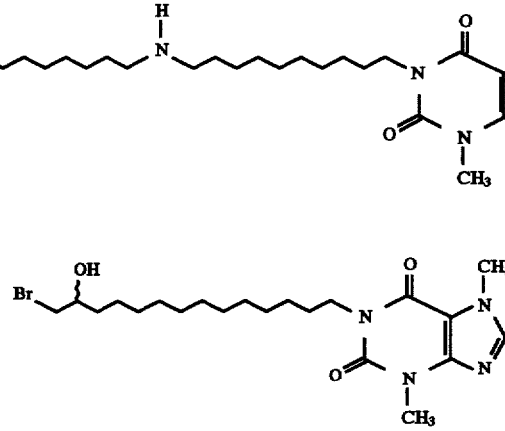

57  1-[11-(4-Aminobenzylamino)-10-hydroxyundecyl]-3,7-dimethylxanthine

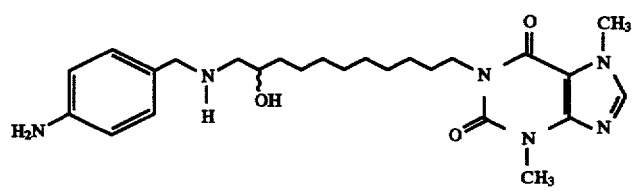

58  1-[11-(3,4,5-Trimethoxybenzylamino)-10-hydroxyundecyl]-3,7-dimethylxanthine

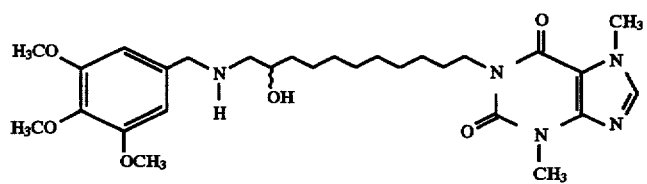

59  1-[11-(3-Butoxypropylamino)10-hydroxyundecyl}3,7-dimethylxanthine

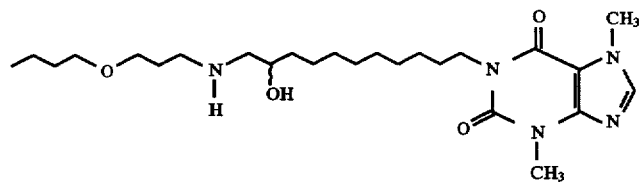

60  1-(14-Octylamino-13-hydroxytetradecyl]-3,7-dimethylxanthine

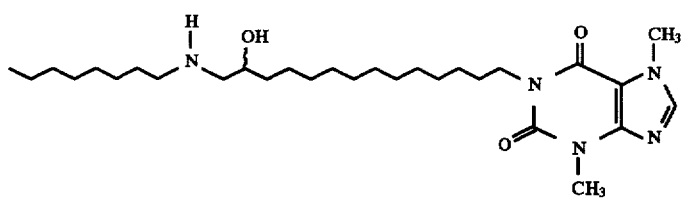

61  1-(11-Propylamino-10-hydroxyundecyl)-3,7-dimethylxanthine

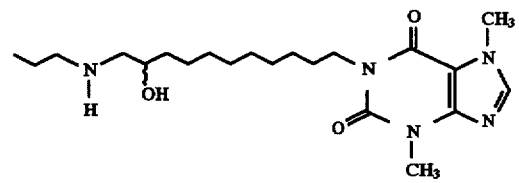

62  1-(11-Undecylamino-10-hydroxyundecyl-3,7-dimethylxanthine

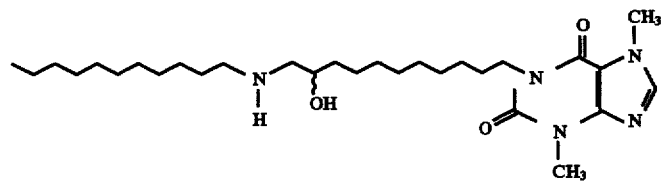

63  1-(11-Phenylamino-10-hydroxyundecyl]-3,7-dimethylxanthine

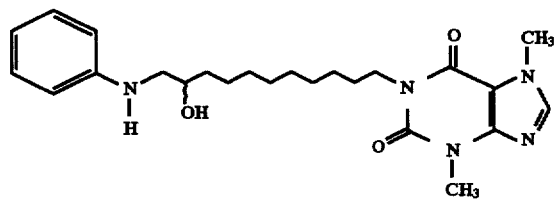

64  N,N-bis[11-yl-10-hydroxyundecyl)-3,7-dimethylxanthine]undecylamine

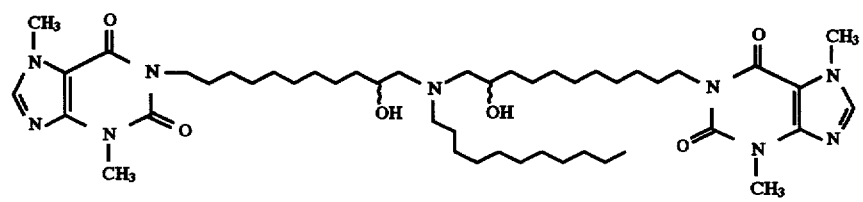

65  1-(11-Octadecylamino-10-hydroxyundecyl)-3,7-dimethylxanthine

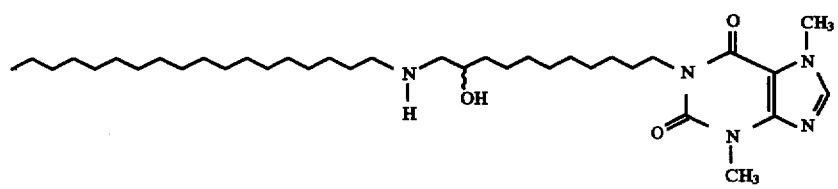

66  1-[9-N-Methyloctylamino-8-hydroxynonyl)]-3,7-dimethylxanthine

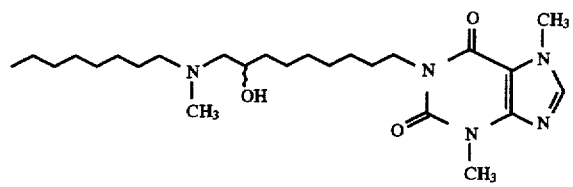

67  1-(4-Tetradecylamino-3-hydroxybutyl)-3,7-dimethylxanthine

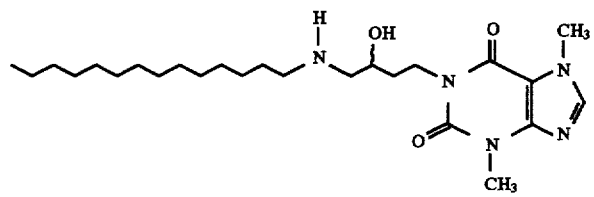

68  1-[9-(2-Hydroxydecyl-1-amino)nonyl]-3,7-dimethylxanthine

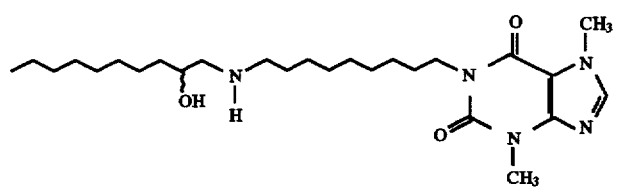

69  1-(6-Octadecylamino-5-hydroxyhexyl)-3,7-dimethylxanthine

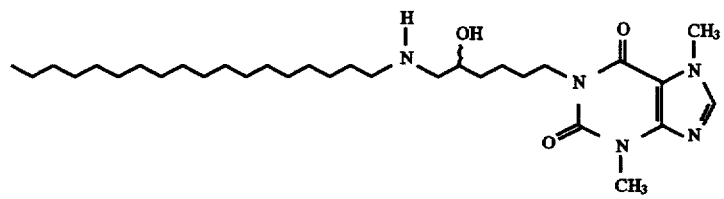

70  1-[11-(N-Octylacetamido)10-hydroxyundecyl]-3,7-dimethylxanthine

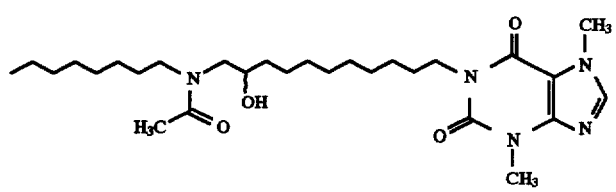

73  2-(11-Octylamino-10-hydroxyundecyl)-N-methylbenzamide

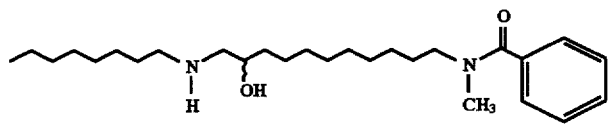

74  1-[11-(N-Methyl-N-octylamino)-10-hydroxyundecyl]-3,7-dimethylxanthine

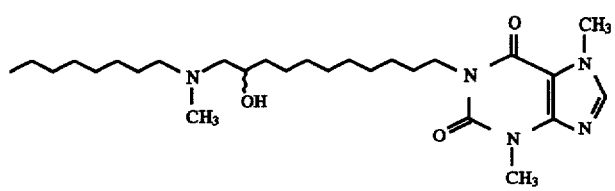

Uses of the Invention Compounds and Pharmaceutical Formulations

The inventive compounds provide a method for maintaining homeostasis in cells contacted by primary stimuli by mitigating the effects of these primary stimuli on the secondary signaling pathways invoked within seconds of a primary stimulus. For example, administration of an inventive compound in vivo or ex vivo provides a method to modify cellular behavior, the method comprising contacting cells (in vivo or ex vivo), whose behavior is to be modified, with an effective amount of an inventive compound or a pharmaceutical composition thereof. The method is a method to: (1) inhibit proliferation of tumor cells; (2) suppress activation of T-cells by antigen or IL-2 stimulation; (3) suppress activation of monocyte/macrophage cells by endotoxin, TNF, IL-1 or GM-CSF stimulation; (4) suppress antibody production of B-cells in response to an antigen, IL-4 or CD40 ligand; (5) inhibit the proliferation of smooth muscle cells in response to growth factors capable of stimulating said proliferation; (6) lower systemic vascular resistance conferred by endothelial cells; (7) lower systemic vascular resistance induced by endothelial cells; (8) lower expression of adhesion molecules induced by enhancers thereof; (9) suppress the activation of T-cells and macrophages by HIV; (10) inhibit the proliferation of kidney mesangial cells in response to stimulation by IL-1 and/or MIP-1$\alpha$ and/or PDGF and/or FGF; (11) enhance the resistance of kidney glomerular or tubular cells to cyclosporin A or amphotericin B; (12) prevent the release of MIP-1$\alpha$ by IL-1, TNF, or endotoxin stimulated monocytes and macrophages; (13) prevent the release of platelet activating factor by IL-1, TNF, or endotoxin treated megakaryocytes, fibroblastic cells, and macrophages; (14) prevent the down-regulation of receptors for cytokines in TNF-treated hematopoietic progenitor cells; (15) suppress the production of metalloproteases in IL-1-stimulated or TNF-stimulated glomerular epithelial cells or synovial cells; (16) enhance the resistance of gastrointestinal or pulmonary epithelial cells to cytotoxic drugs or radiation; (17) enhance the antitumor effect of a nonalkylating antitumor agent; (18) to inhibit the production of osteoclast activating factor in response to IL-1; (19) inhibit degranulation in response to IgE; (20) enhance the release of adrenergic neural transmitters, dopamine, norepinephrine, or epinephrine, or the neurotransmitter, acetylcholine; (21) modulate the post-synaptic "slow current" effects of the adrenergic neurotransmitters dopamine, epinephrine, or norepinephrine, or the neurotransmitter acetylcholine; (22) suppress signaling by neurotransmitters including acetyl choline, leuenkephalin and serotonin; or (23) increase seizure theshold.

Indications useful for administering compounds of the invention include, but are not limited to: the presence of a tumor burden, a hormone-related disorder, a neurological disorder, an autoimmune disease, inflammation, restenosis, coronary artery disease, atherosclerosis, hypertension, unwanted immune response (such as allograft reactions), viral infection, nephritis, mucositis, and various allergic responses. Allergic responses include acute allergic response and thus rhinorrhea, sinus drainage, diffuse tissue edema, and generalized pruritus. As well as the following, other chronic allergic responses include, dizziness, diarrhea, tissue hyperemia, and lacrimal swelling with localized lymphocyte infiltration. Allergic reactions are also associated with leukotriene release and the distal effects thereof, including asthmatic symptoms (e.g., development of airway obstruction, a decrease in FEV1, changes in vital capacity, and extensive mucus production).

Other suitable subjects for the administration of compounds of the invention, include patients: being administered other cytotoxic agents for the treatment of tumors, such as chemotherapeutic agents or irradiation therapy; suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; exhibiting unwanted smooth muscle cell proliferation in the form of, for example, restenosis, such as patients undergoing cardiac surgery; afflicted with autoimmune diseases, thus requiring deactivation of T and B cells, and having neurological disorders.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure theshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous sublethal dose of about 50 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to inhibition of a degradation pathway for the compounds of the invention; in particular, dealkylation at the N7 position of the xanthine ring. For example, NIH3T3-D5C3 cells can be used to compare effects of an inventive compound alone or in combination with a P-450 inhibitor by comparing transformation phenotype control, incubation with an inventive compound alone, and coincubation of an inventive compound with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60-100); cimetidine (400-2,400); ciprofloxacin (500-2000), enoxacin (500-2,000), norfloxacin (500-2000), ofloxacin (500-2,000), pefloxacin (500-2,000); erythromycin (100-1,000), troleandomycin (100-1,000); ketoconizole (100-2,000), thiabenzadole (100-1,000); isoniazid (100-1000); mexiletine (100-1,000); and dexamethasone (1-100 mg).

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier, optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen or oral administration is suitably from about 0.1 mg/kg to about 1000 mg/kg per day. For administration the dosage is suitably from about 0.001 mg/kg to about 40 mg/kg of the inventive compound or a pharmaceutically acceptable salt thereof, calculated as the free base. The active ingredient may be administered from 1 to 6 times a day, sufficient to exhibit activity.

The inventive compounds may be administered by inhalation (e.g., intranasal or oral) Appropriate dosage forms include an aerosol or a metered dose inhaler, as prepared by conventional techniques. The daily dosage is suitably from about 0.001 mg/kg to about 40 mg/kg of the inventive compound or a pharmaceutically acceptable salt thereof, calculated as the free base. Typical compounds for inhalation are in the form of a solution, suspension or emulsion that may be administered as a dry powder or in the form of an aerosol using a conventional propellant.

The invention is illustrated by the following examples which should not be regarded as limiting the invention in any way.

EXAMPLE 1

This example illustrates the synthesis of several compounds that are used as intermediates for the synthesis of other compounds.

1-(8,9-Oxidononyl)-3,7-dimethylxanthine was synthesized as follows: A mixture of theobromine (17.64 g, 98 mmol) and sodium hydride (2.35 g, 98 mmol) in dimethylsulfoxide (250 ml) was stirred for 15 minutes. 9-Bromo-1-nonene (20.0 g, 98 mmol) was added, and stirring was continued for 3 days. The reaction mixture was poured into water (300 ml) and extracted with dichloromethane (4×200 ml). The combined organic layers were washed with saturated aqueous sodium chloride solution (2×150 ml), dried over sodium sulfate, and the solvents were evaporated under vacuum. The residue was crystallized (dichloromethane-ether) to give 1-(8-nonenyl)-3,7-dimethylxanthine (24.34 g, 99% yield) as white crystals.

A solution of 1-(8-nonenyl)-3,7-dimethylxanthine (810 mg, 2.7 mmol), 4-methylmorpholine-N-oxide (340 mg, 2.9 mmol) and 2.5% osmium tetroxide in t-butanol (3 drops) in acetone (20 ml) and water (20 ml) was stirred for 24 hours. Saturated aqueous sodium dithionite solution (5 ml) was added. After stirring for 15 minutes, the reaction was extracted with 25% ethanol-dichloromethane (4×50 ml). The combined organic phases were dried over sodium sulfate and the solvents evaporated under vacuum. The solid residue was recrystallized (ethanol-chloroform) to give 1-(8, 9-Dihydroxynonyl)-3,7-dimethylxanthine (490 mg, 54% yield).

A mixture of 1-(8,9-dihydroxynonyl)-3,7-dimethylxanthine (428 mg, 1.3 mmol) and 30% hydrogen bromide in acetic acid (0.8 ml, 3.9 mmol) was stirred for 90 minutes. The solution was poured into a mixture of water (10 ml), sodium bicarbonate (1.35 g), and dichloromethane (10 ml). After 10 minutes of vigorous stirring the layers were separated and the aqueous portion was extracted with dichloromethane (3×15 ml). The combined organic phases were dried over sodium sulfate and the solvent was evaporated under vacuum to give 1(8-acetoxy-9-bromononyl)-3, 7-dimethylxanthine (550 mg, 96% yield) as a yellow oil. Without further purification, the oil was dissolved in methanol (5 ml) and then a 1M solution of sodium methoxide in methanol (1.4 ml) was added. After 30 minutes the reaction mixture was poured into water (30 ml) and extracted with dichloromethane (3×40 ml). The combined organic phases were dried over sodium sulfate and the solvents evaporated under vacuum. The solid residue was recrystallized (dichloromethane-petroleum ether) to give 1-(8,9-oxidononyl)-3,7-dimethylxanthine (380 mg, 91% yield).

1-(5,6-Oxidohexyl)-3,7-dimethylxanthine was synthesized as follows: A mixture of 1-bromohexene (10.7 g, 66 mmol), sodium hydride (1.58 g, 66 mmol), and theobromine (11.9 g, 66 mmol) in dimethylsulfoxide (100 ml) was stirred for 43 hours. The solution was treated with water (200 ml) and then extracted with dichloromethane (3×80 mL). The combined extracts were washed with water (3×100 ml), dried over magnesium sulfate, and then the solvent was evaporated under vacuum to give 1-(5-hexenyl)-3,7-dimethylxanthine (17 g, 98% yield) as a white powder.

To 1-(5-hexenyl)-3,7-dimethylxanthine (1.07 g, 4.1 mmol) and 4-methylmorpholine-N-oxide (1.44 g, 12.3 mmol) in water (20 ml) and acetone (10 ml) was added 2.5% solution of osmium tetraoxide in t-butanol (6 drops). After stirring for 48 hours, the mixture was treated with 20% aqueous sodium dithionite solution (20 ml). After 2 minutes, the mixture was extracted with 25% ethanol-dichloromethane (3×30 ml). The combined extracts were dried over magnesium sulfate and the solvents were evaporated under vacuum to give 1-(5,6-dihydroxyhexyl)-3,7-dimethylxanthine (750 mg, 62% yield) as a white powder.

To 1-(5,6-dihydroxyhexyl)-3,7-dimethylxanthine (1.0 g, 3.38 mmol) was added 30% hydrogen bromide-acetic acid (3.4 mL) over 30 seconds and then stirred until all of the solid had dissolved (2.5 hours). The solution was poured carefully over a mixture of sodium bicarbonate (12 g) and ice water (50 ml). After carbon dioxide evolution had subsided, the mixture was extracted with dichloromethane (3×25 ml). The combined extracts were dried over magnesium sulfate and the solvent was evaporated under vacuum to give 1-(5-acetoxy-6-bromohexyl)-3,7-dimethylxanthine (1.3 g, 96% yield) as a viscous oil which was dissolved in methanol (5 mL). A 1M solution of sodium methoxide in methanol (3.9 ml) was added over 30 seconds. After stirring for 20 minutes, the solution was treated with water (20 ml) and then extracted with dichloromethane (3×15 ml). The combined extracts were dried over magnesium sulfate and the solvents were evaporated under vacuum to give 1-(5,6-oxidohexyl)-3,7-dimethylxanthine (900 mg, 100% yield) as white crystals.

3-(5,6-Oxidohexyl)-1-methyluracil was synthesized as follows: A mixture of sodium hydride (86 mg, 3.6 mmol) and 1-methyluracil (500 mg, 4 mmol) in dimethyl sulfoxide (25 ml) was stirred for 15 minutes, and then 6-bromo-1-hexene (647 mg, 4 mmol) was added. After stirring for 20 hours, the reaction mixture was poured into water (50 ml) and extracted with 20% ethanol-dichloromethane (3×50 ml). The combined organic layers were washed with saturated aqueous sodium chloride solution (20 ml) and dried over sodium sulfate. The solvent was evaporated under vacuum to give a residue which was purified by column chromatography (silica, ethyl acetate) to give 3-(5-hexenyl)-1-methyluracil (598 mg, 72% yield).

A solution of 3-(5-hexenyl)-1-methyluracil (598 mg, 2.9 mmol), 4-methylmorpholine-N oxide (408 mg, 3.5 mmol), and a 2.5% solution of osmium tetroxide in t-butanol (3 drops) in acetone (15 ml) and water (5 ml) was stirred for 3 days. Saturated aqueous sodium hydrosulfite solution (10 ml) was added and the mixture was stirred for 15 minutes. Water (50 ml) was added and the mixture was extracted with 20% ethanol-dichloromethane (4×40 ml). The combined organic layers were dried over sodium sulfate and the solvents were evaporated under vacuum to give 3-(5,6-dihydroxyhexyl)-1-methyluracil (461 mg, 66% yield) as a colorless oil.

3-(5,6-Dihydroxyhexyl)-1-methyluracil (350 mg, 1.4 mmol) was stirred with 30% hydrogen bromide in acetic acid (0.87 ml, 4.3 mmol) for 45 minutes. The solution was added to a mixture of sodium bicarbonate (1.6 g), water (10 ml) and dichloromethane (20 ml). After 15 minutes of vigorous stirring, the layers were separated and the aqueous layer was extracted with dichloromethane (3×40 ml). The combined organic layers were dried over sodium sulfate and the solvent was evaporated under vacuum to give 3-(5-acetoxy-6-bromohexyl)-1-methyluracil (500 mg, 100% yield). The bromoacetate thus obtained was used in the next step without further purification. 3-(5-Acetoxy-6-bromohexyl)-1-methyluracil (360 mg, 1.0 mmol) was dissolved in methanol (5 ml) and treated with a solution of 1M sodium methoxide in methanol (1 ml). After stirring for 15 min, the solution was poured into water (10 ml) and extracted with dichloromethane (3×30 ml). The combined organic layers were dried over sodium sulfate and the solvents were evaporated to give 3-(5,6-oxidohexyl)-1-methyluracil (150 mg, 67% yield) as a colorless oil.

3-(5,6-Oxidohexyl)-1-methylthymine was synthesized as follows: A mixture of sodium hydride (343 mg, 14 mmol) and 1-methylthymine (2.00 g, 14 mmol) in dimethylsulfoxide (30 ml) was stirred for 15 minutes, and then 6-bromo-1-hexene (2.30 g, 14 mmol) was added. After stirring for 69 hours, the reaction mixture was poured into water (100 ml) and extracted with dichloromethane (4×50 ml). The combined organic layers were washed with saturated aqueous sodium chloride solution (40 ml), dried over sodium sulfate, and then the solvent was evaporated under vacuum to give a residue which was recrystallized (dichloromethane-ethyl ether) to give 3-(5-hexenyl)-1-methylthymine (2.80 g, 88% yield).

A solution of 3-(5-hexenyl)-1-methylthymine (2.00 g, 9 mmol), 4-methylmorpholine-N-oxide (1.17 mg, 10 mmol), and osmium tetroxide (0.15 ml of a 2.5% solution in t-butanol) in acetone (15 ml) and water (10 ml) was stirred for 20 hours. Saturated aqueous sodium hydrosulfite solution (10 ml) was added and after 15 minutes of stirring, the mixture was extracted with 20% ethanol-dichloromethane (4×40 ml). The combined organic layers were dried over sodium sulfate and the solvents were evaporated under vacuum to give a solid residue. The solid was recrystallized (ethanol) to give 3-(5,6-dihydroxyhexyl)-1-methylthymine (2.00 g, 89% yield).

3-(5,6-Dihydroxyhexyl)-1-methylthymine (1.65 g, 6.4 mmol) was stirred with 30% hydrogen bromide in acetic acid (3.8 ml, 19.3 mmol) for 1.5 hours. The mixture was then added to a mixture of sodium bicarbonate (6.7 g), water (40 ml), and dichloromethane (50 ml). After 15 minutes of vigorous stirring, the layers were separated and the aqueous layer was extracted with dichloromethane (2×50 ml). The combined organic layers were dried over sodium sulfate and the solvent was evaporated under vacuum to give 3-(5-acetoxy-6-bromohexyl)-1-methylthymine (2.30 g, 100% yield). The bromoacetate was used in the next step without further purification. 3-(5-Acetoxy-6-bromohexyl)-1-methylthymine (2.30 g, 6.4 mmol) was dissolved in methanol (10 ml) and a solution of 1M sodium methoxide in methanol (7 ml) was added. After stirring for 15 minutes, the solution was poured into water (60 ml) and extracted with 20% ethanol-dichloromethane (2×70 ml). The combined organic layers were dried over sodium sulfate and the solvents were evaporated under vacuum to give 3-(5,6-oxidohexyl)-1-methylthymine (1.30 g, 85% yield) as a white solid.

3-(5,6-Oxidohexyl)-1-methylbenzoyleneurea was synthesized as follows: A solution of sodium hydride (0.76 g, 30 mmol) and benzoyleneurea (4.86 g, 30 mmol) in dimethylsulfoxide (100 ml) was stirred for 10 minutes and then methyl iodide (1.87 ml, 30 mmol) was added. After stirring for 14 hours, water (100 ml) was added and the solution was extracted with dichloromethane (3×100 ml). The mixture was filtered and the dichloromethane phase was dried over sodium sulfate. After evaporation of the solvent under vacuum, the residue was recrystallized (dichloromethane) to give 1-methylbenzoyleneurea (1.3 g, 25% yield) as a white solid.

A solution of sodium hydride (0.17 g, 6.8 mmol) and I-methylbenzoyleneurea (1.07 g, 6.1 mmol) in dimethyl sulfoxide (50 ml)was stirred for 10 minutes and then 1-bromohexene (0.82 ml, 6.8 mmol) was added. After 14 hours, water (50 ml) was added and the solution was extracted with dichloromethane (3×30 ml). The combined organic phases were washed with water (3×50 ml), dried over sodium sulfate, and the solvent was evaporated under vacuum to give 3-(5-hexenyl)-1-methylbenzoyleneurea (1.51 g, 96 %) as a white solid.

A solution of 3-(5-hexenyl)-1-methylbenzoyleneurea (1.5 g, 5.8 mmol), 4-methylmorphline-N-oxide (0.87 g, 7.4 mmol), and potassium osmate(IV) dihydrate (0.021 g, 0.1 mmol) in acetone (12.5 ml) and water (4 ml) was stirred. After 18 hours, a 20% aqueous solution hydrosulfite (20 ml) was added and stirred for 30 minutes. The solution was extracted with dichloromethane (3×75 ml). The combined organic phases were dried over sodium sulfate and the solvent was evaporated under vacuum. The residue was purified by flash chromatography (silica, 5% methanol-dichloromethane) to give 3-(5,6-dihydroxyhexyl)-1-methylbenzoyleneurea (1.59 g, 94%) as a white solid.

A mixture of 3-(5,6-dihydroxyhexyl)-1-methylbenzoyleneurea (0.92 g, 3.1 mmol) in 30% hydrogen bromide in acetic acid (0.63 ml, 9.3 mmol) was stirred for 90 minutes. The reaction mixture was poured into a mixture of sodium bicarbonate (0.78 g, 9.3 mmol), water (20 ml), and dichloromethane (20 ml). The phases were separated and the aqueous phase was extracted with dichloromethane (2×20 ml). The combined organic phases were washed with brine (20 ml), dried over sodium sulfate, and the solvent was evaporated under vacuum to give 3-(5-acetoxy-6-bromohexyl)-1-methylbenzoyleneurea (1.2 g, 96%).

To a 1M solution of sodium methoxide in methanol (3.1 ml) was added 1-(5-acetoxy-6-bromohexyl)-3-methylbenzoyleneurea (1.17 g, 2.9 mmol) in methanol (25 ml) over 5 minutes. After stirring for 1 hour, water (50 ml) was added. The solution was extracted with dichloromethane (3×25 ml). The combined organic phases were dried over sodium sulfate and the solvents were evaporated under vacuum to give 3-(5,6-oxidohexyl)-1-methylbenzoyleneurea (0.77 g, 97%) as a white solid.

1-(5,6-Oxidohexyl)glutarimide was synthesized as follows: A mixture of glutarimide (2.00 g, 7.7 mmol) and sodium hydride (425 mg, 17.7 mmol) in dimethyl sulfoxide (40 ml) was stirred for 20 minutes and then 6-bromo-1-hexene (2.90 g, 17.7 mmol) was added. After 20 hours of stirring, the reaction was poured into water (100 ml) and extracted with dichloromethane (4×50 ml). The combined organic layers were washed with water (50 ml) and then with saturated aqueous sodium chloride solution (50 ml). After drying over sodium sulfate the solvent was evaporated under vacuum to give 1-(5-hexenyl)glutarimide (2.92 g, 85% yield).

To a solution of 1-(5-hexenyl)glutarimide (630 mg, 3.2 mmol) in dichloromethane (10 ml) was added sodium bicarbonate (2.20 g, 26 mmol) in water (10 ml) by 50% m-chloroperoxybenzoic acid (2.5 g, 7.2 mmol). After stirring for 17 hours, sodium metabisulfite (1.7 g, 9.0 mmol) was added and stirred for 30 minutes. The mixture was extracted with dichloromethane (3×10 ml) and then the combined organic layers were washed with saturated aqueous sodium bicarbonate solution (10 ml). After drying over sodium sulfate and evaporation of the solvent under vacuum, the residue was purified by column chromatography (silica, 10% ethanol-dichloromethane) to give 1-(5,6-oxidohexyl)glutarimide (180 mg, 27% yield).

EXAMPLE 2

This example illustrates a method for synthesis of 1-(8-hydroxy-9-(N-benzyl)aminononyl)-3,7-dimethylxanthine (compound no. 27). A mixture of 1-(8,9-oxidohexyl)-3,7-dimethylxanthine (500 mg, 1.6 mmol) from Example 1 and benzylamine (2.0 g, 19 mmol) was heated at 150° C. for 4 hours. After cooling to ambient temperature, ether (30 ml) was added. The precipitate was washed with cold ether to give (compound no. 27) (278 mg, 41% yield).

EXAMPLE 3

This example illustrates the synthesis of 1-(5-hydroxy-6-(N-octyl)aminohexyl)-3,7-dimethylxanthine (compound no. 28). A mixture of 1-(5,6-oxidohexyl)-3,7-dimethylxanthine (400 mg, 1.4 mmol) synthesized in example 1 and 1-octylamine (391 mg, 3 mmol) was heated at 135° C. for 4 hours. After cooling to ambient temperature, ether (15 ml) was added. The precipitate was washed several times with hexane to give compound no. 28 (537 mg, 94% yield).

EXAMPLE 4

This example illustrates the synthesis of 1-(5-hydroxy-6-(N-(4-phenyl)butyl)amino)hexyl)-3,7-dimethylxanthine (compound no. 29). A mixture of 1-(5,6-oxidohexyl)-3,7-dimethylxanthine (300 mg, 1.1 mmol) from example 1 and 4-phenyl-1-butylamine (322 mg, 2.2 mmol) was heated at 130° C. for 70 minutes. After cooling to ambient temperature, the residue was dissolved in dichloromethane (2 ml) and added to ether (20 ml). The precipitate was washed several times with hexane to give compound no. 29 (280 mg, 60% yield).

EXAMPLE 5

This example illustrates the synthesis of 1-(5-hydroxy-6-(N-undecyl)aminohexyl)-3,7-dimethylxanthine (compound no. 30). A mixture of 1-(5,6-oxidohexyl)-3,7-dimethylxanthine (300 mg, 1.1 mmol) from example 1 and 1-undecylamine (754 mg, 4.4 mmol) was heated at 100° C. for 4 hours and then at 130° C. for 1 hour. After cooling to ambient temperature, ether (10 ml) was added. The waxy precipitate was washed several times with hexane to give compound no. 30 (403 mg, 82% yield).

EXAMPLE 6

This example illustrates the synthesis of 1-(5-hydroxy-6-(N-cyclohexylmethyl)aminohexyl)-3,7-dimethylxanthine (compound no. 31). A mixture of 1-(5,6-oxidohexyl)-3,7-dimethylxanthine (300 mg, 1.1 mmol) from example 1 and cyclohexanemethylamine (249 mg, 2.2 mmol) was heated at 100° C. for 5 hours and then at 120° C. for 1 hour. After cooling to ambient temperature, ether (7 ml) and hexane (10 ml) were added. The precipitate was washed several times with hexane to give compound no. 31 (294 mg, 68% yield).

EXAMPLE 7

This example illustrates the synthesis of 1-(5-hydroxy-6-(N-(6-hydroxy)hexylaminohexyl)-3,7-dimethylxanthine (compound no. 32). A mixture of 1-(5,6-oxidohexyl)-3,7-dimethylxanthine (300 mg, 1.1 mmol) from example 1 and 6-amino-1-hexanol (754 mg, 2.6 mmol) was heated at 120° C. for 2 hours. After cooling to ambient temperature, ether (20 ml) was added. The precipitate was washed several times with hexane to give compound no. 32 (321 mg, 74% yield).

EXAMPLE 8

This example illustrates the synthesis of 1-(5-hydroxy-6-(N,N-dihexyl)aminohexyl)-3,7-dimethylxanthine (compound no. 33). A mixture of 1-(5,6-oxidohexyl)-3,7-dimethylxanthine (300 mg, 1.1 mmol) from example 1 and dihexylamine (556 mg, 3.0 mmol) was heated at 135° C. for 5 hours and then at 170° C. for 2 hours. After cooling to ambient temperature, petroleum ether (20 ml) was added. After cooling in a freezer, the precipitate was washed several times with petroleum ether to give compound no. 33 (263 mg, 52% yield).

EXAMPLE 9

This example illustrates the synthesis of 1-(5-hydroxy-6-(N-(4-methoxy)benzyl)aminohexyl)-3,7-dimethylxanthine (compound no. 34). A mixture of 1-(5,6-oxidohexyl)-3,7-dimethylxanthine (300 mg, 1.1 mmol) from example 1 and 4-methoxybenzylamine (0.7 g, 5 mmol) was heated at 100° C. for 4 hours. After cooling to ambient temperature, ether (10 ml) was added. The precipitate was washed several times with petroleum ether to give compound no. 34 (355 mg, 78% yield).

EXAMPLE 10

This example illustrates the synthesis of 3-(5-hydroxy-6-(N-propyl)aminohexyl)-1-methyuracil (compound no. 19). A mixture of 3-(5,6-oxidohexyl)-1-methyluracil (100 mg, 0.4 mmol) from example 1 and n-propylamine (10 ml) was heated in a sealed pressure bottle at 80°–90° C. for 69 hours. Evaporation of the unreacted n-propylamine gave a yellow oil which was crystallized (ether-dichloromethane) to give compound no. 19 (80 mg, 71%) as a white solid.

EXAMPLE 11

This example illustrates the synthesis of 3-(5-hydroxy-6-(N-benzyl)aminohexyl)-1-methylbenzoyleneurea (compound no. 3). A mixture of 3-(5,6-oxidohexyl)-1-methylbenzoyleneurea (0.1 g, 0.4 mmol) from example 1 and benzylamine (0.13 g, 1.2 mmol) was stirred under argon at 115° C. After 3 hours, the unreacted benzylamine was evaporated under vacuum. The residue crystallized on standing to give (compound no. 3) (0.14 g, 93% yield) as a white solid.

EXAMPLE 12

This example illustrates the synthesis of 1-(5-hydroxy-6-(N-propyl)aminohexyl)-3,7-dimethylxanthine (compound no. 14). A solution of 1-(5,6-oxohexyl)-3,7-dimethylxanthine (238 mg, 0.86 mmol) from example 1 in n-propylamine (5 ml) was heated at 100° C. in a sealed pressure bottle for 23 hours. After cooling to 4° C., the bottle was unsealed and unreacted n-propylamine was evaporated under vacuum to give (compound no. 14) (190 mg, 64% yield) as a viscous oil.

EXAMPLE 13

This example illustrates the synthesis of 1-(5-hydroxy-6-(N-benzyl)aminohexyl)-3,7-dimethylxanthine (compound no. 13). A mixture of (5,6-oxidohexyl)-3,7-dimethylxanthine (500 mg, 1.8 mmol) from example 1 and benzylamine (1.7 g, 15.8 mmol) was heated at 150° C. for 4 hours. After cooling to ambient temperature, ether was added (20 ml). The precipitate was washed with cold ether to give compound no. 13 (470 mg, 70% yield).

EXAMPLE 14

This example illustrates the synthesis of 3-(5-hydroxy-6-(N-undecyl)aminohexyl)-1-methylthymine (compound no. 24). A mixture of 3-(5,6-oxidohexyl)-1-methylthymine from example 1 (250 mg, 1.1 mmol) and 1-undecylamine (0.7 ml) were heated at 110° C. for 4 hours. After cooling to ambient temperature, ether (5 ml) and petroleum ether (10 ml) were added. After cooling to −10° C. for 2 hours, the precipitate was washed several times with petroleum ether to give compound no. 24 (361 mg, 80% yield).

EXAMPLE 15

This example illustrates the synthesis of 3-(6-propylamino-5-hydroxyhexyl)-1-methylthymine (compound no. 26). A solution of 3-(5,6-oxidohexyl)-1-methylthymine (200 mg, 0.8 mmol) from example 1 in n-propylamine (10 ml) was heated in a sealed pressure bottle at 100°–105° C. for 24 hours. After evaporation of unreacted n-propylamine, the residue was crystallized (ether) to give compound no. 26 (162 mg, 68% yield).

EXAMPLE 16

This example illustrates the synthesis of 1-(8-hydroxy-9-(N-octyl)aminononyl)-3,7-dimethyl-xanthine (compound no. 35). A mixture of 1-(8,9-oxidohexyl)-3,7-dimethylxanthine 300 mg, 0.9 mmol) from example 1 and octylamine (1 ml) were heated at 110° C. for 3 hours. After cooling to room temperature, ether (10 ml) was added. The precipitate was washed several times with petroleum ether to give compound no. 35 (342 mg, 85% yield).

EXAMPLE 17

This example illustrates the synthesis of 1-(5-hydroxy-6-(N-tetradecyl)aminohexyl)-3,7-dimethylxanthine (compound no. 36). A mixture of 1-(5,6-oxohexyl)-3,7-dimethylxanthine (300 mg, 1.1 mmol) from example 1 and 1-tetracecylamine (604 mg, 2.8 mmol) was heated at 110° C. for 3 hours. After cooling to ambient temperature, ether (6 ml) was added. The precipitate was washed several times with petroleum ether to give compound no. 36 (356 mg, 66% yield).

EXAMPLE 18

This example illustrates a method of synthesis for 1-(9-Tetradecylamino-8-hydroxynonyl)-3,7-dimethylxanthine (compound no. 73). A mixture of 1-(8,9-oxidononyl)-3,7-dimethylxanthine (synthesized in example 1 above, 1.00 g, 3.1 mmol) and anhydrous lithium perchlorate (329 mg, 3.1 mmol) was stirred in anhydrous acetonitrile (30 mL). After addition of 1-tetradecylamine (Aldrich, 722 mg, 3.4 mmol), the mixture was stirred at 60° C. for 4 hours. After cooling, water (50 mL) was added and the mixture was extracted with dichloromethane (3×50 mL). The combined organic layers were washed with water (30 mL) and saturated aqueous salt solution (30 mL) and subsequently dried over sodium sulfate. The solvent was removed under vacuum to give a white residue. Chromatography (neutral activity II alumina, dichloromethan/5%methanol) of the white residue resulted in 860 mg of compound no. 73 (52% yield).

EXAMPLE 19

This example illustrates a method of synthesis for compound no. 63. Sodium hydride(95%) (1.26 g, 50 mmol) was added to a solution of theobromine (7.2 g, 40 mmol) in dimethylsulfoxide (300 mL). After 20 minutes of stirring, undecenylmesylate (7.95 g, 30 mmol) was added and stirred for 12 hours at room temperature. The reaction, warmed to 70°–80° C., was stirred for 4 hours. The reaction mixture was poured into a separatory funnel containing 1 L of water and extracted with dichloromethane (5×200 mL). The organic extracts were combined, washed with water (100 mL) and brine (100 mL), dried over anhydrous magnesium sulfate and concentrated under reduced pressure. A crude product obtained was further purified by flash chromatography over silica gel using an eluant of 20% hexane/dichloromethane to obtain 4.6 g of 1-10-undecenyl)-3,7-dimethylxanthine (yield, 46.3%).

A solution of 1-(10-undecenyl)-3,7-dimethylxanthine, prepared above (4.3 g, 13 mmol), 4-methylmorpholine-N-oxide (1.942 g, 16.6 mmol) and potassium osmate dihydrate (9.5 mg; 0.026 mmol) in acetone (45 mL) and water (10 mL) was stirred for 6 hours. A solution of 20% aqueous sodium sulphite (12 ml) was added and stirred for 30 minutes. The reaction mixture was extracted with 25% ethanol/dichloromethane (4×100 mL). The combined organic extracts were dried over anhydrous magnesium sulfate, concentrated under reduced pressure and purified by flash chromatography over silica gel using a methanol/5% dichloromethane eluent to obtain 3.6 g of 1-(10,11-dihydroxyundecanyl)-3,7-dimethylxanthine (yield, 76%).

1-(10,11-dihydroxyundecanyl)-3,7-dimethylxanthine, prepared above (3.6 g, 10 mmol), was stirred with hydrogen bromide (6.2 mL, 8.4 g of a 30% solution in acetic acid, 31.1 mmol) for 90 minutes. The mixture was then added to a flask containing 100 mL aqueous sodium bicarbonate solution and 75 mL dichloromethane. After 10 minutes of vigorous stirring, the layers were separated and an aqueous portion washed with dichloromethane (3×75 mL). The organic portions were combined, dried over magnesium sulfate, and evaporated to give 1-(10-acetoxy-11-bromoundecanyl)-3,7-dimethylxanthine (3.6 g). Without further purification, the bromoacetate was taken up in methanol (25 mL) and treated with a solution of sodium methoxide (prepared from 0.28 g, 12.2 mmol sodium, and 25 mL methanol). After 30 minutes, most of the solvent was removed under reduced pressure and the residue was extracted with dichloromethane (3×75 mL). The organic portions were combined, dried over magnesium sulfate and concentrated under reduced pressure to give an off-white solid, purified by column chromatography over silica gel using dichloromethane/3% methanol eluant to obtain 2.0 g of 1-(10,11-oxidoundecanyl)-3,7-dimethylxanthine (yield, 57.5%).

A mixture of 1-(10,11-oxidoundecyl)-3,7-dimethylxanthine, prepared above (500 mg, 1.4 mmol), and lithium perchlorate (from Aldrich, 149 mg, 1.4 mmol) was stirred in anhydrous acetonitrile (from Aldrich, 20 mL) until homogeneous. Aniline (from Aldrich, 670 mg, 7.2 mmol) was added, and the mixture stirred at stirred at ambient temperature for 16 hours, then at a reflux temperature for 3 hours. The residue was directly deposited on a silica column. Chromatography using a dichloromethane/10% methanol gradient produced 0.45 g of compound no. 63 (73% yield).

EXAMPLE 20

This example illustrates data of proliferative activity of various inventive compounds for inducing CMV promotor activity. The CMV promoter assay measures gene transcription and translation activity wherein any active compounds will have cytotoxic activity for inhibiting cellular protein synthesis in transformed (adenovirus) cells. Each compound was tested and the data is listed in Table I below. Compound no. 30 was the most cytotoxic compound tested.

TABLE I

| Compound | IC50 (µM) |
|---|---|
| 13 | >500 |
| 28 | 50 |
| 29 | >100 |
| 30 | 15 |
| 31 | >100 |
| 32 | >100 |
| 33 | 100 |
| 5 | >500 |
| 19 | >500 |
| 26 | >500 |

EXAMPLE 21

This example shows the effects of five inventive compounds on inhibition of mast cell degranulation by the serotonin release assay. This assay is described above and provides an in vitro model for an allergy and asthma therapeutic product. Table II below shows the results of five inventive compounds (see above for chemical names and structures).

TABLE II

| Compound | % Inhibition | Concentration (µM) |
|---|---|---|
| 13 | 28% | 100 |
| 27 | 29% | 50 |
| 30 | too toxic | 50 |
| 35 | too toxic | 50 |
| 19 | inactive | 50 |

EXAMPLE 22

Figure 1B:
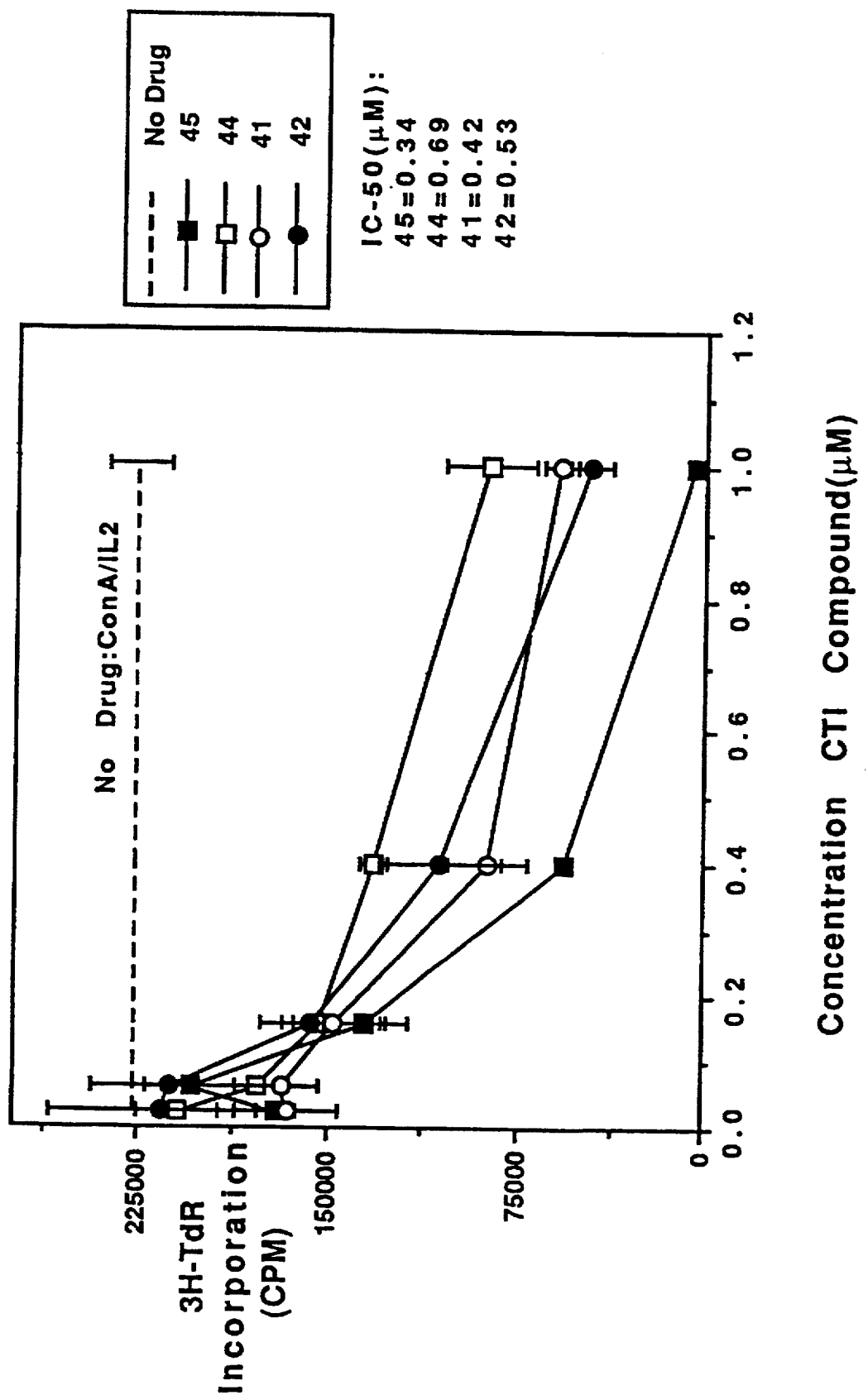

This example illustrates dose response curves used to generate 50% inhibition concentrations (IC50) of for both cyclosporin A (CsA, FIG. 1A) and various inventive compounds (FIG. 1B) for murine thymocyte proliferation, co-stimulated by Concanavalin A (ConA) and interleukin-2 alpha (IL-2). ConA, used to activate CD3, along with IL-2 co-stimulation, induces T-cell proliferation and differentiation. Thymuses, obtained from normal, female Balb/C mice, were dissociated and plated into 96-well plates at a density of 2×10⁵ cells/well. ConA (0.25 mg/ml) and IL-2 (15 U/ml) were added to the wells. The cells were incubated for 4 days at 37° C. On day 4, the cells were pulsed with tritiated thymidine and incubated for an additional 4 hours. The amount of tritiated thymidine dye incorporated by the harvested cells was determined in a liquid scintillation counter. Drug doses (shown in FIGS. 1A and 1B) were added two hours prior to ConA and IL-2 activation. Background counts were less than 200 cpm. Both CsA and the inventive compounds tested inhibit thymocyte proliferation and activation.

EXAMPLE 23

Figure 2A:
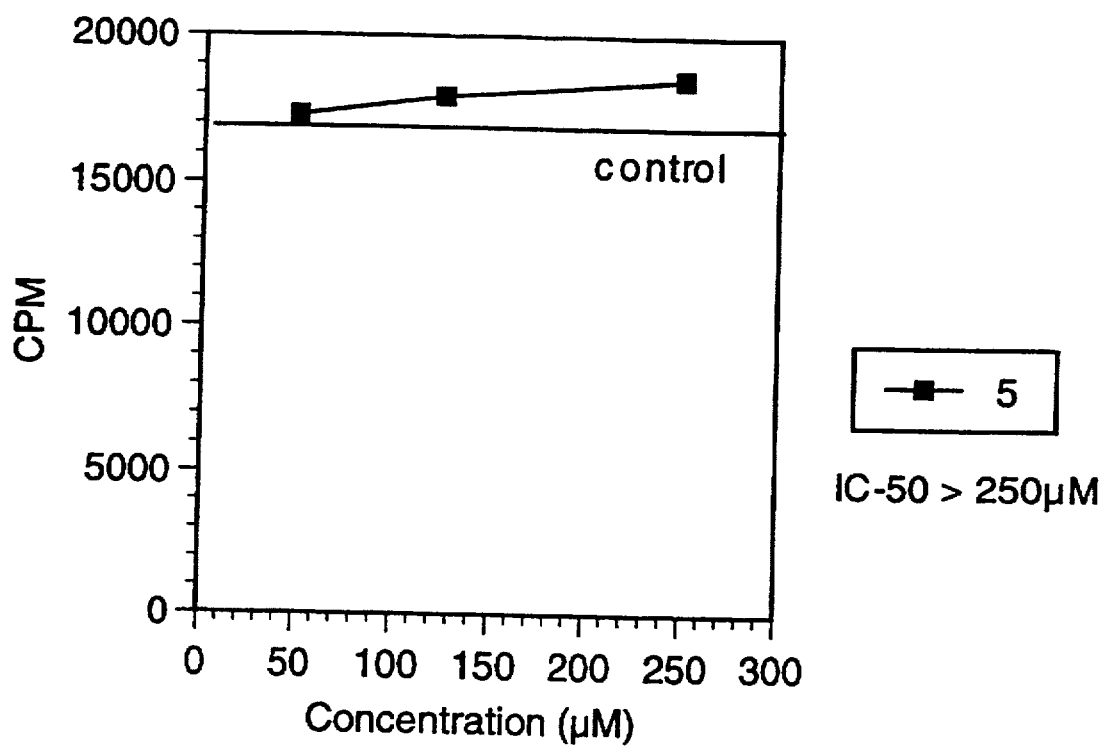
FIGS. 2A and 2B illustrate immune modulating activity of compounds nos. 5 and 26 (see corresponding names and structures below) in an assay determining proliferative PMBC response to allogeneic stimulation using a two-way, mixed lymphocyte reaction.
Figure 2B:
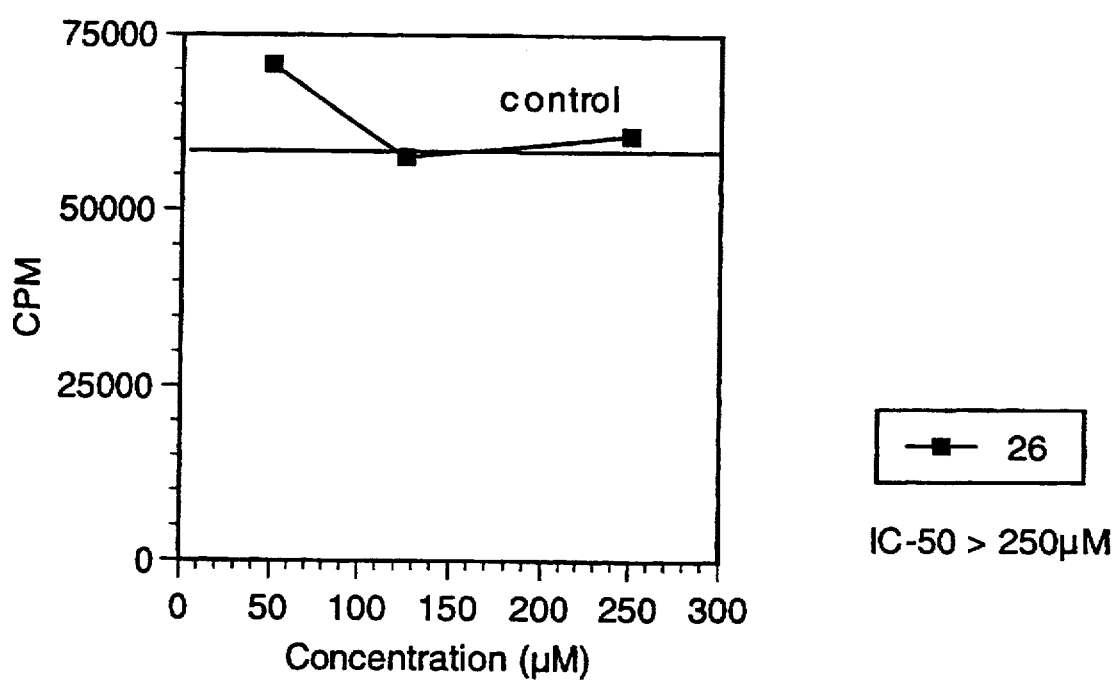
Figure 2C:
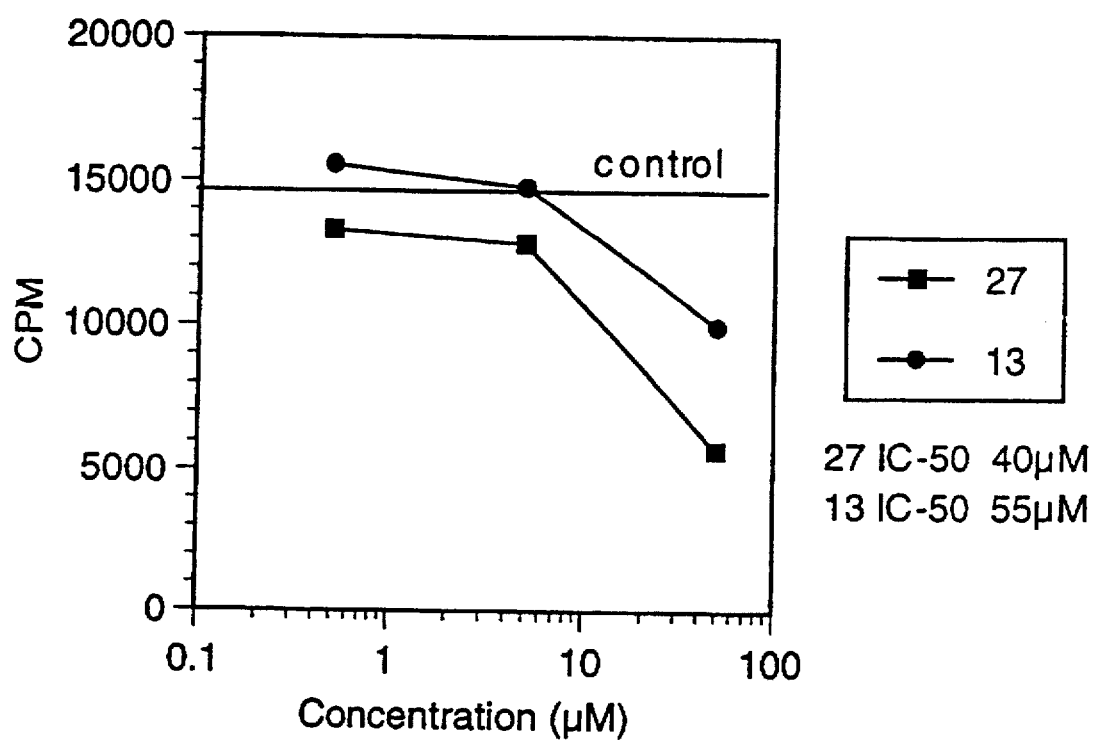
FIG. 2C and 2D report activity data for compounds nos. 27 and 13 and IC50 data, respectively in a mixed lymphocyte reaction.

This example illustrates therapeutic potential of the inventive compounds by comparing potency (inhibitive activity) with cytotoxicity data obtained using the following indicative assay procedures. In a mixed lymphocyte reaction assay of compounds nos. 5, 13, 26 and 27, a two-way mixed lymphocyte reaction shows a proliferative PMBC response to allogeneic stimulation. Compounds nos. 5 and 26 exhibit the least assay activity in this specific, immune-modulating activity assay, having IC50 values exceeding 250 mM, as shown in FIGS. 2A and 2B. Both compounds nos. 27 and 13 exhibit dose-response activity in this assay, having IC50's of 40 and 55 mM, respectively, illustrated in FIG. 2C.

Figure 2D:
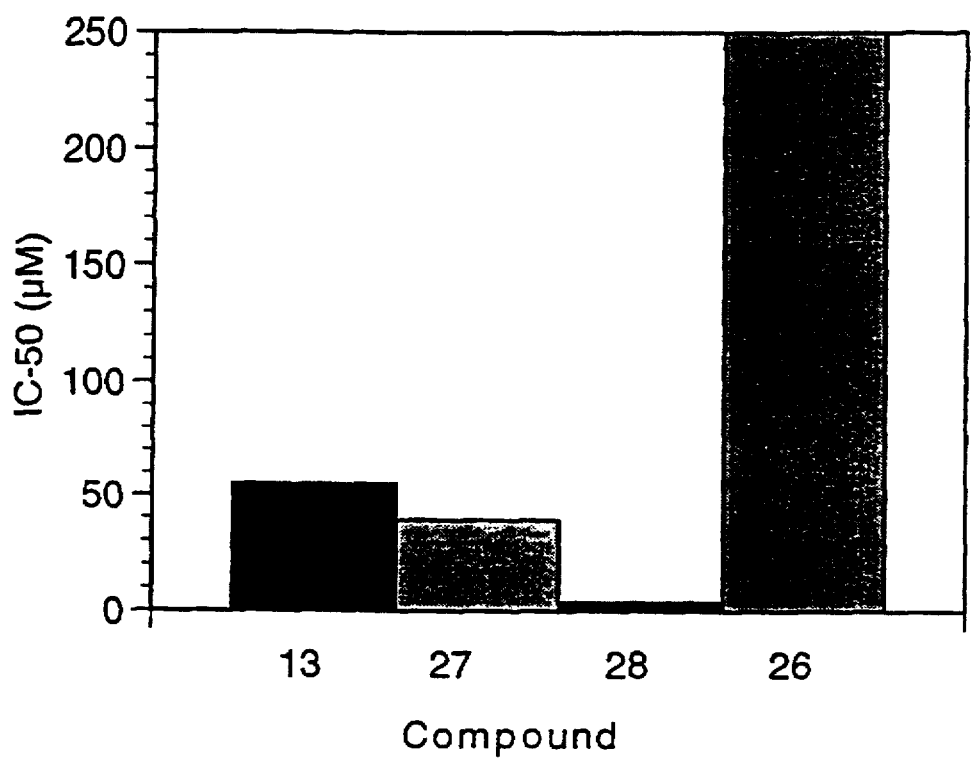

FIG. 2D shows a bar graph of IC50 values for five inventive compounds (see above for corresponding chemical names) in a mixed lymphocyte assay measuring immune suppression activity of the compounds. Compound no. 27 did not exhibit significant suppressive activity. Compound no. 28 proved the most potent compound of those assayed.

Figure 2E:
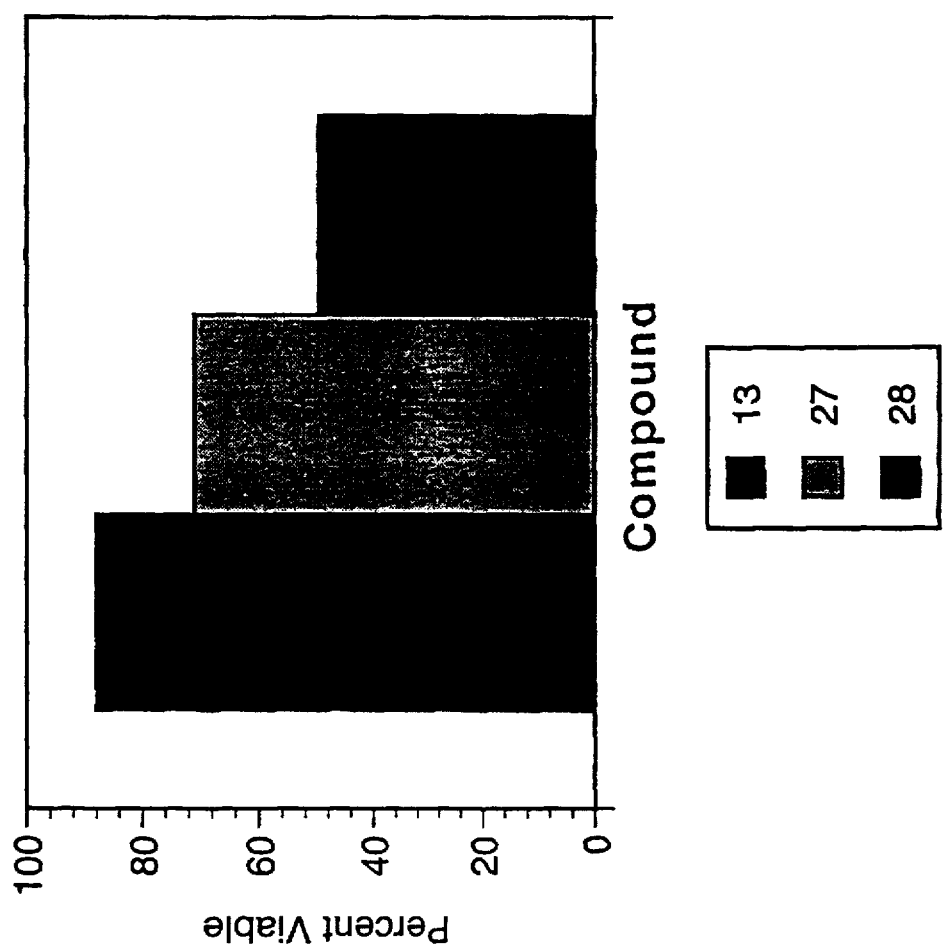
FIG. 2E shows percent viability for five inventive compounds (corresponding chemical names below) in a mixed lymphocyte assay measuring immune suppression activity of the compounds tested.

Cell percent viability in mixed lymphocyte reaction assay culture was determined after six days of cell culture. FIG. 2E shows percent viability bar graph results. Control cells unexposed to drugs are generally 78 to 85% viable under these culture conditions. In this assay, all inventive compounds were present at 100 µM concentrations, generally well above corresponding IC50 values in this assay (see FIG. 2D). The most potent compound, compound no. 28, was also the most cytotoxic at 100 µM, but this concentration is well above its IC50 value, suggesting a significant therapeutic window. Compounds nos. 13 and 27 exhibited little or no cytotoxicity at concentrations well above their respective IC-50 values.

Ten additional representative inventive compounds were assayed, showing impressive biological activity results, in a procedure according to that used in Example 21. IC50 values for tested inventive compounds were obtained in the thymocyte IL-2, co-stimulation assay, as described above. Fifty percent (50%) lethal dose concentrations (LD50) for these ten compounds were obtained using the following cytotoxicity assay.

Figure 2F:
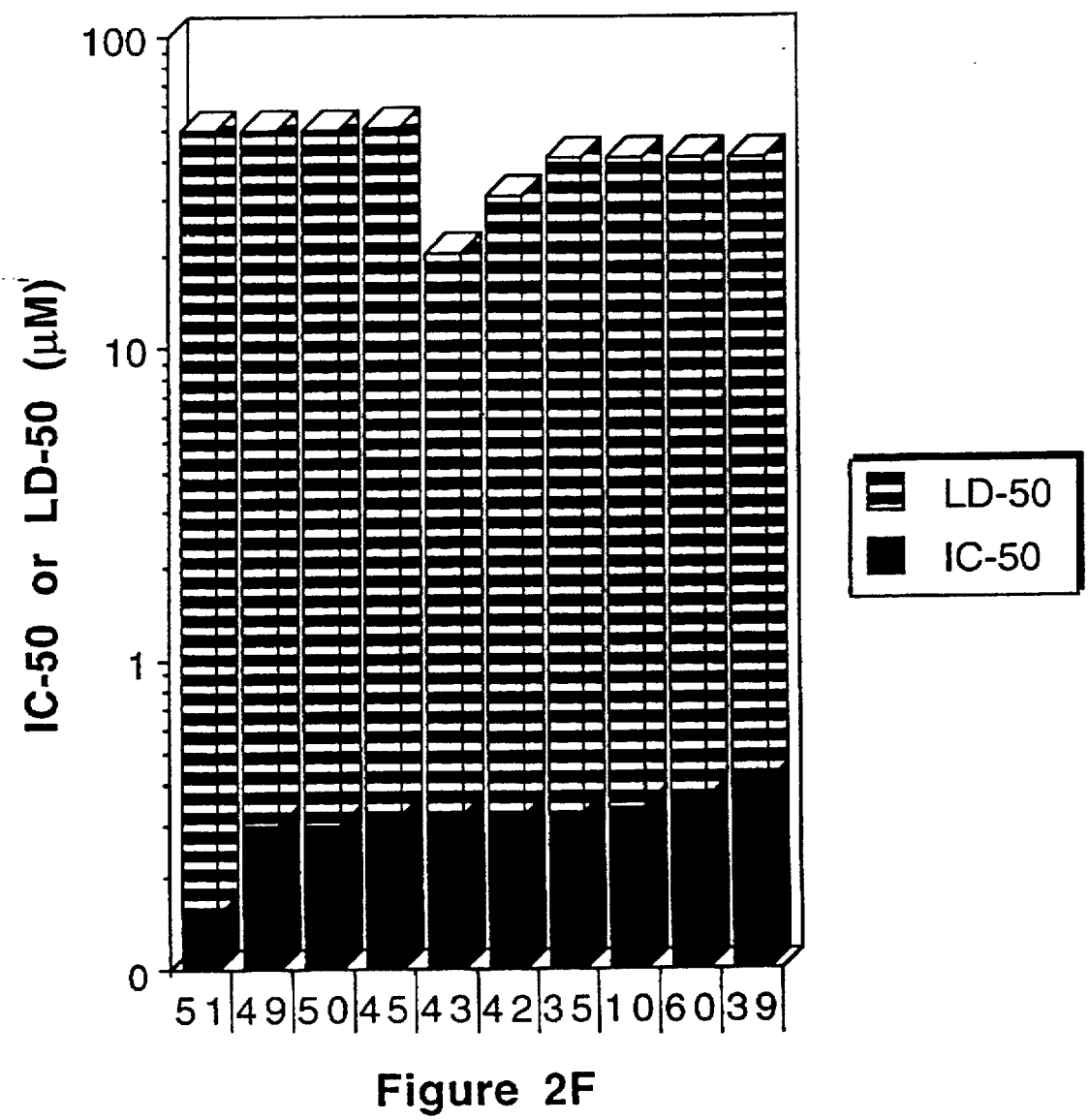
FIG. 2F shows percent viability results from a mixed lymphocyte reaction assay

Human bone marrow-derived stromal cells (early passage) were plated at $10^4$ cells/well and allowed to reach confluency following 3 days of refeeding. The stromal cells were treated with inventive compounds for 2 hours prior to washing, and using a viability dye, BCECF, analyzing fluorescence. The highest concentration used was 50 µM (hence, an LD50 value of 50 µM would indicate no effect at 50 µM). FIG. 2F illustrates results obtained from both the thymocyte co-stimulation assay (IC50 values) and the cytotoxicity assay (ID50) for inventive compounds nos.: 10, 35, 39, 42, 43, 45, 49, 50, 51 and 60. As shown, most of the compounds are non-cytotoxic to stromal cells, yet are very potent proliferation inhibitors in the thymocyte IL-2, co-stimulation assay.

EXAMPLE 24

This example illustrates the effects of several inventive compounds exhibiting inhibitive effects on murine thymocyte proliferation. The data presented and discussed suggests that the inventive compounds function by mechanisms previously unknown. In a first part of this example, compounds nos. 30, 33, 28 and 27 (see above for chemical names and structures) show effective inhibition of murine thymocyte proliferation stimulated by Con A and interleukin 1 alpha (IL-1α). Compounds nos. 30, 33, 28 and 27 were added to cell cultures two hours prior to activation with Con A and IL-1α in a thymocyte co-stimulation procedure akin to that discussed in example 21. All compounds tested in the assay exhibited dose-response inhibitive properties and dose-response curves for each compound were obtained.

IC50 values determined for each inventive compound tested are as follow: compound no. 30 has an IC50 of 0.94 µM, compound no. 33 has an IC50 of 8.6 µM, compound no. 28 has an IC50 of 4.6 µM, and compound no. 27 has an IC50 of less than 12.5 µM. Background counts in the assay were less than 200 cpm.

In supplemental investigations, results obtained illustrate that the inventive compounds utilize different immunosuppressive mechanisms than known mechanisms of two widely-studied immunosuppressants, CsA and or FK506. In a proliferation assay, mouse thymocytes were pre-incubated overnight with Con A (a "priming step"), washed, and re-stimulated with IL-2 in the absence of inventive compounds. On day 4, the cells were pulsed with tritiated thymidine and allowed to incubate for an additional 4 hours. The cells were harvested and the amount of tritiated thymidine incorporated by the harvested cells was determined in a liquid scintillation counter. FIG. 3A reports results obtained. In control cells, pre-incubation with Con A "primes" thymocytes by stimulating the CD3 receptor in a manner similar to antigen recognition. Research has shown that CD3 antibody can be substituted for Con A. When IL-2 was subsequently added, the thymoctye cells proliferated. CsA added during Con A incubation, "priming," inhibited thymocyte proliferation in response to IL-2 stimulation. However, when thymocytes were pre-incubated with ConA and inventive compound no. 35, "priming" occurred, shown by subsequently-observed, normal thymocyte proliferation in response to IL-2 stimulation, as shown in FIG. 3. The inventive compounds do not inhibit proliferation by interfering with this "priming step," necessary for subsequent proliferation in response to IL-2 stimulation.

Figure 3B:
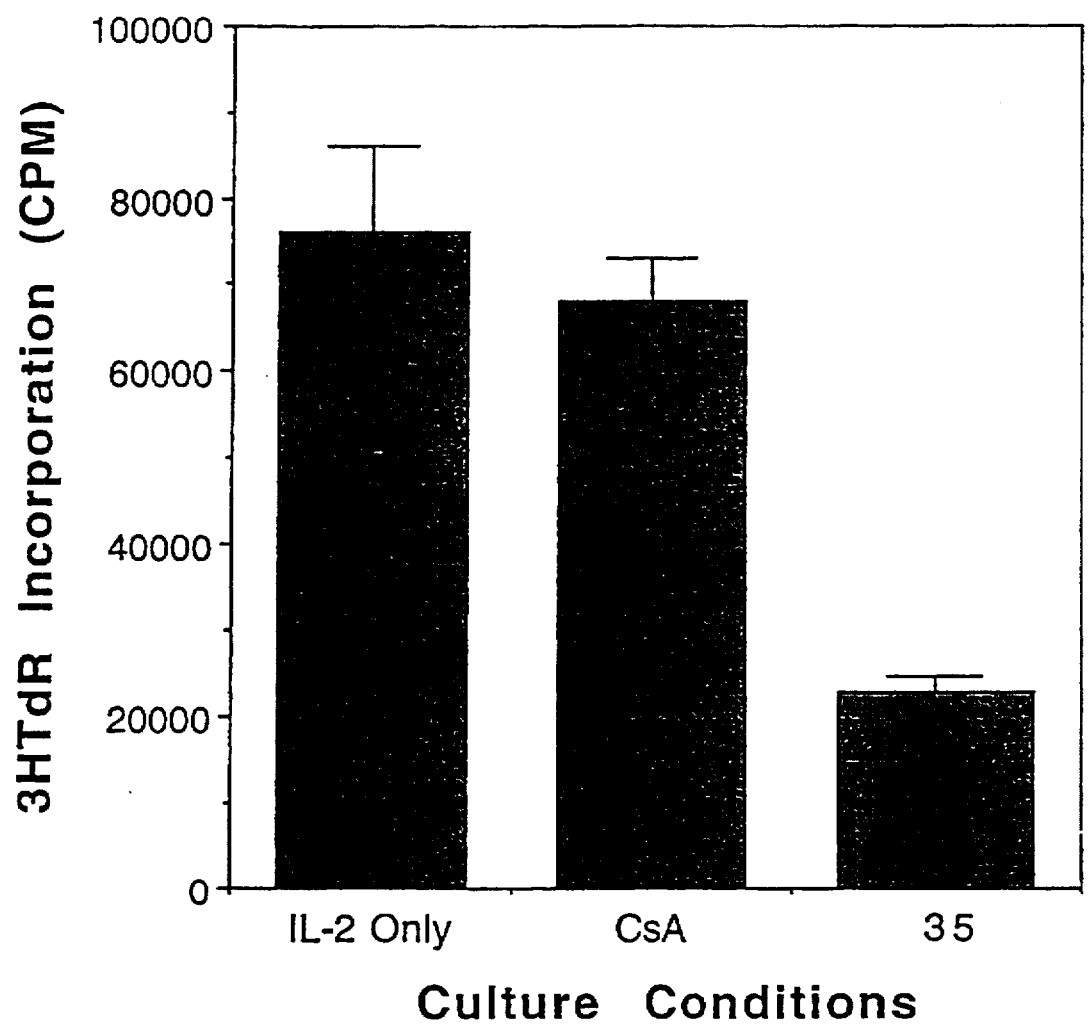
FIG. 3B shows comparative results from inhition assays for co-stimulated thymocyte proliferation.

Additionally, the cells were pre-incubated with Con A overnight, washed and stimulated with IL-2 (with or without addition of CsA or inventive compound). On day 4, the cells were pulsed with tritiated thymidine and allowed to incubate for an additional 4 hours. The cells were harvested and the amount of incorporated tritiated thymidine was determined in a liquid scintillation counter. Cells pre-treated with Con A proliferated in response to IL-2 addition. FIG. 3B shows results obtained in these assays. CsA (50 µM) exhibited very little inhibition of thymocyte proliferation (indicated by the amount of incorporated dye recorded). In sharp contrast however, inventive compound no. 35 (at far less concentration, 1 µM) dramatically inhibited thymocyte proliferation.

These experiments conclusively indicate that CsA and FK506 (inhibiting CD3 in like manner) have a different action mechanism, as compared with the inventive compounds. CsA inhibits ConA "priming." The inventive compounds do not. The inventive compounds inhibit IL-2 stimulation, CsA does not. The results shown indicate that the inventive compounds would be useful for reducing or preventing side effects from conditions requiring cellular stimulants.

EXAMPLE 25

Figure 4:
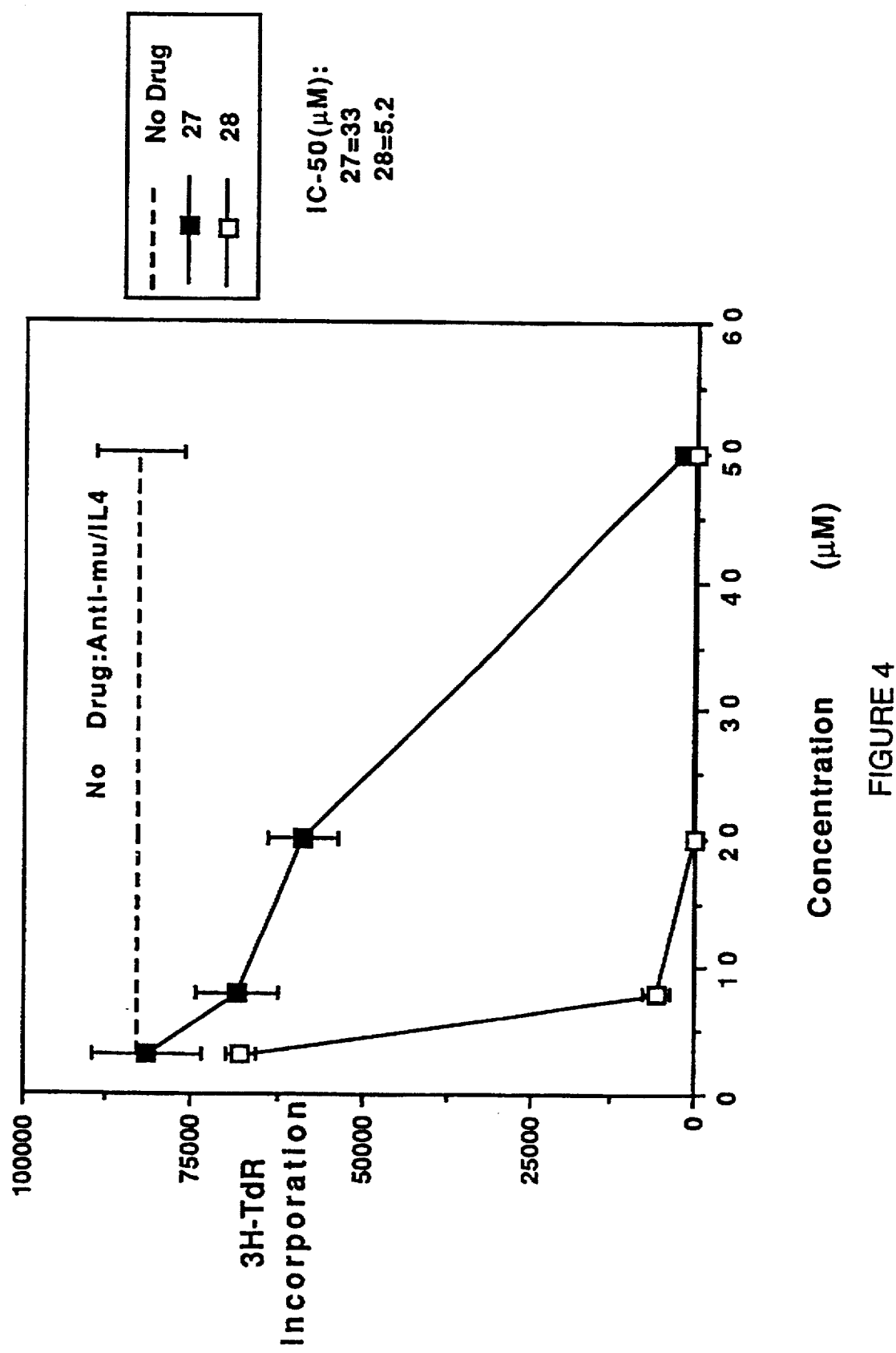
FIG. 4 reports IC50 values for compounds nos. 27 and 28 in a murine splenocyte proliferation (anti-mu stimulated assay).

This example illustrates inhibitive effects of compounds nos. 27 and 28 on murine splenocyte proliferation stimulated by anti-mu (10 mg/ml) and interleukin-4 (IL-4, 12.5 ng/ml). This in vitro assay, described above, is indicative of immune-suppressive/autoimmune treatment assay emphasizing humoral or B cell immune response. The inventive compound was added to the cells at the doses indicated two hours prior to activation with anti-mu and IL-4. Both compounds nos. 27 and 28 inhibited splenocyte proliferation in a dose-response manner. IC50 values for compounds nos. 27 and 28 were 3.3 µM and 5.2 µM, respectively, as shown in FIG. 4. Background counts were less than 200 cpm.

EXAMPLE 26

Figure 5A:
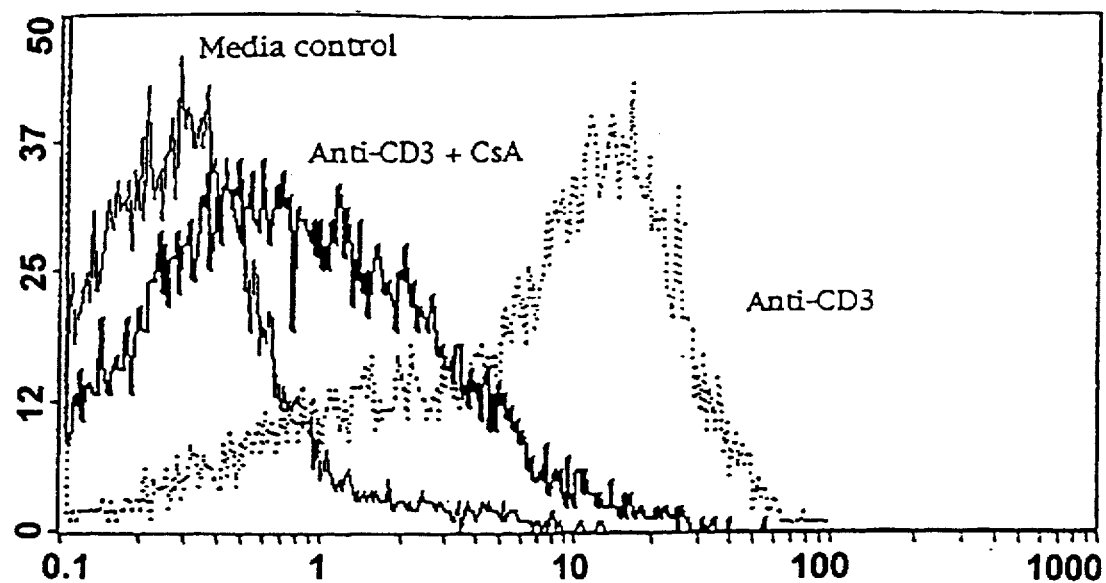
FIGS. 5A and 5B are frequency histograms of measurements for 20,000 cells in an assay illustrating IL-2 (alpha chain CD25) receptor expression.
Figure 5B:
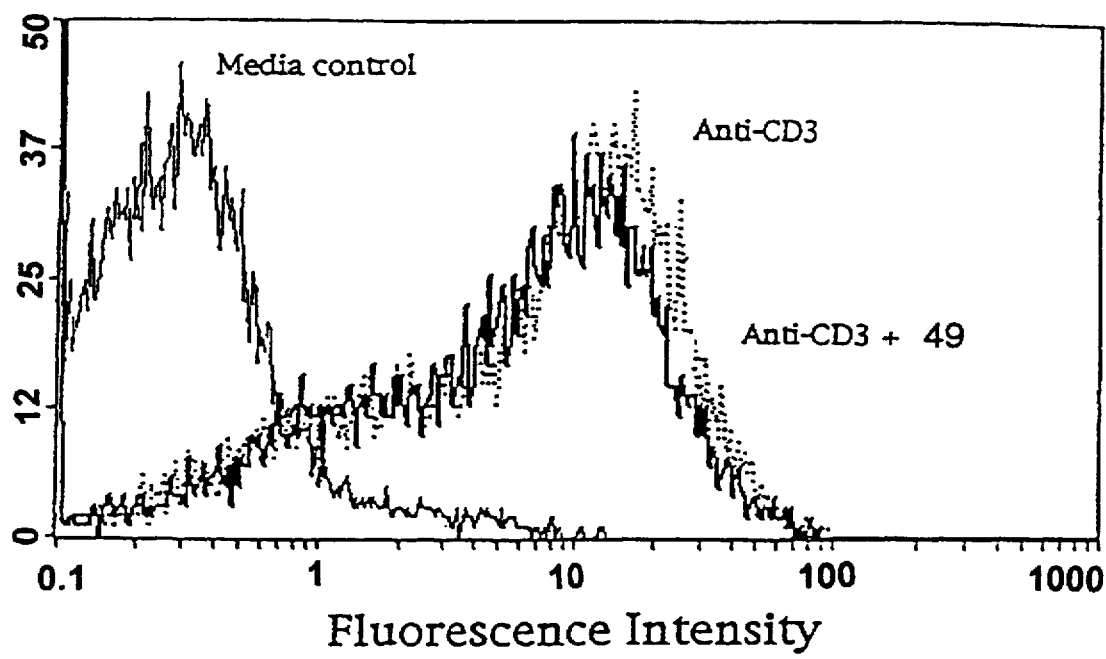

This investigation illustrates IL-2 (alpha chain CD25) receptor expression on mouse splenoyctes. The IL-2 receptor is not expressed on resting T-cells, but is rapidly-induced by certain stimulants, e.g. antigen recognition or treatment with ConA or antibodies to CD3 (anti-CD3). IL-2-dependent proliferation requires IL-2 receptor expression. Splenocytes were stimulated with anti-CD3 antibody (10 µg/ml) with or without the addition of CsA (20 µM) or compound no. 49 (1 µM). Following overnight incubation, the splenocytes were stained with a fluoresceinated anti-IL-2 receptor antibody and fluorescence measured by flow cytometry. FIGS. 5A and 5B are frequency histograms of measurements for 20,000 cells per sample. The media control has a low level of fluorescence, while stimulation with anti-CD3 stimulates large relative increases in IL-2 receptor-expression (peak labeled anti-CD3 in FIGS. 5A and 5B). Coincubation with CsA inhibits CD3-stimulated, IL-2 receptor expression, while incubation with inventive compound no. 49, at a concentration that blocks 90% of splenocyte IL-2-stimulated proliferation, has no effect on receptor expression. These data confirm that CsA and compound no. 49 affect immune cells by different mechanisms.

EXAMPLE 27

Figure 6:
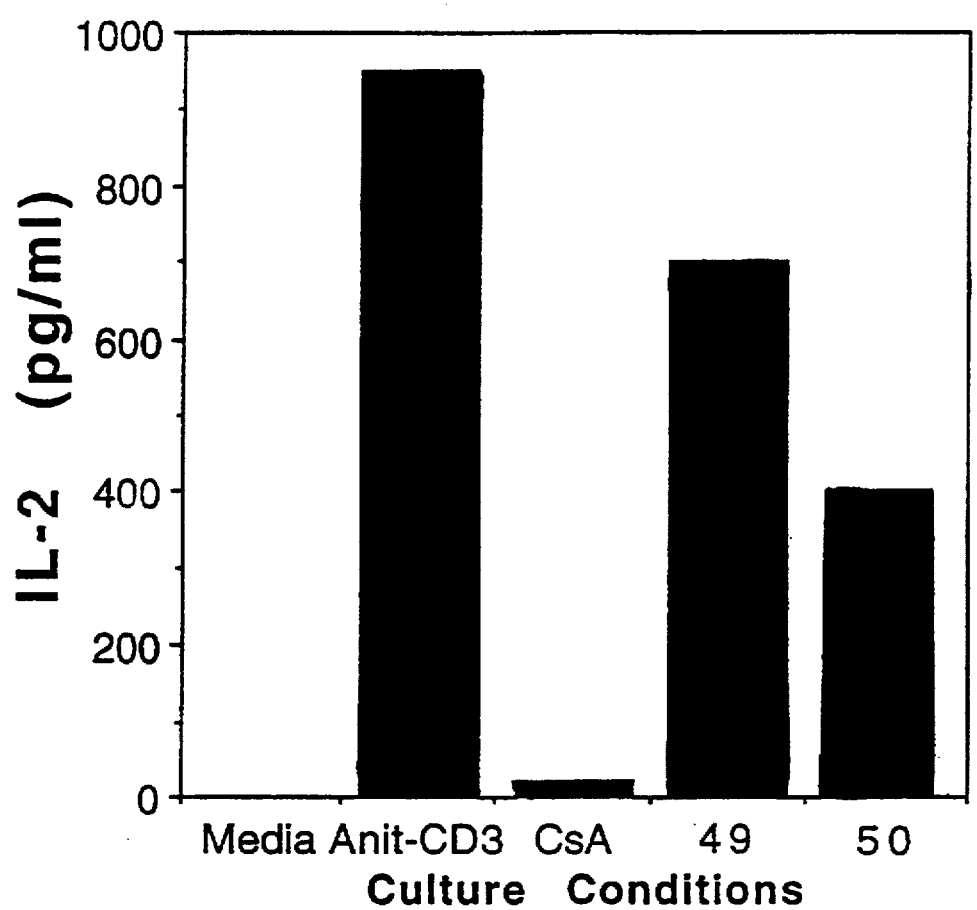
FIG. 6 shows results for compounds nos. 49 and 50 as compared with CsA in an inhibitive assay for production of IL-2 in murine thymocytes.

This example shows that compounds nos. 49 and 50 do not inhibit production of IL-2 in murine thymocytes, in contrast to the effects of CsA. Thymocytes were stimulated with ConA and IL-1 for 4 days with or without adding inventive compounds to the culture media. The supernatants were removed and assayed by ELISA for IL-2 levels by a commercially available kit. The results, shown in FIG. 6, illustrate that CsA incubation at 20 nM inhibits IL-2 production and secretion. Also shown, these exemplary inventive compounds tested do not inhibit IL-2. These data illustrate that CsA and the inventive compounds tested interfere with immune cell function via different mechanisms.

EXAMPLE 28

Figure 7:
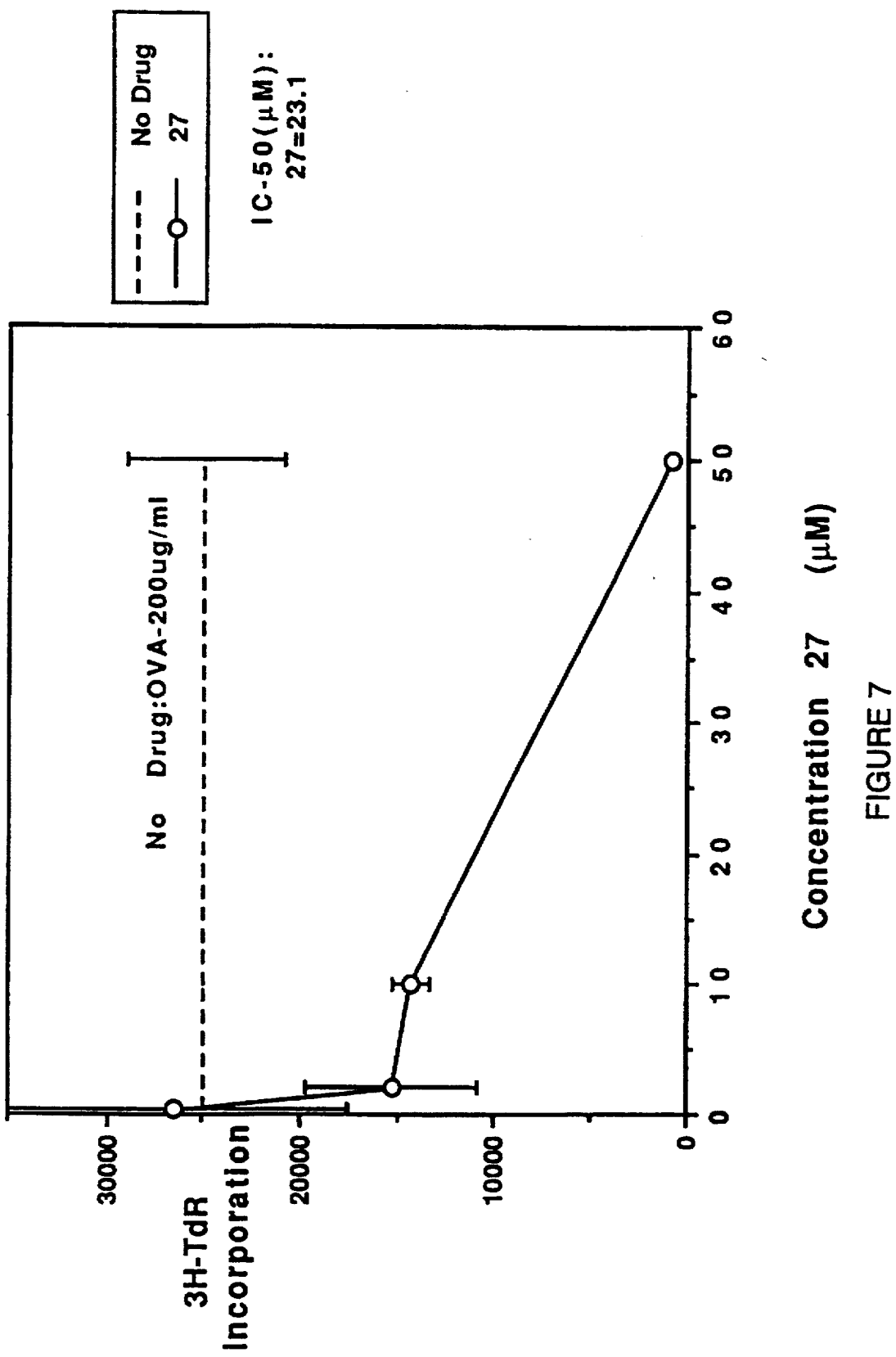
FIGS. 7 and 8 report dose response results from an in vitro assay emphasizing cellular or T cell immune response.
Figure 8:
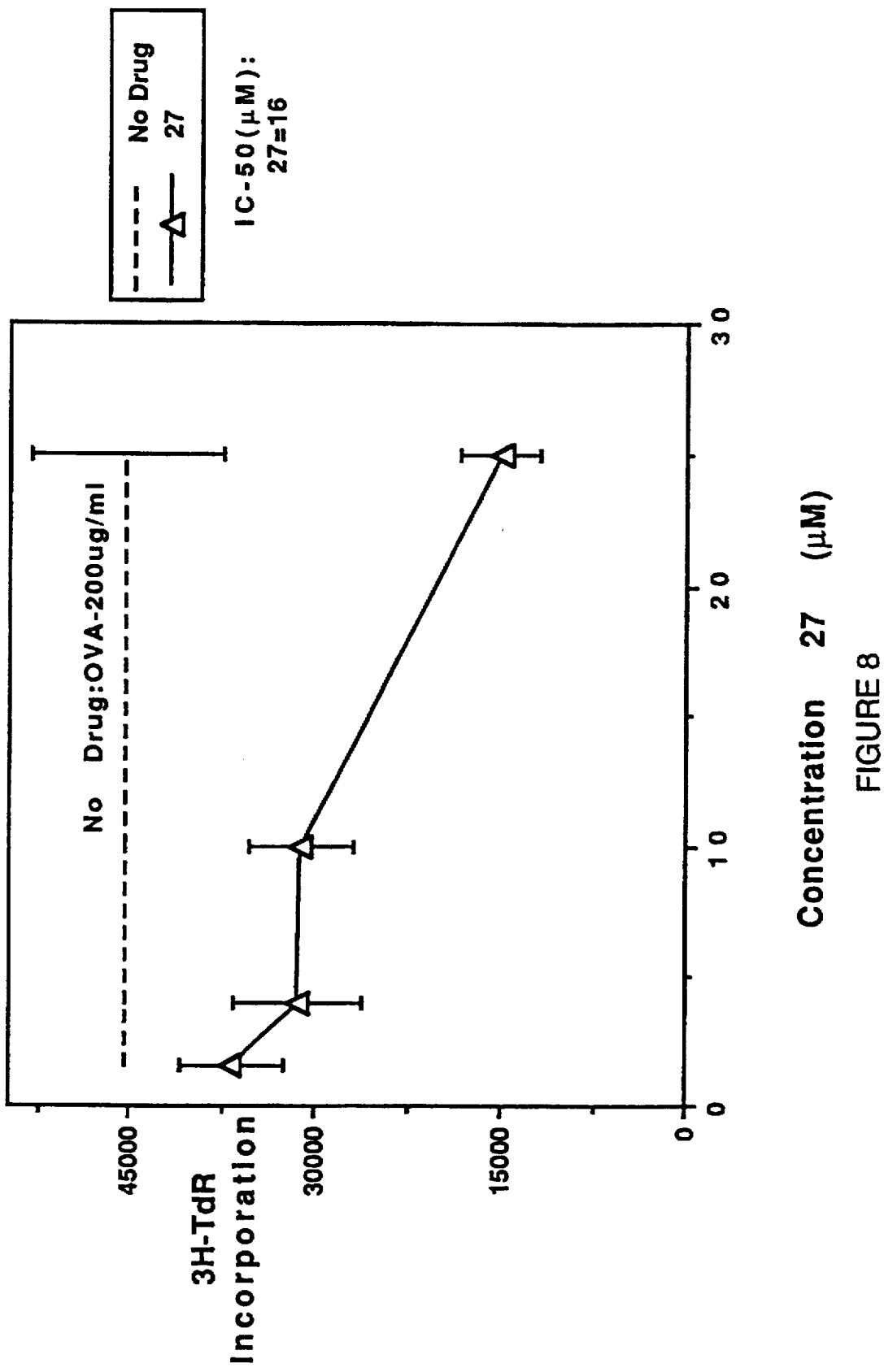

This example illustrates activity of representative inventive compounds nos. 27, 49, 50, 45, 43 or 41 (above) in assays detecting activity in response to cell stimulus. One assay, murine lymph node cell proliferation (stimulated by antigen), was used to determine inhibitive activity of compound no. 27 on proliferation of the lymph node cells. This in vitro assay is described above and is an immune suppressive/autoimmune treatment assay emphasizing cellular or T cell immune response. The assay used murine T cells that proliferate in vitro in response to a soluble protein antigen, used to prime the T cells in vivo. Drug was added to the cells at doses indicated in FIGS. 7 and 8 (showing assay results) two hours prior to activation with alloantigen. Compound no. 27 inhibited T cell proliferation in a dose-response manner. IC50 values for compound no. 27 are 23.1 µM for a first experiment (results shown in FIG. 7) and 19 µM for a second experiment (results shown in FIG. 8).

Figure 9A:
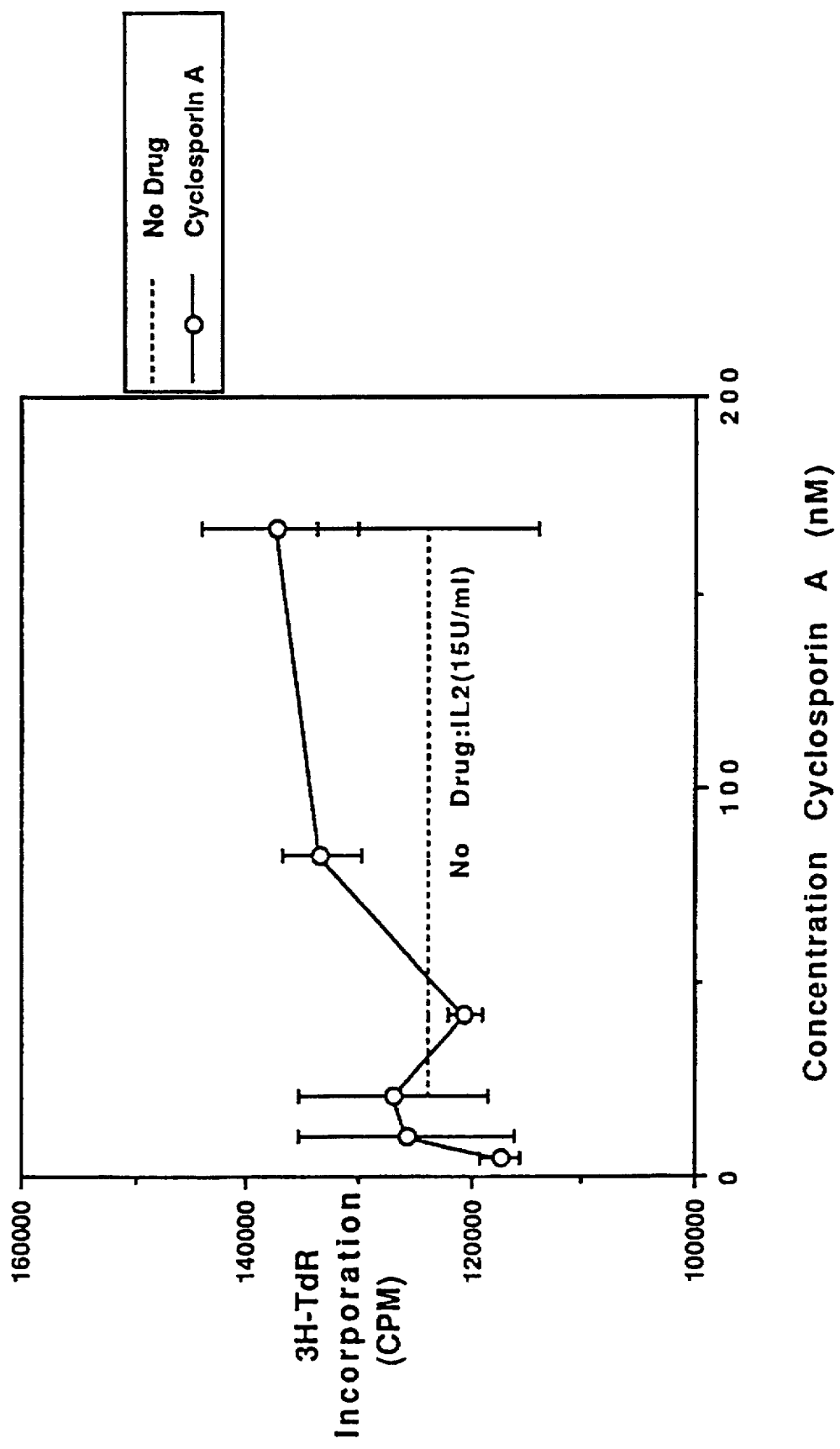
FIGS. 9A and 9B report inhibitive activity for the inventive compounds, as compared with CsA on direct IL-2-induced proliferation in a murine cytotoxic T-cell line, CT6.
Figure 9B:
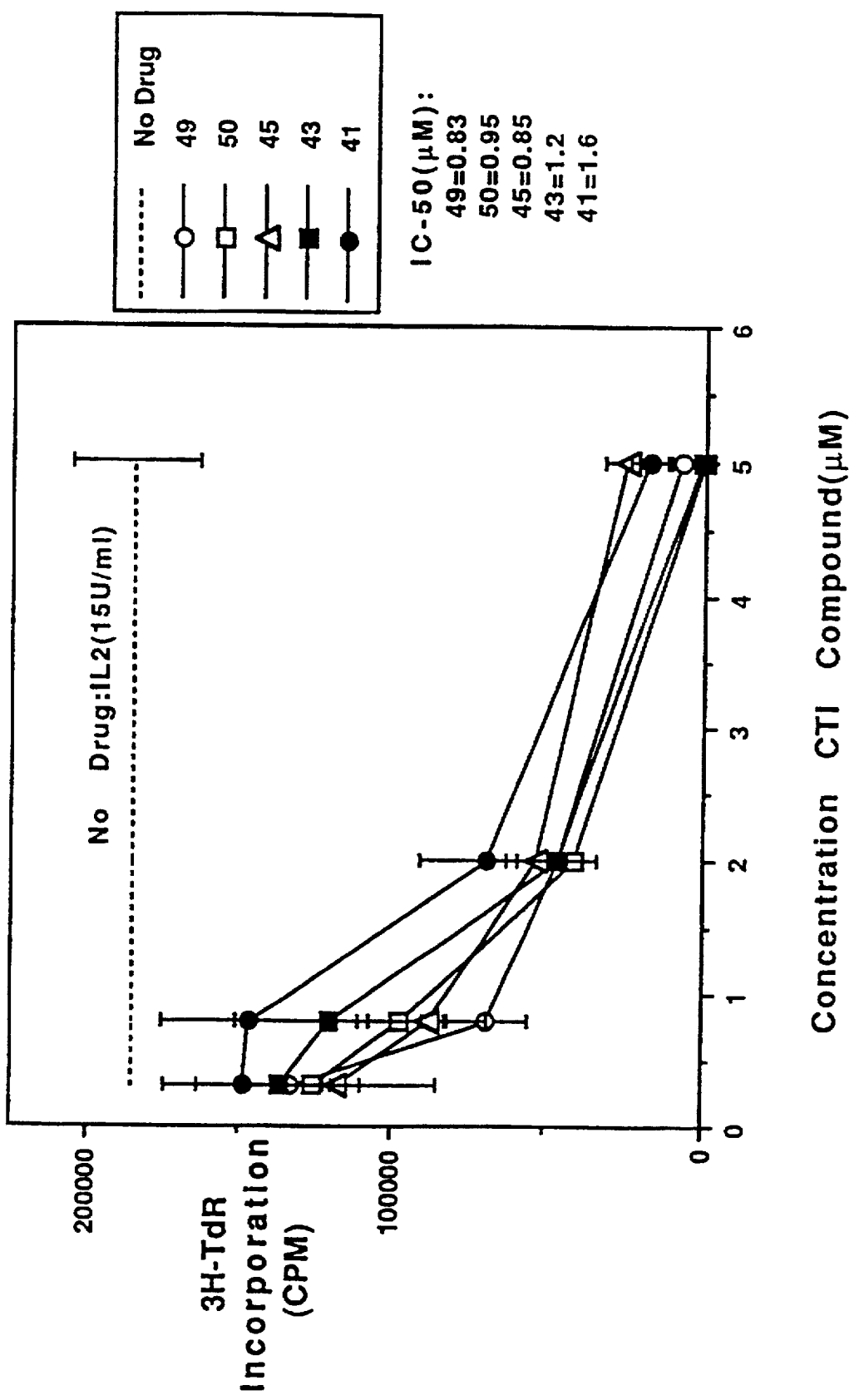

Another assay in this example was used to determine inhibitive activity of the inventive compounds on direct IL-2-induced proliferation in a murine cytotoxic T-cell line, CT6. The CT6 cell line is an IL-2-dependent cell line. IL-2 was removed from the medium for 24 hours prior to stimulation. One hour prior to IL-2 stimulation, either CsA or compounds nos. 49, 50, 45, 43 or 41 were added at various concentrations. The cells were stimulated with IL-2 and amount of tritiated thymidine dye incorporated was measured 48 hours later. Background counts were less than 5000 cpm. Assay results are graphically represented in FIGS. 9A and 9B. The two graphs show that CsA and the inventive compounds have divergent effects on IL-2 induced proliferation. CsA does not inhibit proliferation, even at very high concentrations. However, in distinct contrast, the inventive compounds inhibit direct IL-2-induced CT6 proliferation.

EXAMPLE 29

Figure 10:
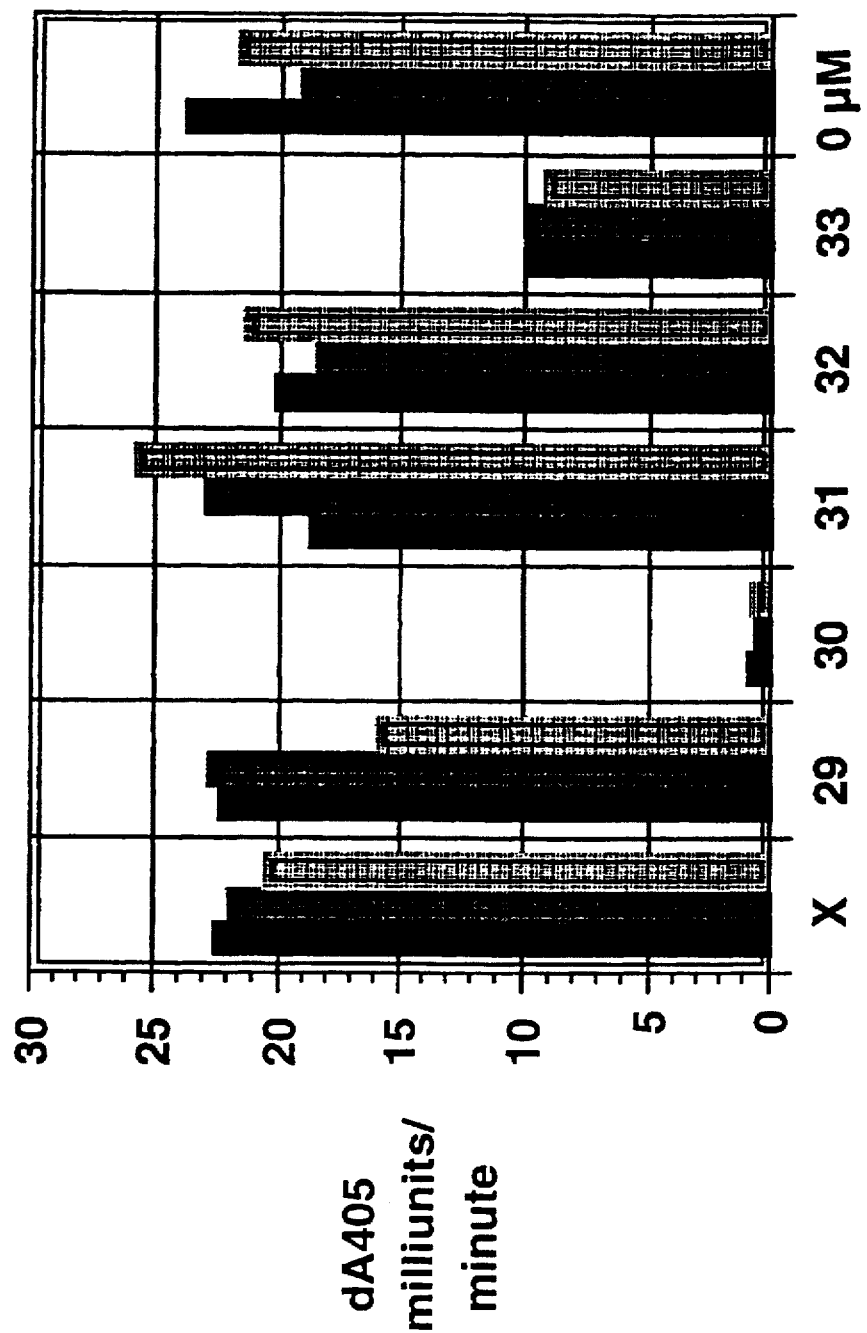
FIG. 10 illustrates activity of the inventive compounds in anti-yeast and antifungal assays.

This example illustrates the effects of a reference compound "X", and inventive compounds nos. 29, 30, 31, 32 and 33 (see above for names and structures) on yeast growth (*Saccharomyces cervisiae*)—using 100 µM concentrations—as compared with yeast activity in the absence of any compound additive (control). This assay measured anti-yeast and anti-fungal activity of the the inventive compounds tested. As shown in FIG. 10, compounds no. 30 and 33 showed yeast-growth inhibitive activity, suggesting the inventive compounds tested are potential topical or systemic anti-microbial compounds.

EXAMPLE 30

This example illustrates potential antigen specific anergy-induction of inventive compounds. Anergy, as used herein, is a prolonged state of T cell "unresponsiveness," due to T cell antigen recognition (without co-stimulation) or induced proliferation blockage. This later T cell anergy may occur when a T cell's proliferation ability in response to IL-2 is blocked by some agent. Anergy is generally considered to be a type of tolerance to antigen activation. Thus, anergy is a means for predicting in vivo tolerance-enhancing agents. Tolerence is important in preventing organ rejection in transplant procedures, as well as other autoimmune diseases such as scleroderma, rheumatoid arthritis, lupus, and diabetes-related autoimmunity.

Figure 11:
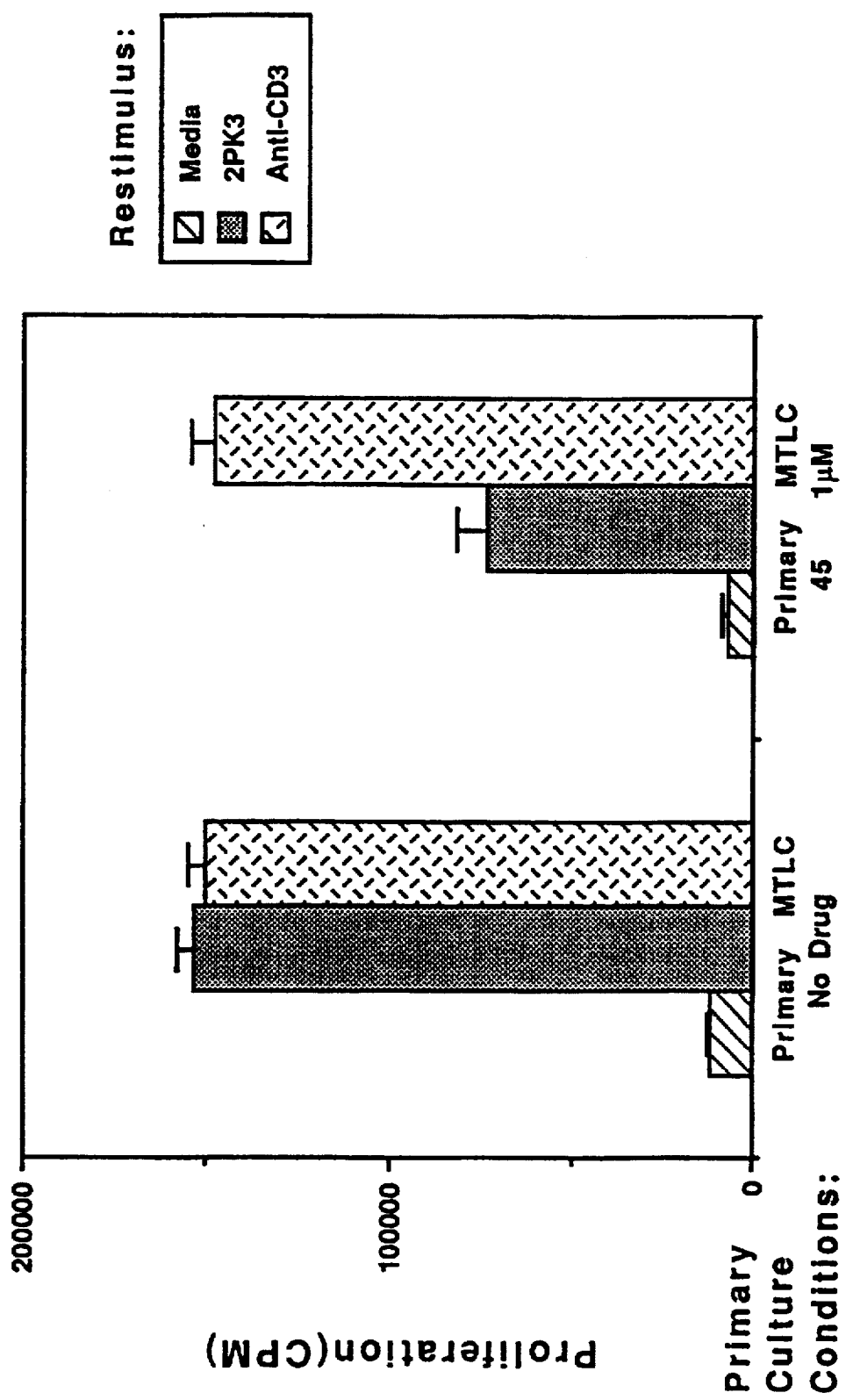
FIG. 11 reports activity data for inventive compounds in an assay designed to detect potential antigen specific anergy-induction.

A B cell tumor, 2PK3 (H-2d) was used as a stimulating cell for C57BL/6 splenocytes (H-2b), a responding cell. Mixed cultures of B-cell tumor and splenocytes were incubated for 5 days with and without 1 µM of compound no. 45. After 5 days, the cells were washed and resuspended with either media, the original antigen (2PK3) or anti-CD3. Tritiated thymidine was added to the resulting suspensions and thymidine incorporation measured 24 hours later. Results are shown in FIG. 11. As illustrated, culture treated with inventive compound no. 45 and untreated cultures responded equivilantly to anti-CD3. However, cultures incubated with inventive compound no. 45 for 5 days exhibited a decreased response to primary antigen, 2PK3. Thus, C57BL/6 splenocytes were inhibited from responding to an original antigen by the inventive compound used in the pre-incubation step. However, a normal culture response to anti-CD3 stimulation suggests the inventive compounds may exhibit antigen-specific anergy induction properties.

EXAMPLE 31

This example illustrates inhibitive effects of the inventive compounds on human stromal and Balb/3T3 cell proliferation in response to PDGF stimulation.

Figure 12:
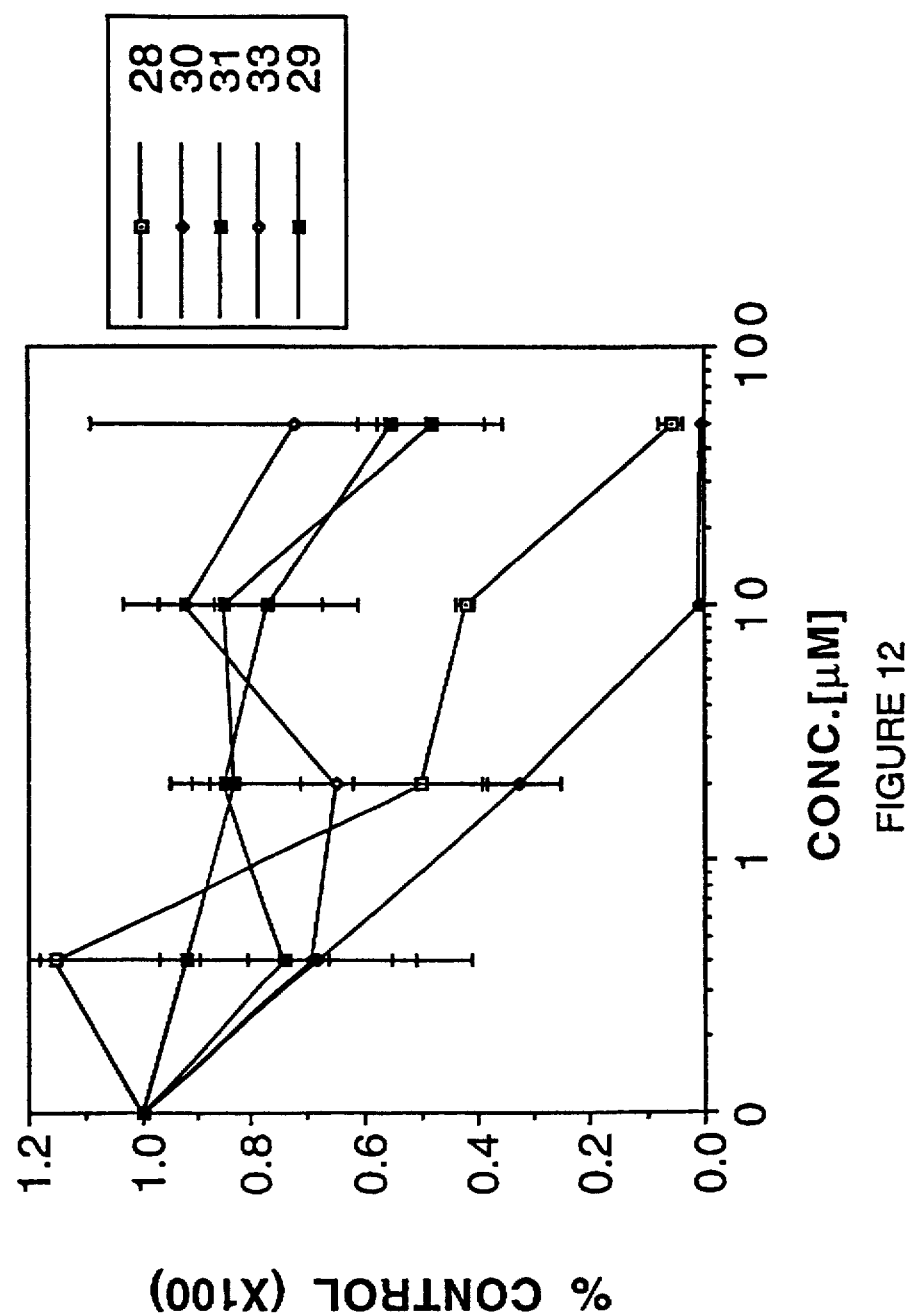
FIG. 12 shows activity results for inventive compound nos. 28, 30, 31, 33 and 29 in an assay useful in predicting therapeutic activity for preventing or treating restenosis, atherosclerosis and coronary artery disease.

In an assay, useful in predicting therapeutic activity for preventing or treating restenosis, atherosclerosis and coronary artery disease, human stromal cells were starved in serum-free media for one day and then stimulated with 50 ng/ml PDGF-BB. Inventive compounds, at various concentrations, were added one hour prior to PDGF stimulation. PDGF and tritiated thymidine were added and the cells allowed to incubate for one day, following addition of the PDGF and thymidine. 24 hours later, the cells were harvested and counted by liquid scintillation counting. Results for compounds nos. 28, 30, 31, 33 and 29 are shown in FIG. 12. Background counts (i.e., starved cells) were approximately 1% of control levels. The results illustrate that the drugs were active in this predictive in vitro model with IC50 values (in μM) of 0.9, 3.2, 40, >50 and >50 for compounds nos. 30, 28, 29, 32 and 31, respectively.

Figure 13:
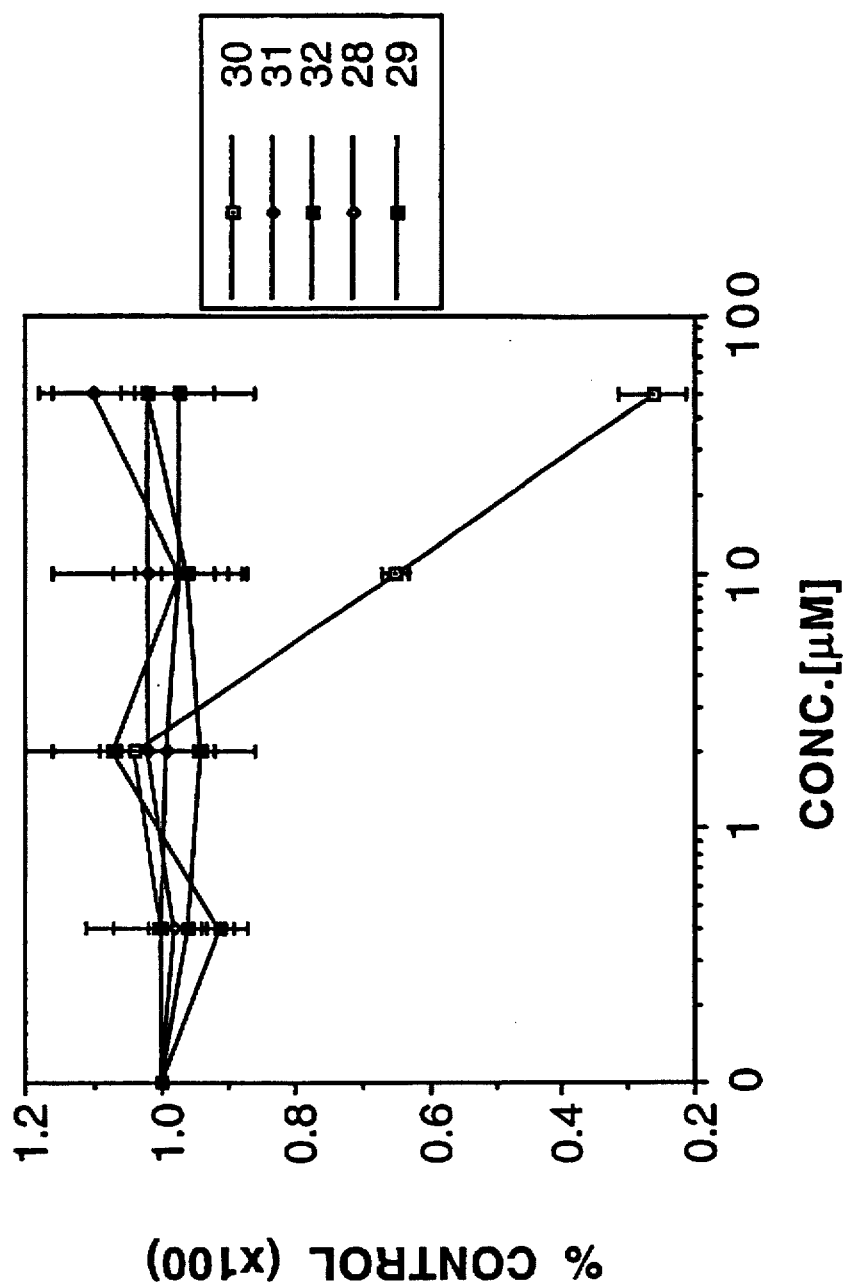
FIG. 13 shows cytotoxic results for inventive compounds in a human stromal cell/PDGF stimulation assay.

In conjunction with the human stromal cell/PDGF stimulation assay, cytotoxicity of the inventive compounds tested to stromal cells was also determined. FIG. 13 shows results for this cytotoxicity assay. Only compound no. 30, exhibiting the most pronounced inhibitive activity of the compounds tested, exhibited cytotoxic effects at concentrations above 0.9 μM, its IC50 value.

Figure 14:
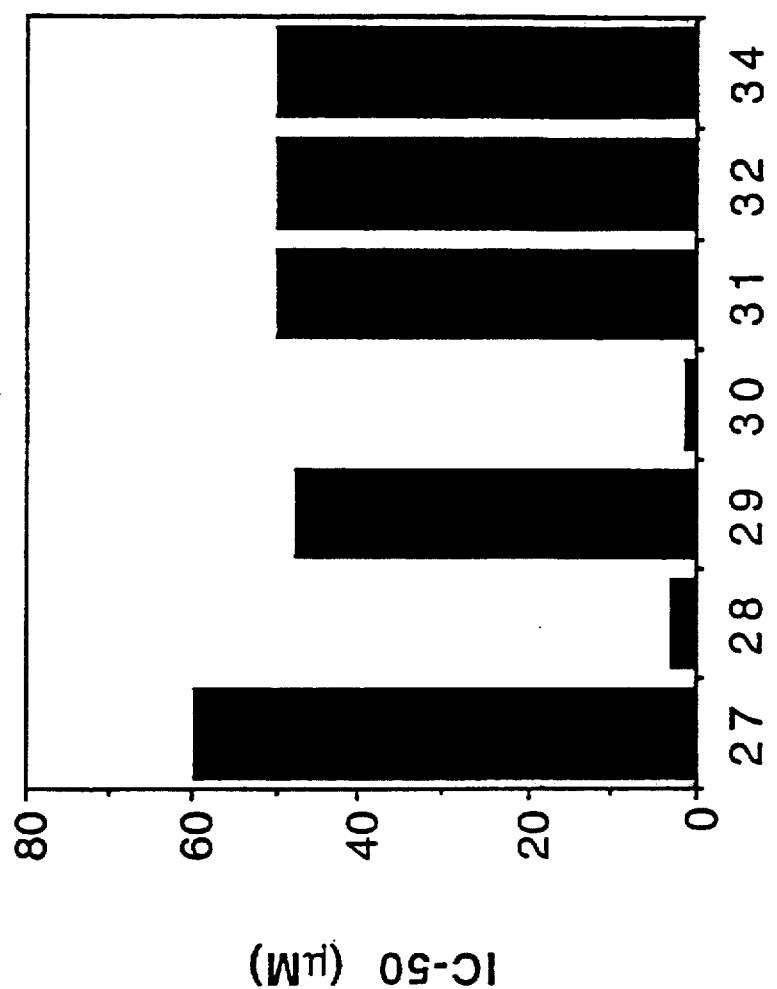
FIG. 14 reports inhibitive activity results for inventive compounds nos. 27, 28, 32, 30, 31, 32 and 34 in an assay measuring inhibitive effects in a PDGF/IL-1 co-stimulation.

In an assay measuring inhibitive effects in a PDGF/IL-1 co-stimulation, proliferation assay, a group of inventive compounds showed inhibitive properties. The PDGF/IL-1 assay is useful in measuring in vitro activity, indicative of therapeutic potential for treating or preventing restenosis and reperfusion. FIG. 14 reports IC50 bar graph results for a group of inventive compounds nos. 27, 28, 32, 30, 31, 32 and 34. In this predictive, in vitro model, compounds nos. 28 and 30 exhibited potent inhibitive activity, suggesting potential use in therapeutic applications for restenosis and reperfusion.

Figure 15:
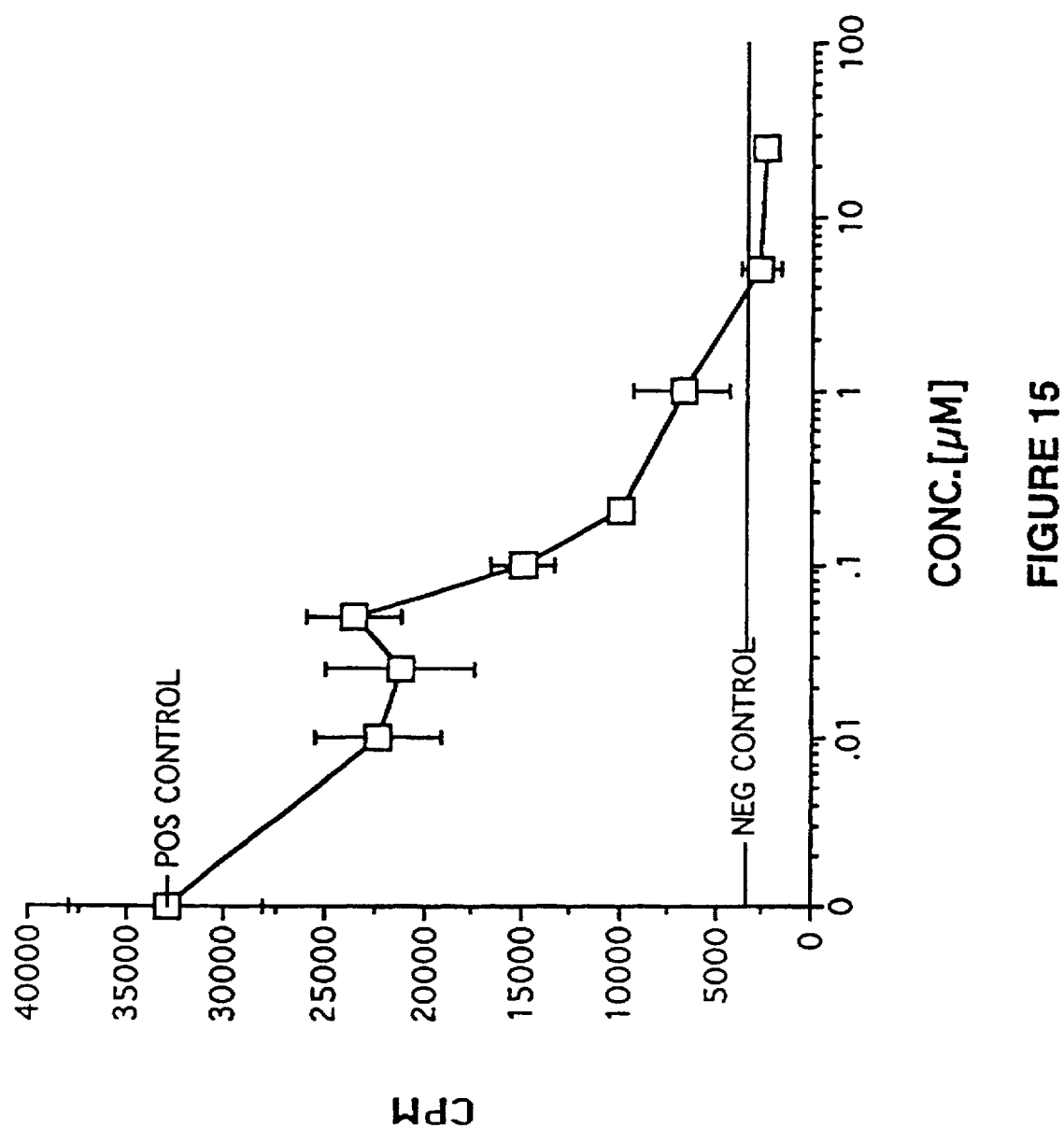
FIG. 15 illustrates a dose response curve for selected inventive compounds in a PDGF-induced proliferation of Balb/3T3 cells.

In yet another assay, research indicates that the inventive compounds possess inhibitory effects on PDGF-induced proliferation of Balb/3T3 cells. Balb/3T3 cells respond vigorously to PDGF stimulation, and are useful in vitro models for further study of PDGF-induced proliferation. Disregulated PDGF-proliferative response has been linked to a variety of diseases, including, e.g., restenosis, atherosclerosis, fibrosis, and tumor cell angiogenesis. Cells were plated in low serum-containing medium for 24 hours prior to stimulation with various concentrations of inventive compound no. 45. PDGF-BB was added at a constant 10 μM concentrations. Tritiated thymidine was added and cells harvested for scintillation counting 24 hours later. FIG. 15 illustrates a dose response curve from this assay, including an IC50 value of approximately 0.08 μM, exemplifying inhibitory activity of the tested compound.

EXAMPLE 32

Figure 16:
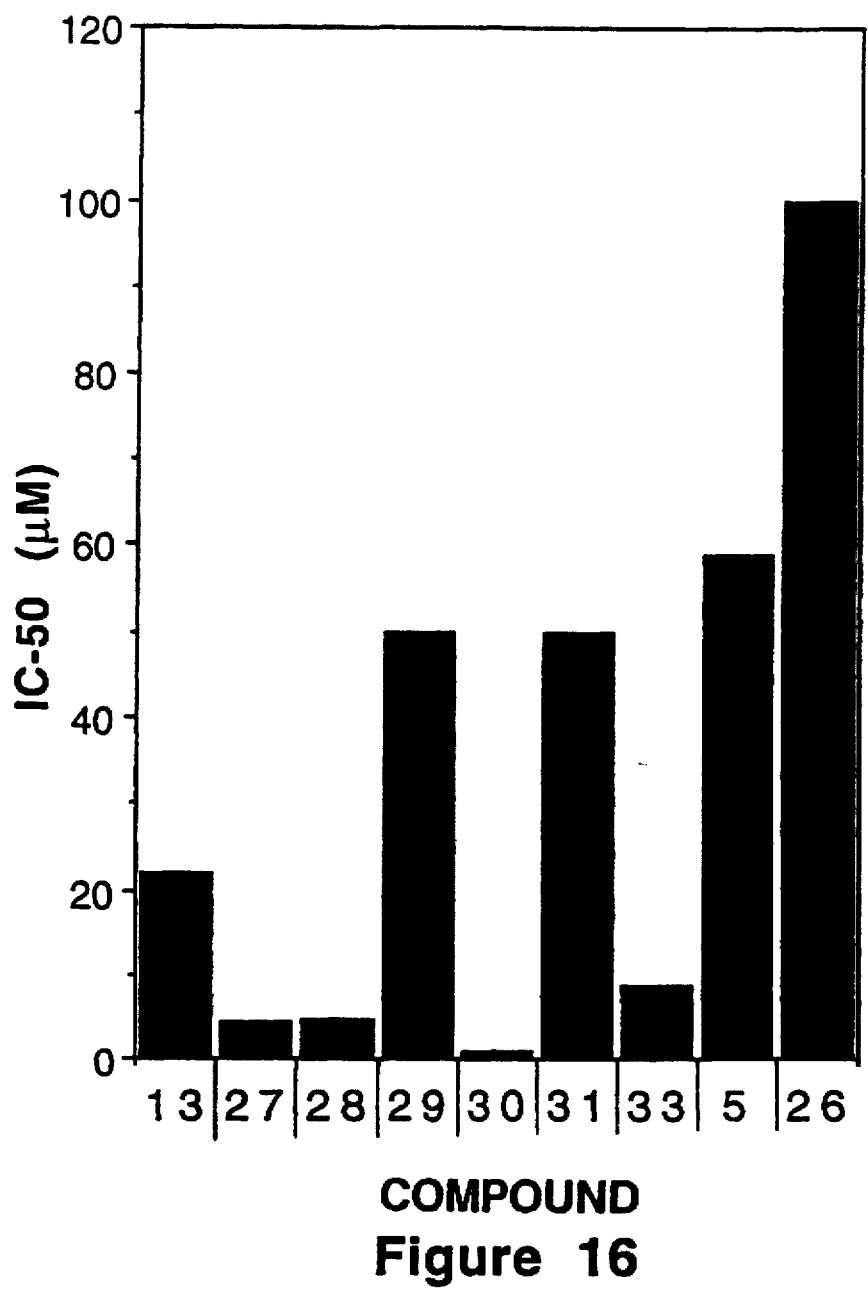
FIG. 16 reports suppressive results for selected inventive compounds in a murine thymocyte ConA/IL-2 co-stimulation assay.

In assays described above and similar to those used in Example 32 and other examples, the ability of various inventive compounds to suppress murine thymocyte and Balb/3T3 cell proliferation in response to selected stimuli was investigated. In a murine thymocyte ConA/IL-2 co-stimulation assay according to Example 23, IC50 values were obtained for inventive compound nos. 13, 27, 28, 29, 30, 31, 33, 5 and 26. FIG. 16 reports comparative results for the different compounds tested in this in vitro model. Compounds nos. 28, 30, and 27 exhibit the most potent immune-suppressive effects in these in vitro models.

Figure 17:
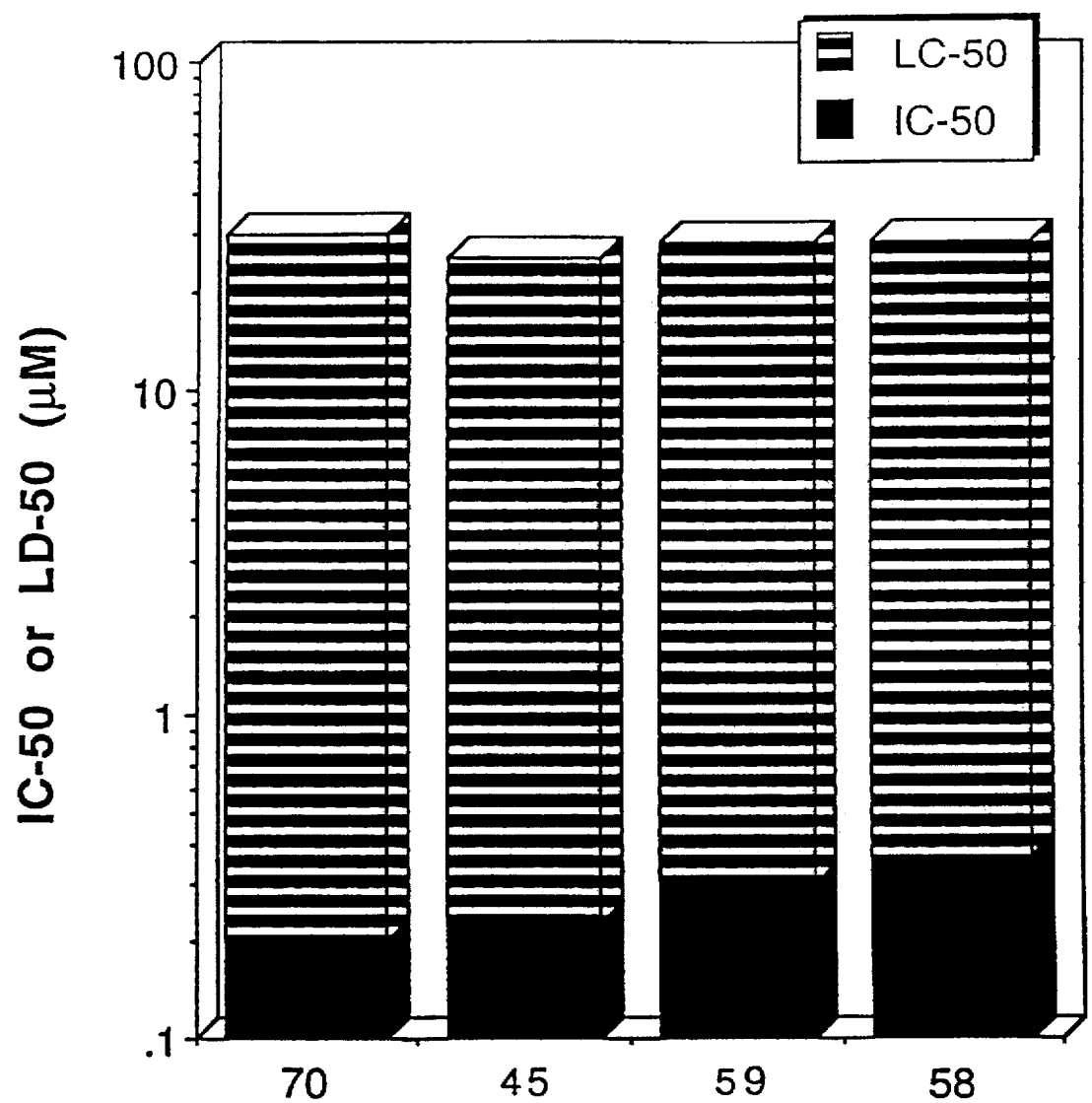
FIG. 17 compares IC50 and ID50 data for several inventive compounds.

In another investigation similar to the Balb/3T3 proliferation assay of Example 32, IC50 and ID50 values for inventive compounds nos. 70, 45, 59 and 58 were determined. LD50 values were determined using a cytotoxicity assay, as in Example 32. In these assays, Balb/3T3 cells, stimulated with PDGF and treated with one of the above inventive compounds in a manner identical to the tritiated thymidine procedure above, were incubated instead with a viable dye BCECF, a fluorescent dye. Fluorescence was measured using a fluorescent plate reader. The highest concentration used was 50 μM, therefore an LD50 value of 50 μM indicates no effect at 50 μM. FIG. 17 illustrates assay results by comparing LC50 value against LD50 values for the inventive compounds tested. Most compounds tested are non-cytotoxic yet are significant inhibitors of proliferation.

EXAMPLE 33

Figure 18:
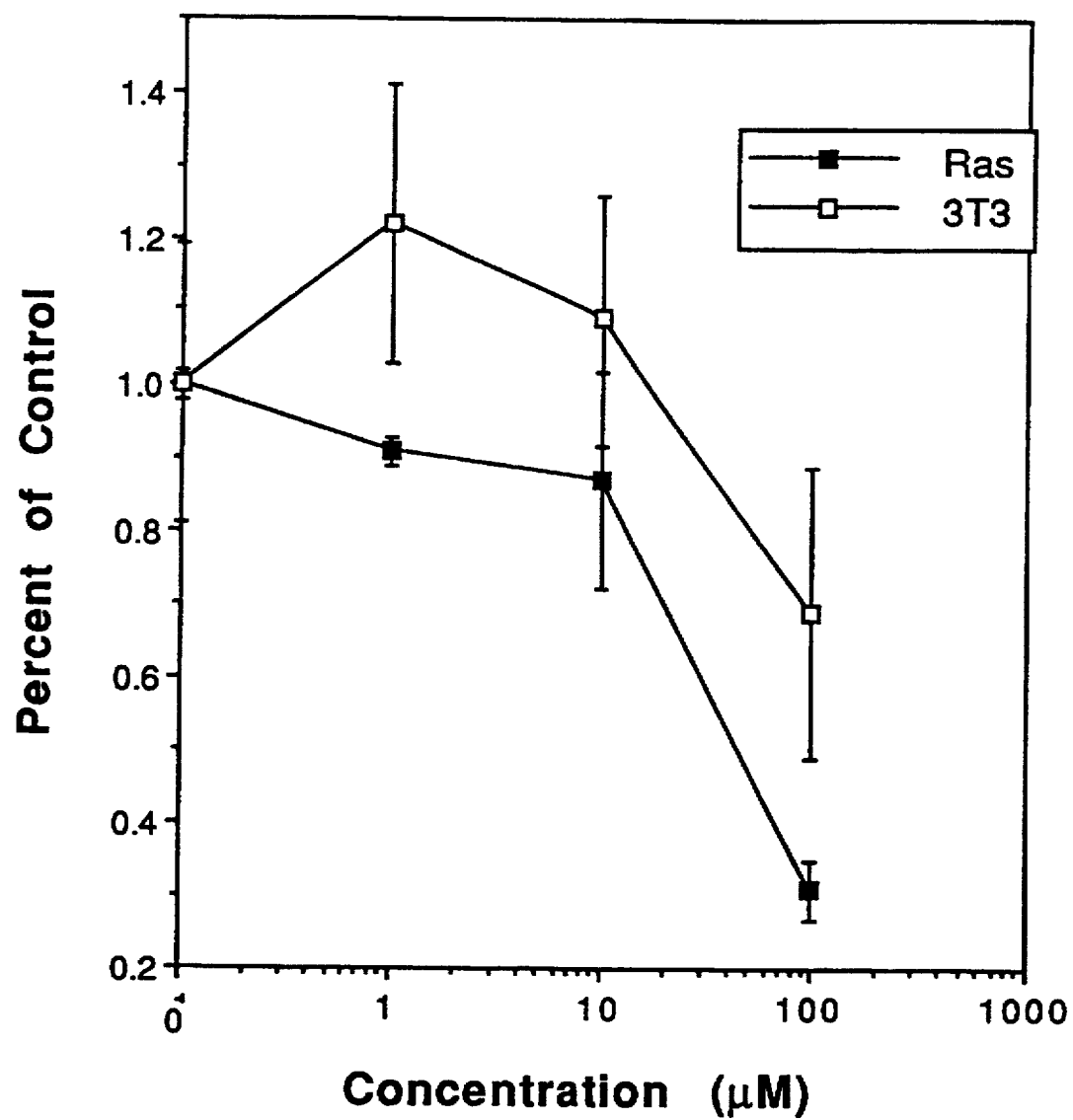
FIG. 18 reports cytotoxicity results for inventive compound no. 27 for transformed (Ras 3T3) cells and non-transformed (normal) cells.

This example compares cytotoxicity results for inventive compound no. 27 for transformed cells and non-transformed cells. In transformed cells (Ras 3T3) and in normal 3T3 cells, cytotoxicity of compound no. 27 at concentrations of 1, 10 and 100 μM was determined. FIG. 18 reports results obtained in this assay. At each of the above concentrations, compound no. 27 was more cytotoxic for the cancer cell than the normal cell. These results indicate the compound tested has differential toxicity for tumor cells, suggesting potential utility in chemotherapeutic cancer treatment.

EXAMPLE 34

Figure 19:
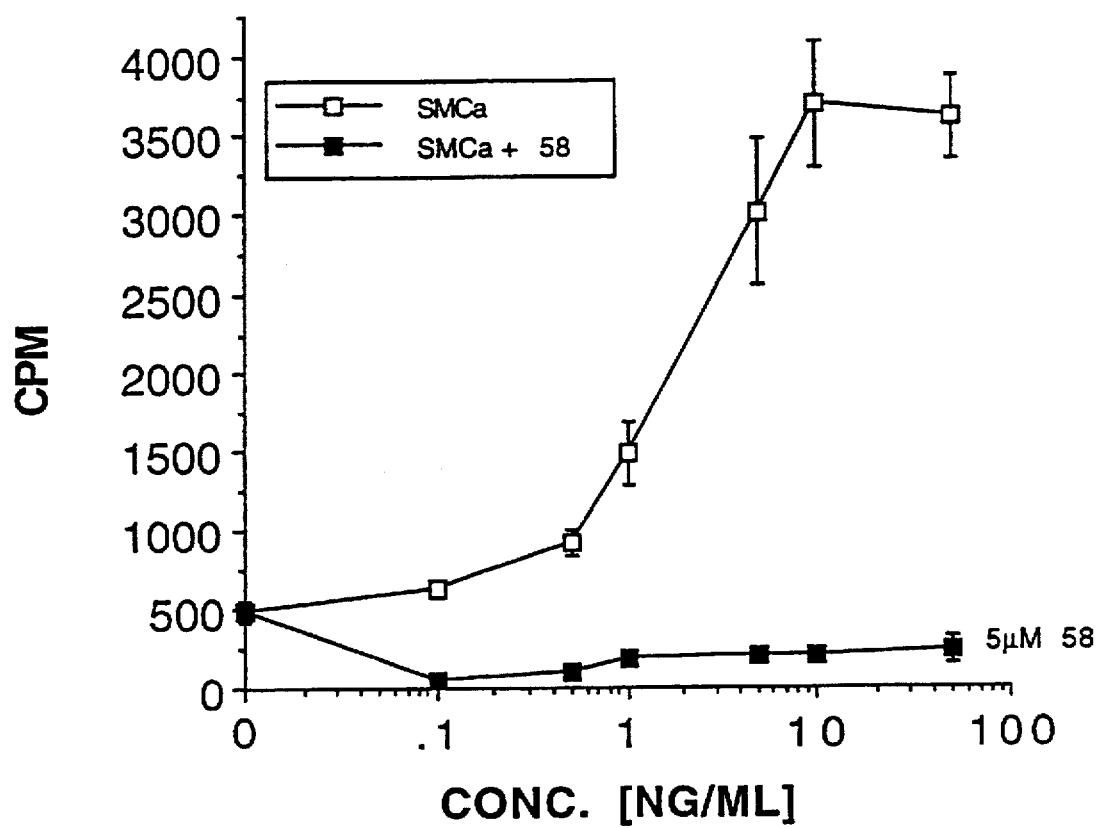
FIG. 19 shows data demonstrating inhibitory effects of inventive compound no. 58 on PDGF-induced proliferation of human aortic smooth muscle cells (aortic SMC). [Fifu]

This example demonstrates inhibitory effects of inventive compound no. 58. One assay was used for investigating effects on PDGF-induced proliferation of human aortic smooth muscle cells (aortic SMC). Cells, purchased from a commercial supplier (Cell Systems, Inc., Seattle, Wash.) were cultured with various concentrations of PDGF-BB with and without addition of compound no. 58 (5 μM). As illustrated in FIG. 19, compound no. 58 inhibits PDGF-BB-induced proliferation even at PDGF concentrations providing maximum proliferative stimulation. In addition, some cultures were treated 1 hour prior to PDGF stimulation with inventive compound no. 58. As shown, PDGF-BB stimulates proliferation in this cell line. Addition of 5 μM of compound no. 58 blocks PDGF-stimulated proliferation and no toxic effects of compound no. 58 were observed.

Figure 20A:
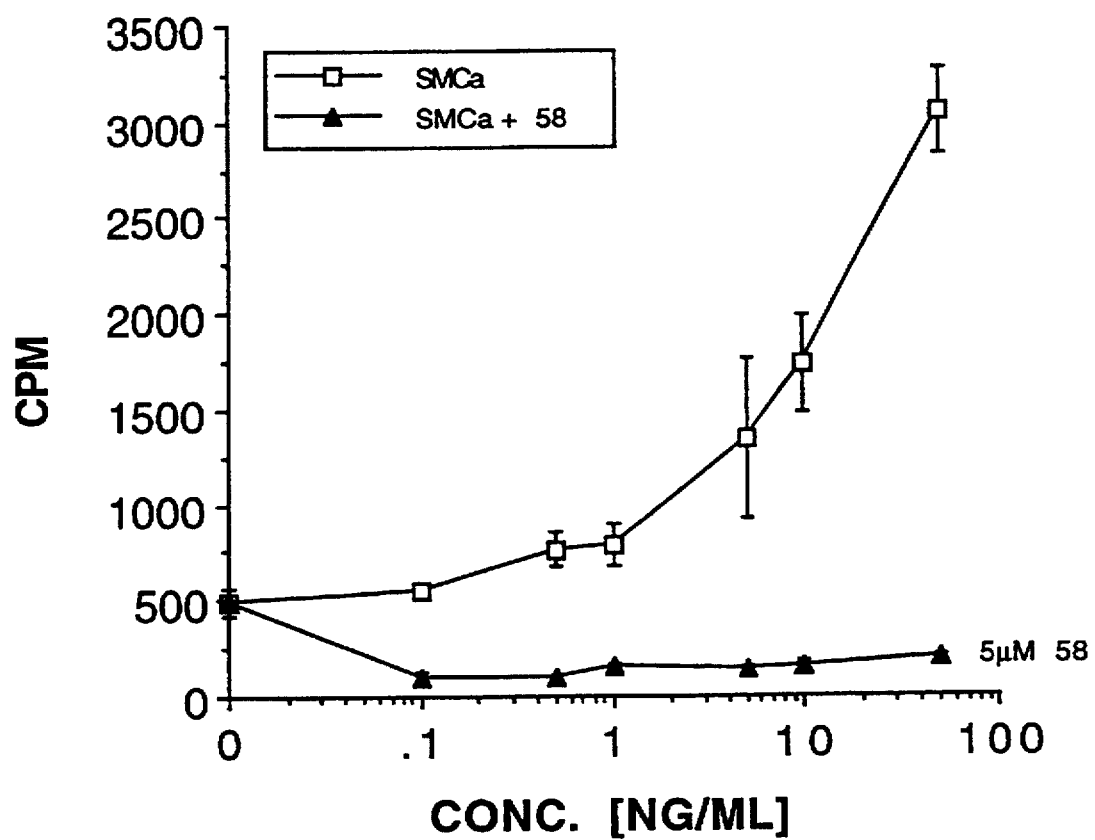
FIGS. 20A and 20B show the effects of compound no. 58 on aFGF and bFGF-induced proliferation in human aortic smooth muscle cells (aortic SMC).
Figure 20B:
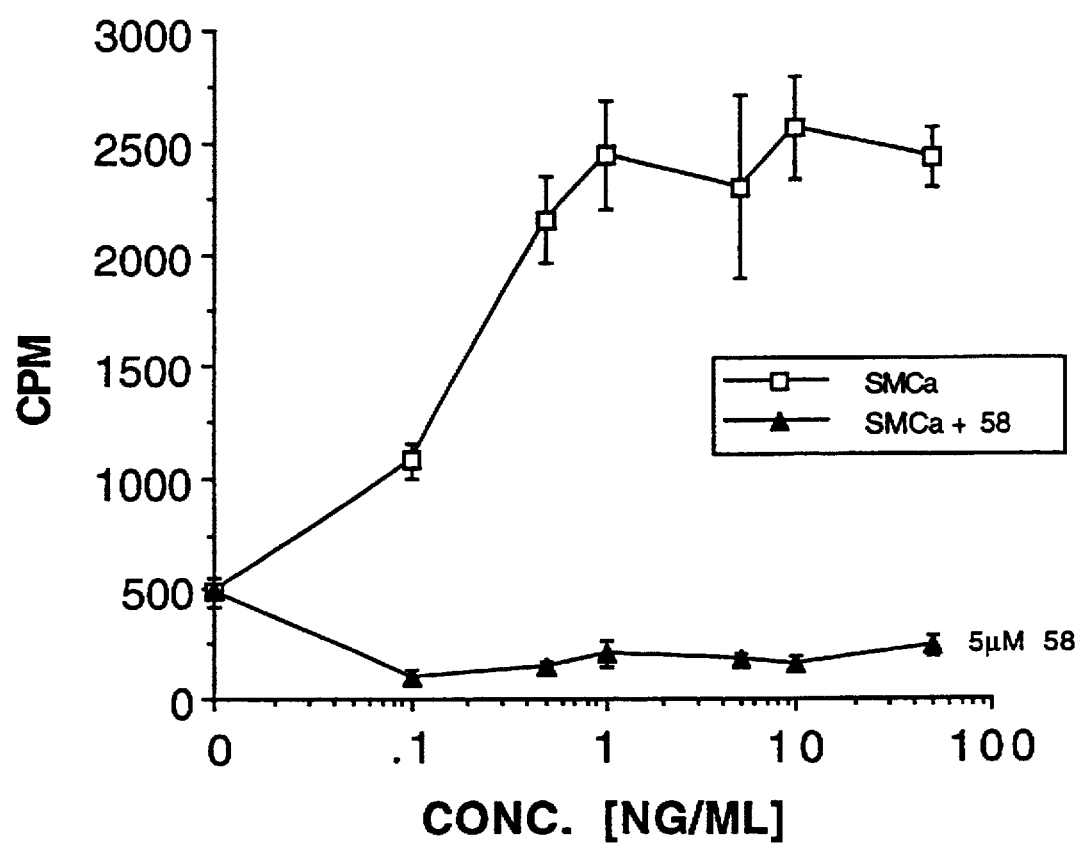

Another assay was used for investigating inhibitory effects of inventive compound no. 58 on either basic or acidic FGF-induced proliferation in human aortic smooth muscle cells (aortic SMC). Disregulated bFGF- or aFGF-induced proliferation is linked to SMC proliferation and neointimal occlusion in atherogenesis and restenosis and plays a role in autocrine and paracrine stimulation of tumor cells and tumor cell-induced angiogenesis. In this assay, cells were grown in reduced serum (0.5% fetal calf serum) for 24 hours prior to stimulating with various concentrations of PDGF. Cells were stimulated with various concentrations overnight of either aFGF or bFGF, adding 5 μM of compound no. 58 in selected cultures. Compound no. 58 is a potent inhibitor of both aFGF- and bFGF-induced proliferation in this cell type, representative of other cell types examined. Results shown in FIG. 20A (aFGF) and FIG. 20B (bFGF) illustrate the degree of inhibition. No toxic effects of compound no. 58 were observed for this cell type in this assay.

EXAMPLE 35

This example investigates proliferation of murine thymocytes co-stimulated with ConA and IL-2 using a procedure akin to the procedure in Example 23. In another related assay, inhibitory effects on CT-6 cell proliferation is examined. CT-6 cells are a murine IL-2 dependent, cytotoxic T cell line that proliferate in response to murine IL-2 (15 U/ml). FIGS. 21A, 21B, 21C and 21D illustrate experimental results of both compound no. 35 and CsA in each assay.

Figure 21A:
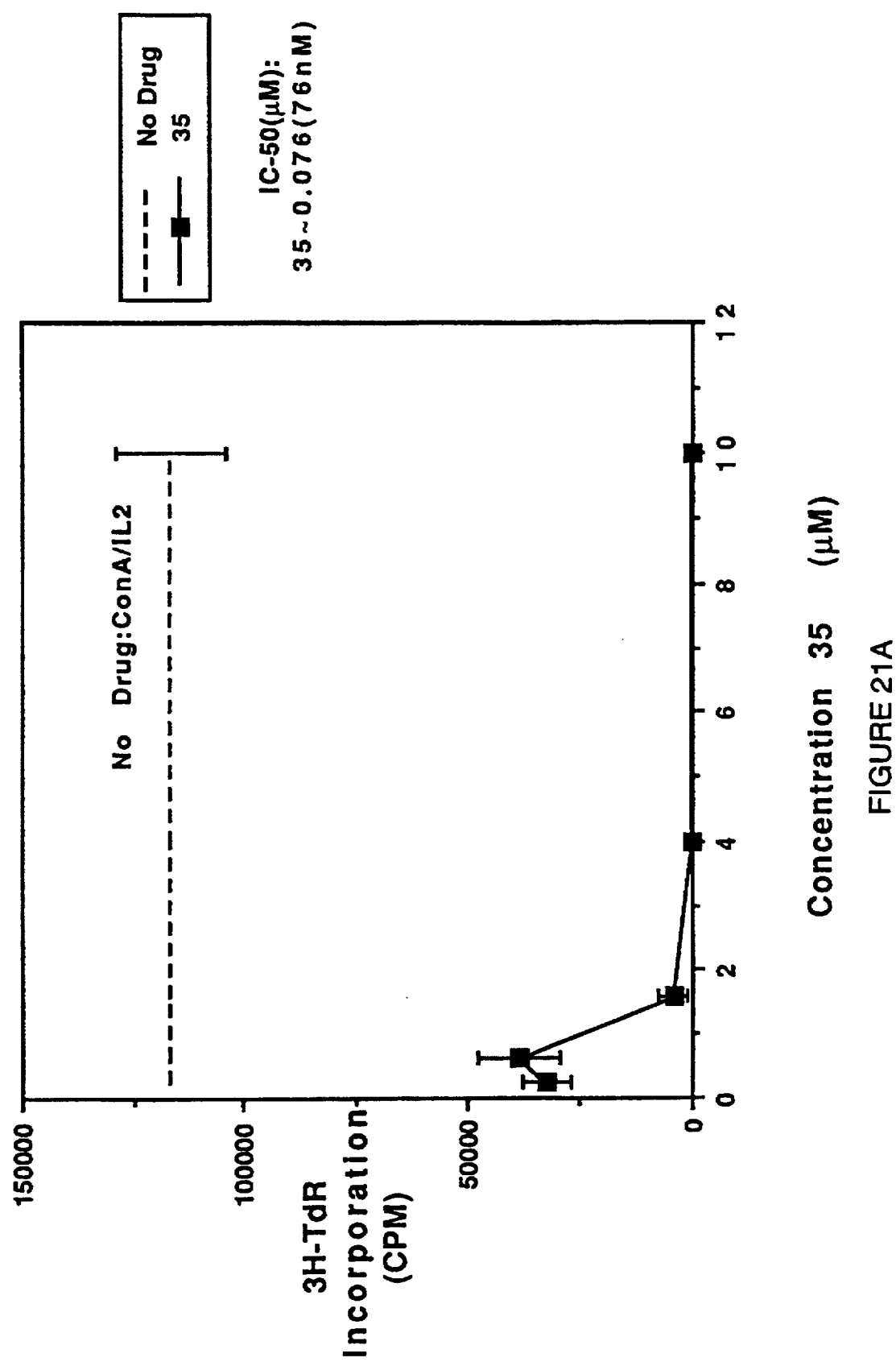
FIGS. 21A and 21B show inhibitory activity of compound no. 35 and CsA, respectively, on murine thymocytes, co-stimulated with ConA and IL-2.
Figure 21B:
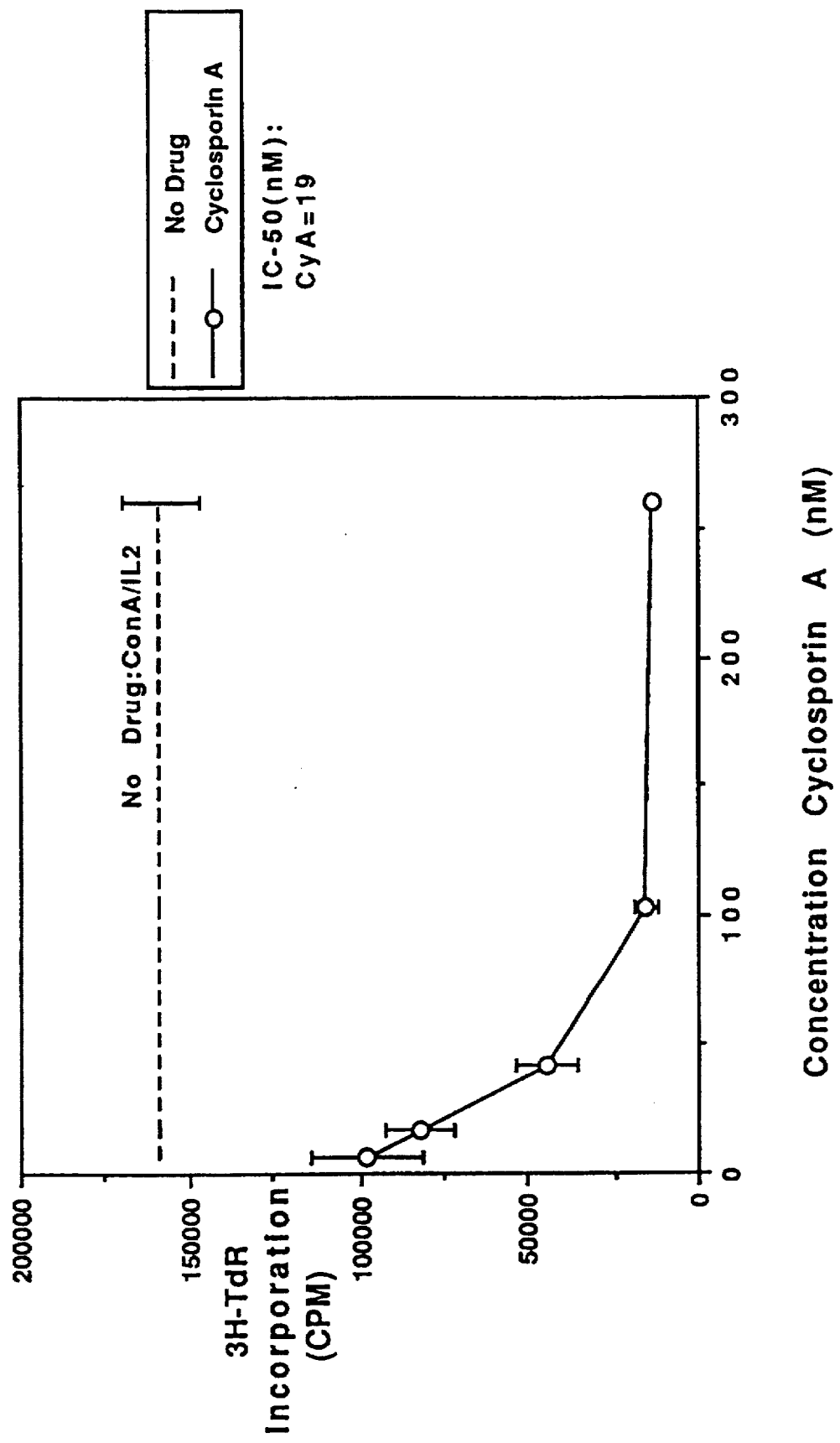
Figure 21C:
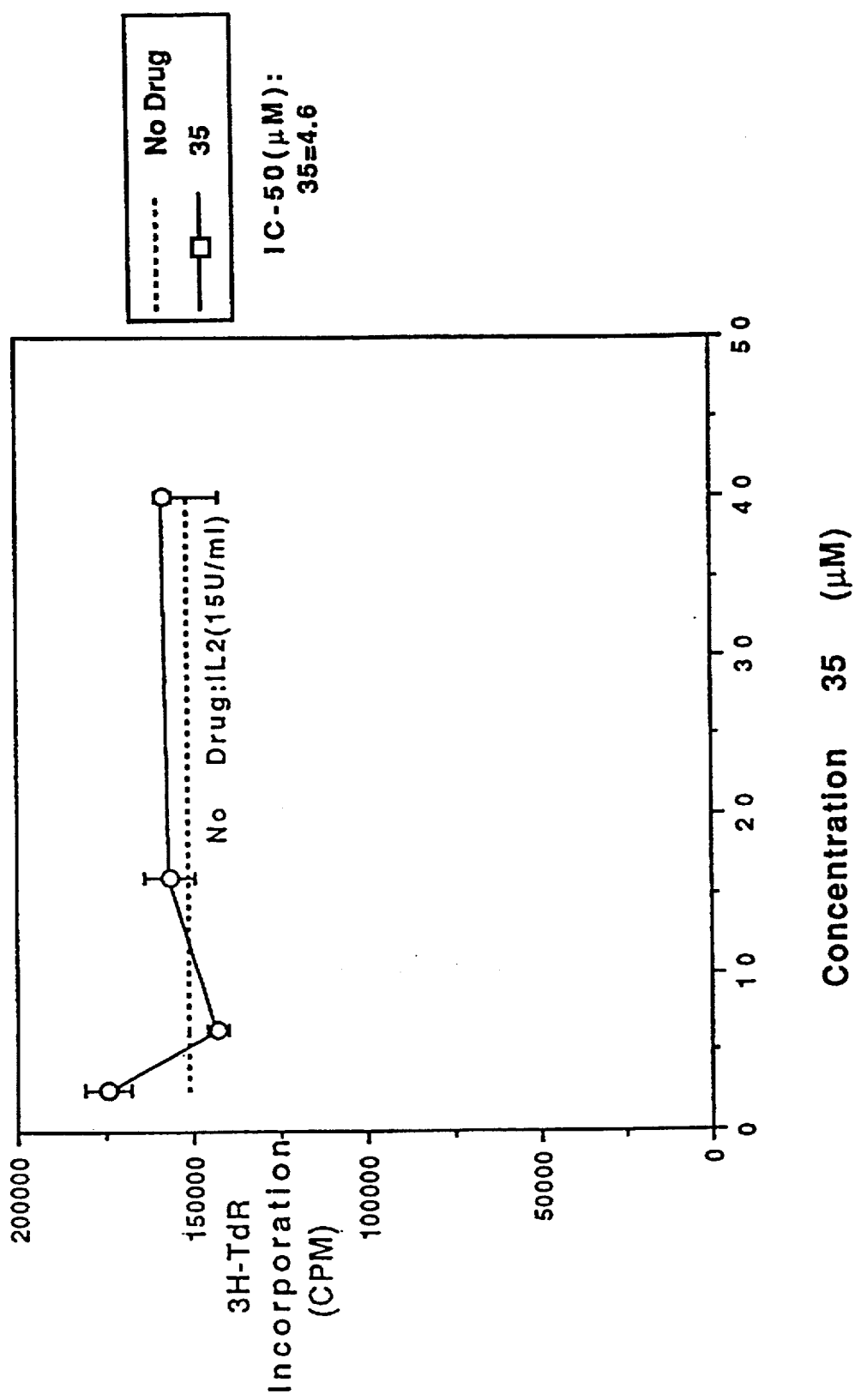
FIGS. 21C and 21D illustrate inhibitory effects of compound no. 35 and CsA, respectively, on IL-2-induced proliferation of cytotoxic CT-6 cells.
Figure 21D:
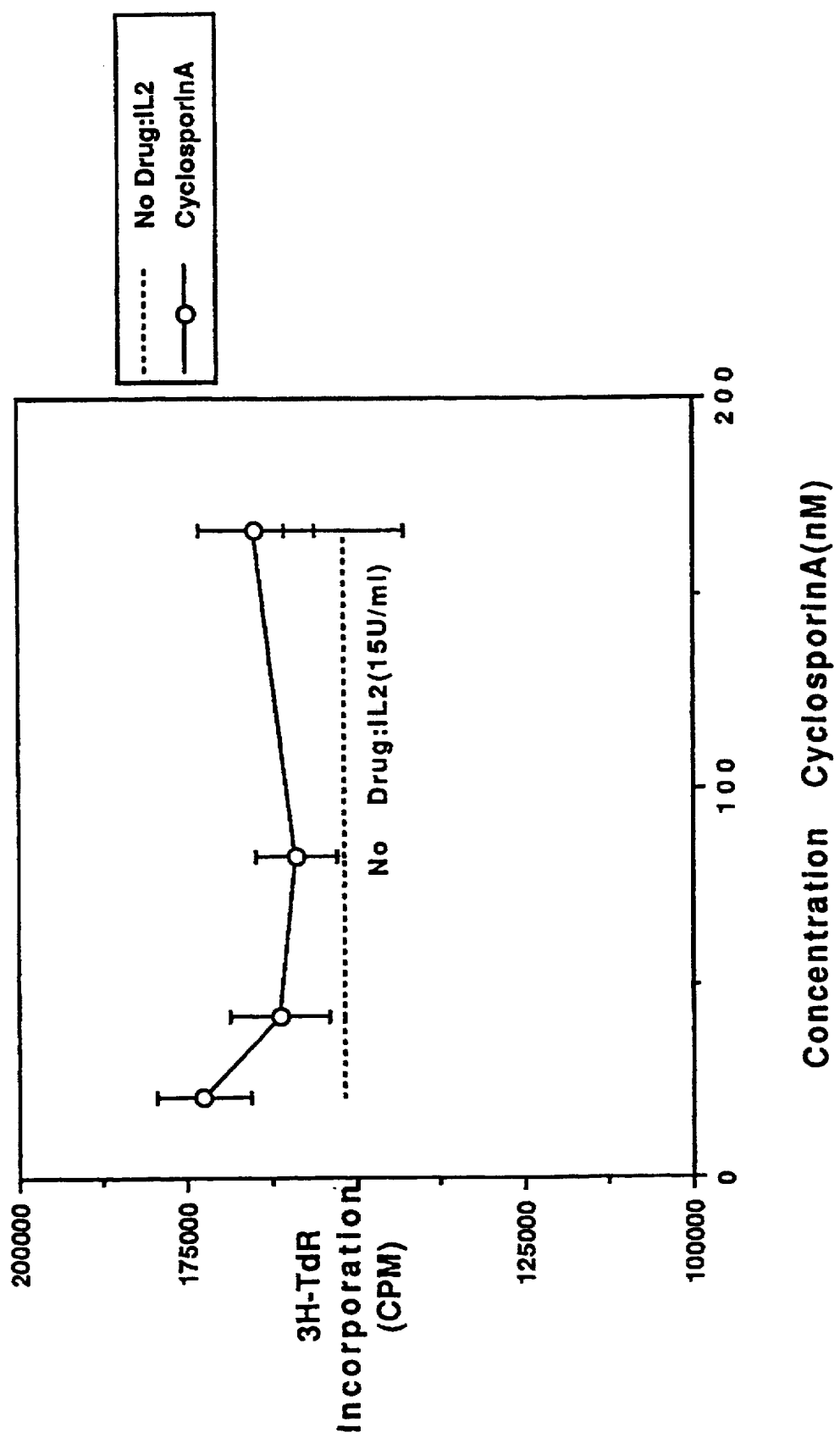

FIG. 21A illustrates the extent of inhibitory activity of compound no. 35 on murine thymocyte co-stimulation and FIG. 21B shows comparative inhibitory activity of CsA. Both exhibit significant inhibition of thymocyte proliferation with IC50 values in the low micro and nanomolar ranges, respectively. FIGS. 21C and 21D illustrate inhibitory effects of compound no. 35 and CsA, respectively. Both compound no. 35 and CsA exhibited no activity in this assay, indicating neither inhibits IL-2-induced proliferation of cytotoxic CT-6 cells.

EXAMPLE 36

Figure 22:
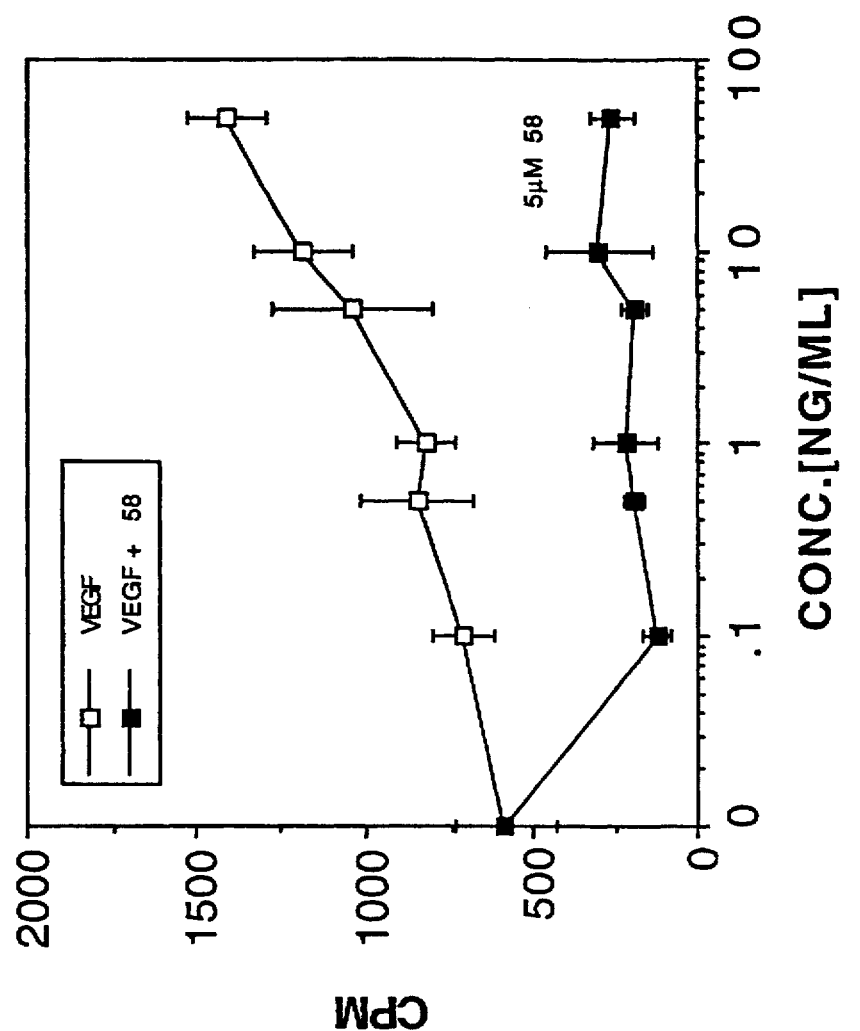
FIG. 22 reports activity results for compound no. 58 on Vascular Endothelial Growth Factor (VEGF)-induced proliferation in a human umbilical vein endothelial cell line (HUVEC).

This example investigates inhibitory effects of compound no. 58 on Vascular Endothelial Growth Factor (VEGF)-induced proliferation in a human umbilical vein endothelial cell line (HUVEC). In this assay procedure, cells were grown in reduced serum (0.5% fetal calf serum) for 24 hours prior to stimulating with various concentrations of VEGF. VEGF has been shown to be important in tumor cell-mediated angiogenesis. Compound no. 58, at 5 µM, inhibited VEGF-induced proliferation at all concentrations of VEGF tested, as shown in FIG. 22.

EXAMPLE 37

Figure 23:
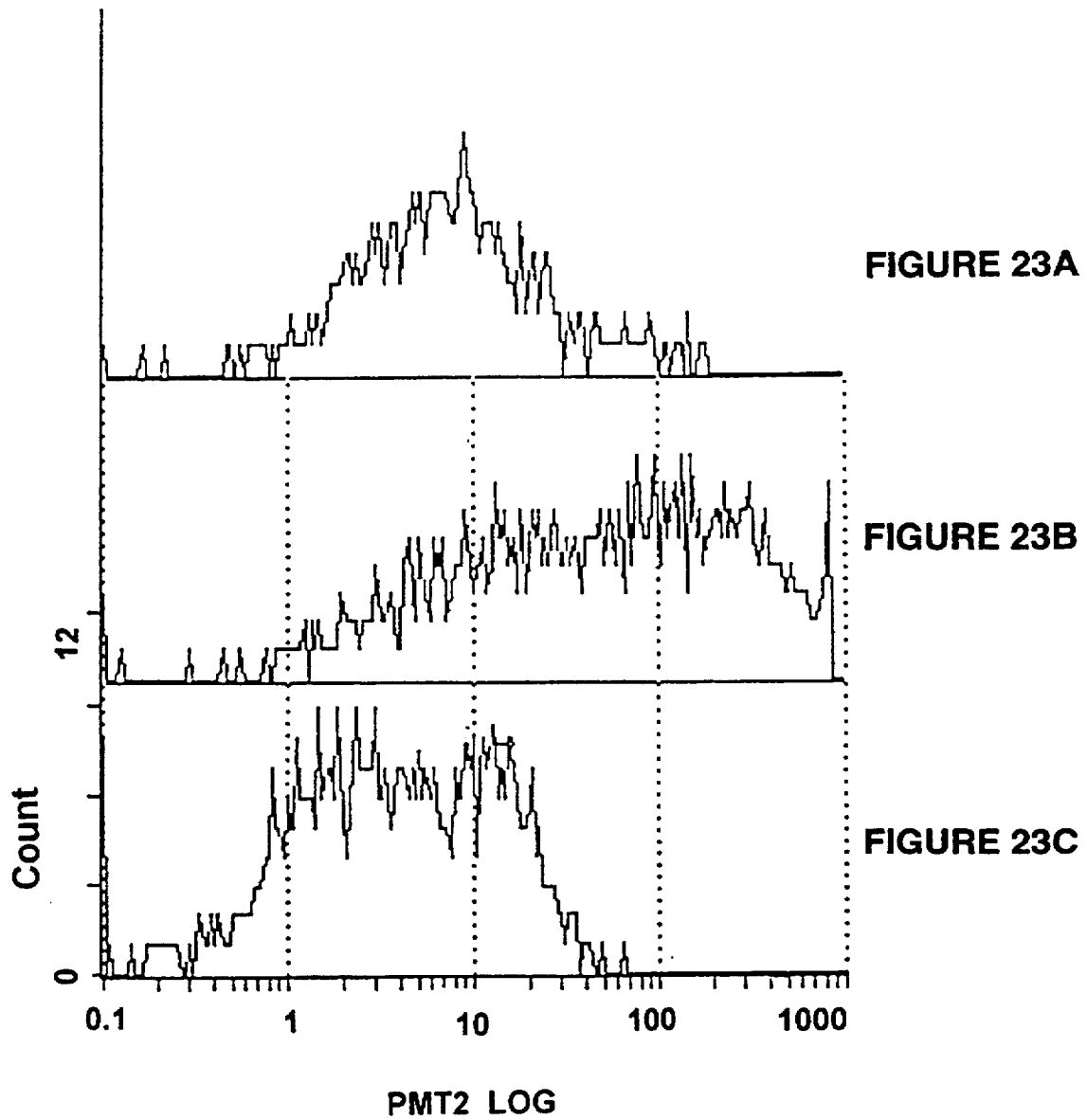
FIG. 23 is a series of frequency histograms obtained in obtained from flow cytometric analysis of HUVEC cells.

This example was used to investigate inhibition of vascular cell adhesion molecule (VCAM) expression on HUVEC by compound no. 58. VCAM expression by endothelial cells is an early event in atherogenesis and multiple sclerosis, among other various autoimmune diseases. FIG. 23 is a series of frequency histograms obtained in this exemplary assay. The top panel shows a frequency histogram obtained from flow cytometric analysis of HUVEC cells stained with an antibody directed against VCAM and a second stem goat anti-mouse-FITC antibody. In the absence of TNF, VCAM expression on HUVEC is at a very low level. The middle panel shows a frequency histogram of cells stimulated with TNF for 6 hours prior to analyzing by flow cytometry. The average increase in cell fluorescence is approximately 10-fold. The bottom panel is a frequency histogram of TNF-stimulated cells in the presence of compound no 58. Presence of inventive compound reduced mean fluorescence by a factor of 8, compared with mean fluorescence from TNF-stimulated cells in the absence of compound no. 58.

EXAMPLE 38

Figure 24:
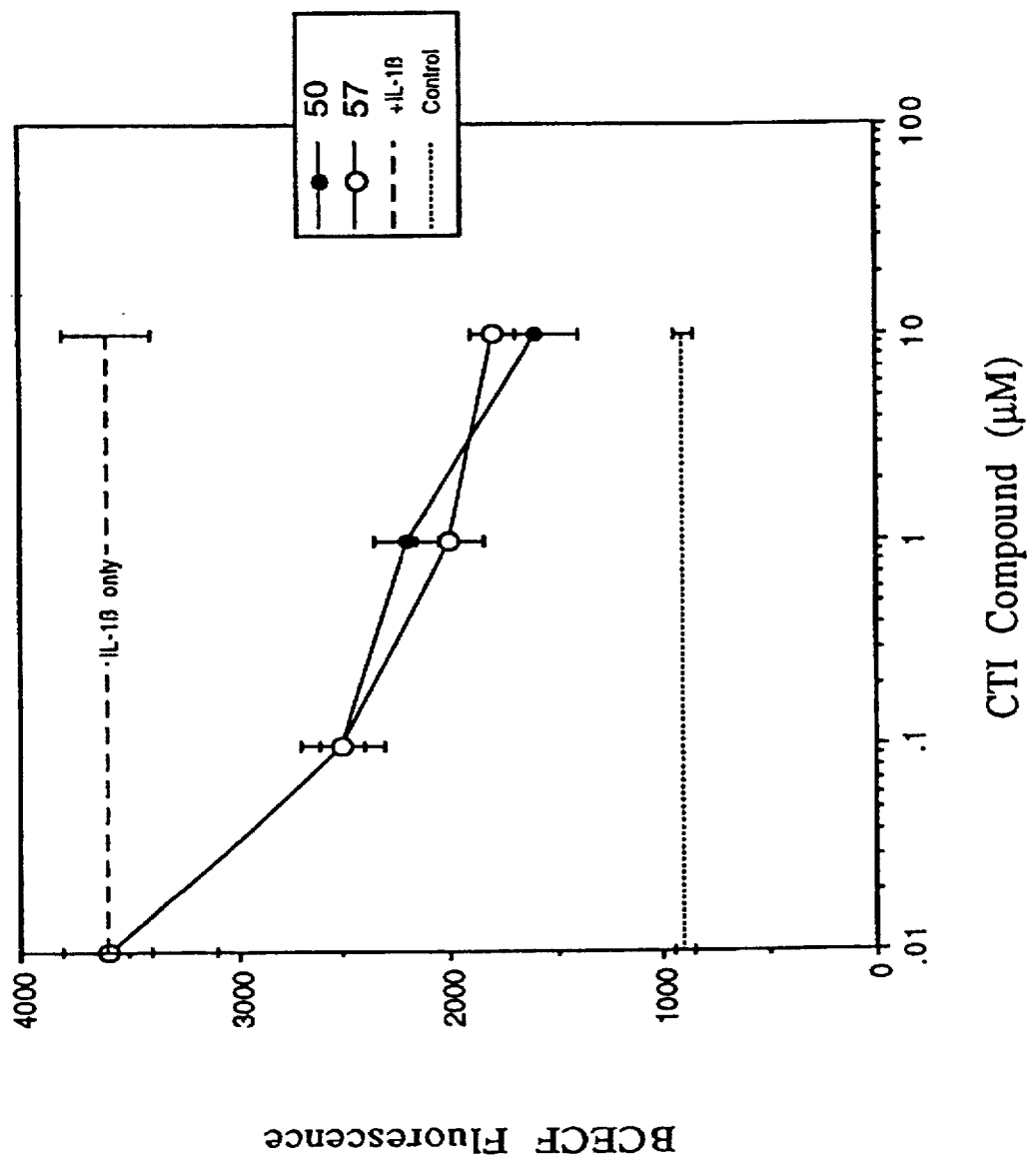
FIG. 24 illustrates inhibitive results obtained for compounds nos. 50 and 57 on THP-1 cell adhesion to IL-1-activated HUVEC.

This example illustrates inhibitive activity of compounds nos. 50 and 57 on THP-1 cell adhesion to IL-1-activated HUVEC. In an investigative assay, HUVEC were stimulated with IL-1 (10 ng/ml), both in the absence and presence of varying concentrations of drugs for 8 hours in a 96-well microtiter plate. In the wellplate, human monocytic leukemia cell line THP-1 celles were added at 50,000 cells per well. The THP-1 cells were pre-incubated with BCECF, a fluorescence dye that can be used to measure cell number using a fluorescence plate reader. After 10 minutes at 37° C., the microtiter plate was inverted and spun at 900 rpm. The remaining adhering THP-1 cells were then analyzed. As shown in FIG. 24, non-stimulated background adherence was approximately 1500 relative units, increasing to approximately 6500 under TNF stimulation. The inventive compounds tested significantly inhibited THP-1 adhesion, even at low concentrations.

EXAMPLE 39

Figure 25A:
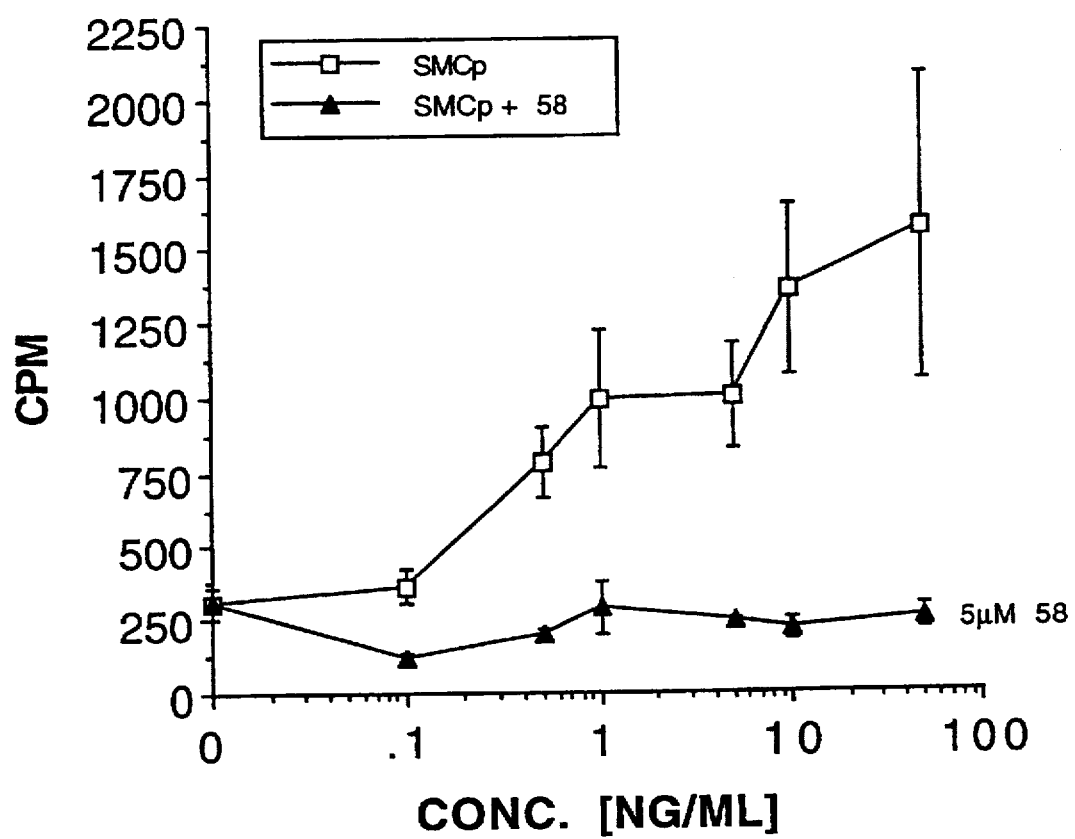
FIGS. 25A and 25B show the effects of compound no. 58 on aFGF and bFGF-induced proliferation in pulmonary smooth muscle cell.
Figure 25B:
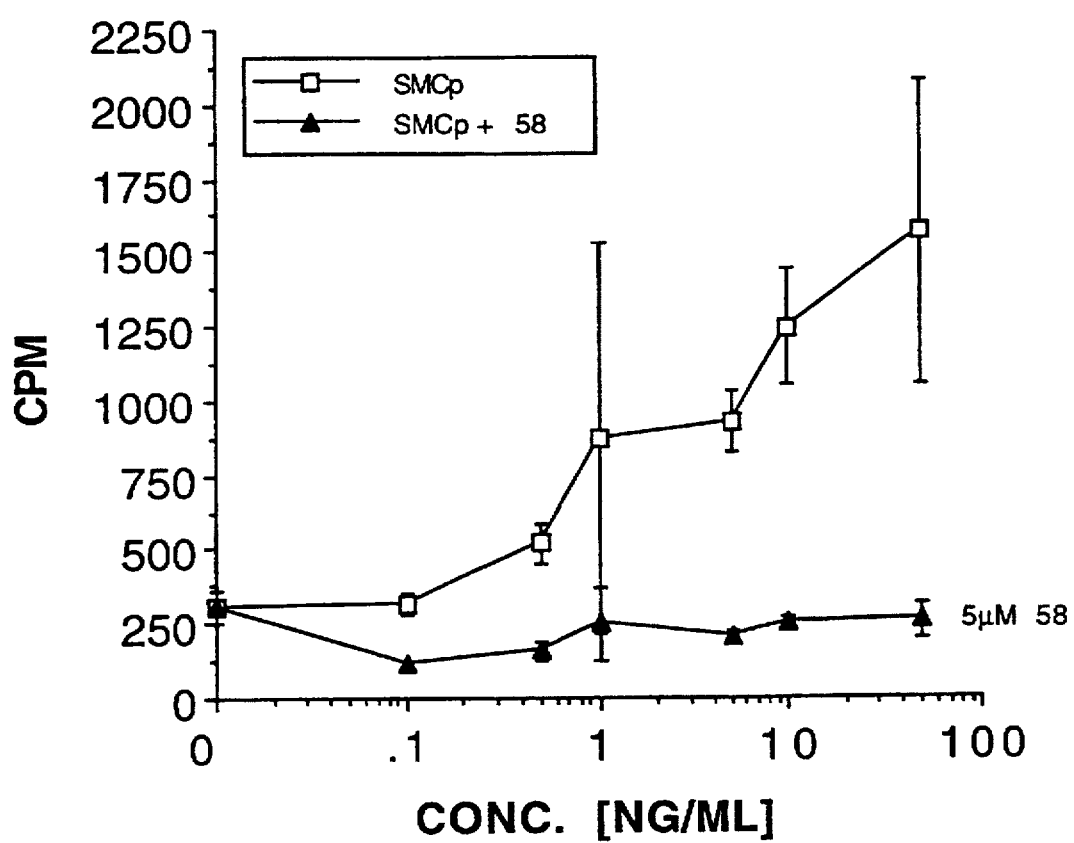

This example shows the inhibitory effect of inventive compound no. 58 on either aFGF or bFGF-induced proliferation in human pulmonary smooth muscle cells. Cells were grown in reduced serum (0.5% fetal calf serum) for 24 hours prior to stimulating with various concentrations of PDGF. Cells, stimulated with either aFGF or bFGF, were analyzed in the presence and absence of compound no. 58 (5 µM). Assay results are reported in FIGS. 25A and 25B (aFGF and bFGF, respectively). As shown in the results, compound no. 58 is a potent inhibitor of both aFGF and bFGF-induced proliferation in this cell type, this pulmonary smooth muscle cell being representative of other cell types examined. No toxic effect of compound no. 58 were observed in this assay.

What is claimed is:

1. A method for treating symptoms of a disease or treatment-induced toxicity selected from the group consisting of: tumor progression resulting from angiogenesis; tumor invasion and metastases formation through adhesion molecule binding; tissue invasion through tumor metalloprotease production; TNF or IL-1-mediated acute allergic reaction; growth factor-induced proliferation of smooth muscle cell, endothelial cell, fibroblast or other cell types; IL-1, MIP-1, PDGF or FGF-induced kidney mesangial cell proliferation; inflammation; Alzheimer's disease; lupus; cyclosporin A or amphotericin B-induced kidney glomerular or tubular toxicity; organ toxicity resulting from cytotoxic therapies and non-alkylating anti-tumor agents; metalloprotease-induced inflammation; bone diseases caused by overproduction of osteoclast-activating factor (OAF) by osteoclasts; septic shock, adult respiratory distress syndrome and multi-organ dysfunction associated with an inflammatory cytokine cascade, the method comprising the step of administering an effective amount of a compound to an individual having the disease or treatment-induced toxicity whereby a cellular response mediated by a second messenger is affected, the compound having a formula:

$$(X)_j\text{—CORE MOIETY}$$

wherein:

j is an integer from one to three, the core moiety comprises a substituted or unsubstituted nitrogen-containing heterocycle having one ring or two fused rings, each ring having five to six ring atoms and X is a racemic mixture, R or S enantiomer, solvate, hydrate, or salt of:

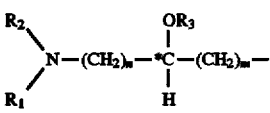

wherein:

*C is a chiral carbon atom;

n is an integer from one to four;

one or more carbon atoms of $(CH_2)_n$ may be substituted by a carbonyl or hydroxyl group;

m is an integer from four to fourteen;

independently, $R_1$ and $R_2$ are hydrogen, a straight or branched chain alkyl or alkenyl group of up to twelve carbon atoms in length, or —$(CH2)_wR_5$, w being an integer from two to fourteen and $R_5$ being a mono-, di- or tri-substituted or unsubstituted aryl group, substituents on $R_5$ being selected from the group consisting of hydroxyl, chloro, fluoro, bromo, or $C_{1-6}$ alkoxyl, or a substituted or unsubstituted, saturated or unsaturated heterocyclic group having from four to seven carbon atoms; or $R_1$ and $R_2$ jointly form a substituted or unsubstituted, saturated or unsaturated heterocyclic group having from four to seven carbon atoms, N being a hetero atom; and $R_3$ is hydrogen or $C_{1-3}$; or jointly one of $R_1$ or $R_2$ and $R_3$ form a substituted or unsubstituted linking carbon chain, having from one to four carbon atoms, joining the O and N in a cyclic structure, an integer sum equal to n+a number of carbon atoms in the linking carbon chain being less than six; and wherein a ring atom of the core moiety is attached to a terminal carbon atom of $(CH_2)_m$.

2. The method of claim 1, wherein n is an integer from one to three.

3. The method of claim 1, wherein m is an integer from ten to fourteen.

4. The method of claim 1, wherein the ring atom of the core moiety is a nitrogen atom.

5. The method of claim 1, wherein the core moiety is a member selected from the group consisting of substituted or unsubstituted: barbituric acid; benzamido; flutarimidyl; glutarimidyl; homophthalimidyl; imidazolylamido; isocarbostyrilyl; lumazinyl; pteridinyl; pthalimidyl; piperidinyl; pyridinyl; pyrimidinyl; pyrrolylamido; quinazolinedionyl; quinazolinonyl; quinolonyl; succinimidyl; theobrominyl; thyminyl; triazinyl; uracil and xanthinyl.

6. The method of claim 1, wherein the core moiety is selected from the group consisting of glutarimidyl, methylthyminyl, methyluracil, thyminyl, theobrominyl, uracil and xanthinyl.

7. The method of claim 6, wherein the core moiety is xanthinyl, the terminal carbon atom of $(CH_2)_n$ is attached to the $N_1$ xanthinyl nitrogen and $N_3$ and $N_7$ xanthinyl nitrogens are independently substituted by a member selected from the group consisting of hydrogen, methyl, fluoro, chloro and amino.

8. The method of claim 6, wherein the core moiety is glutarimidyl.

9. The method of claim 6, wherein the core moiety is uracil and the terminal carbon atom of $(CH_2)_n$ is attached to a uracil nitrogen atom.

10. The method of claim 6, wherein the core moiety is methylthyminyl or thyminyl and the terminal carbon atom of $(CH_2)_n$ is attached to a nitrogen atom.

11. The method of claim 1, wherein the core moiety is selected from the group consisting of 1-methyllumazinyl; methylbarbituric acid; 3,3-dimethylflutarimidyl; 2-hydroxypyridinyl; methyldihydroxypyrazolopyrimidinyl; methylpyrrolopyrimidinyl; 2-pyrrolylamido; 3-pyrrolylamido; 1,2,3,4-tetrahydroisoquinolonyl; 1-methyl-2,4(1H,3H)-quinazolinedionyl quinazolin-4(3-H)-onyl; alkyl-substituted $(C_{1-6})$ thyminyl; methylthyminyl; alkyl-substituted $(C_{1-6})$ uracil; 6-aminouracil; 1-methyl-5,6-dihydrouracil; 1-methyluracil; 5- and/or 6-position substituted uracils; 1,7-dimethylxanthinyl; 3,7-dimethylxanthinyl; 3-methylxanthinyl; 3-methyl-7-methylpivaloylxanthinyl; 8-amino-3-methylxanthinyl; and 7-methylhypoxanthinyl.

12. The method of claim 11, wherein the methyldihydroxypyrazolopyrimidinyl is 1,3-dimethyldihydroxypyrazolo[4,3-d]pyrimidinyl.

13. The method of claim 11, wherein the methylpyrrolopyrimidinyl is 1-methylpyrrolo[2,3-d]pyrimidinyl.

14. The method of claim 1, wherein the compound is has a formula selected from the group consisting of:

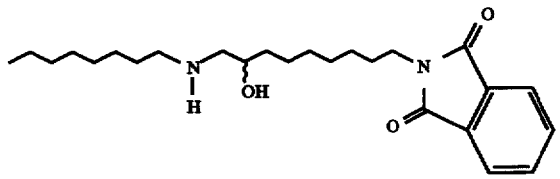

,

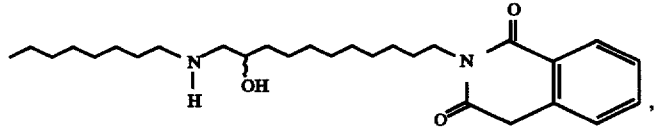

,

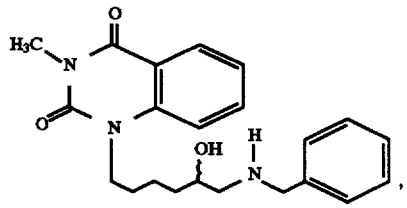

,

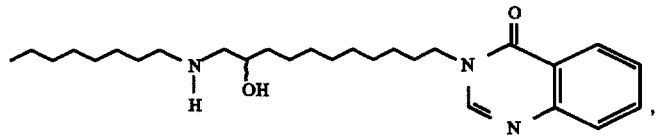

,

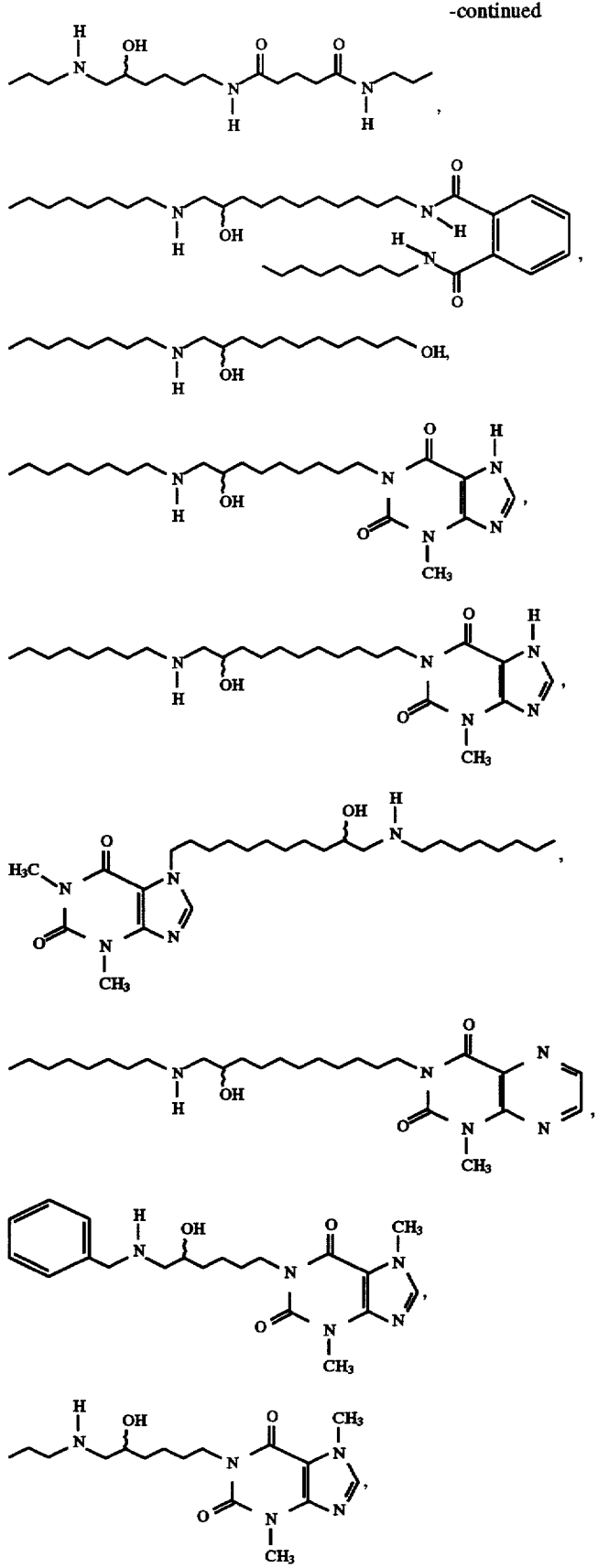

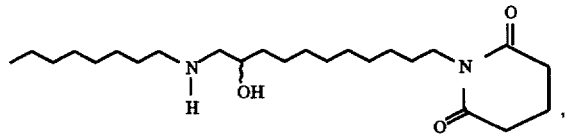
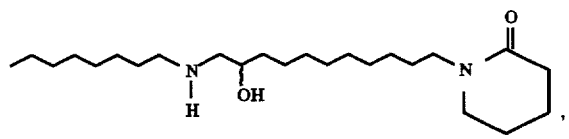
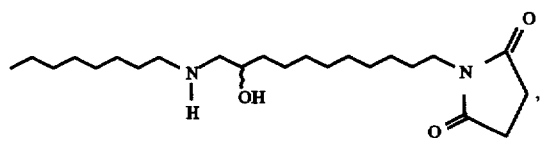
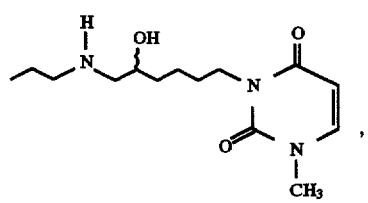
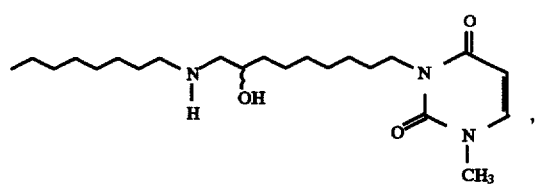
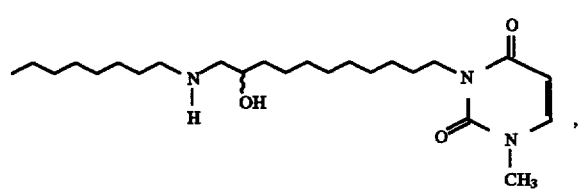
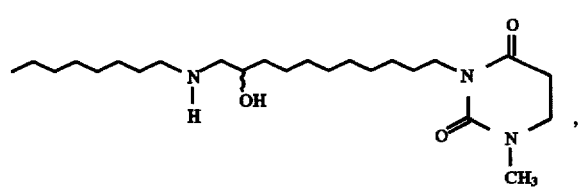
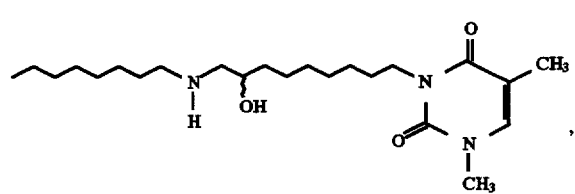
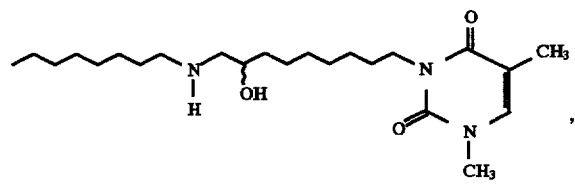

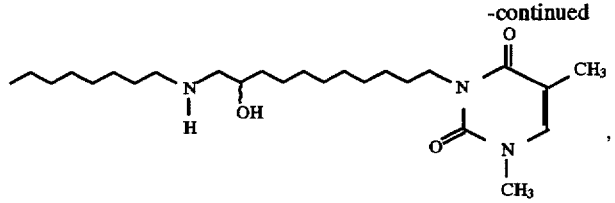
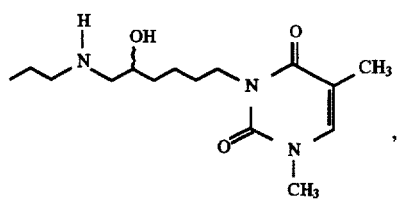
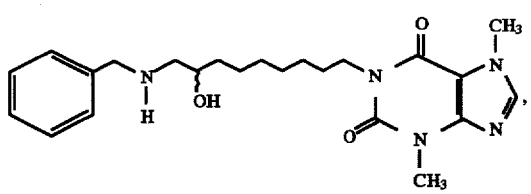
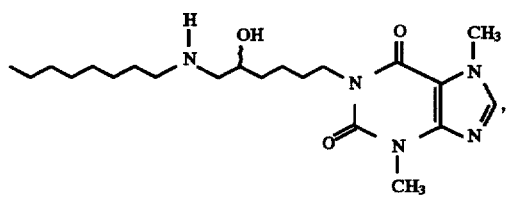
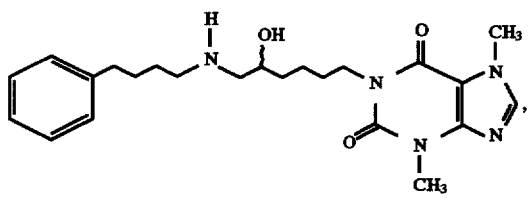
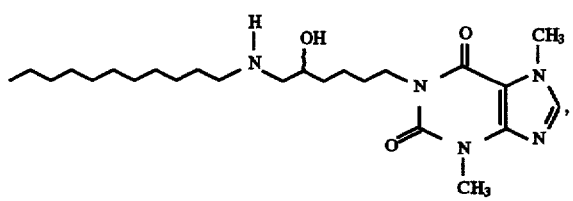
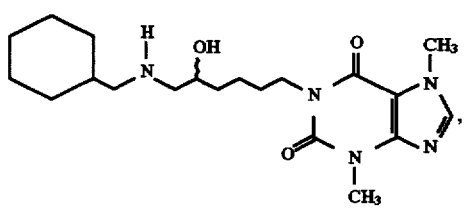
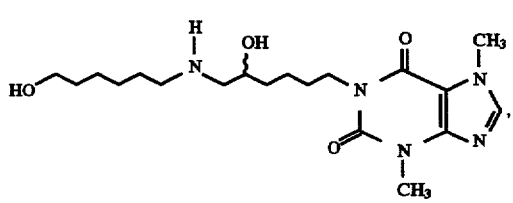

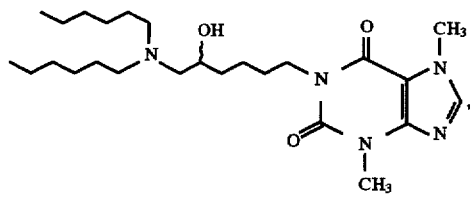
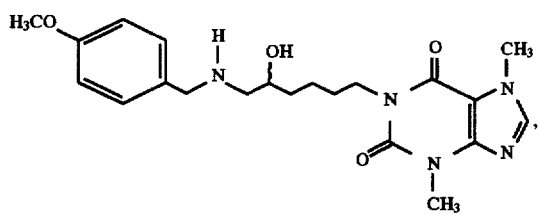
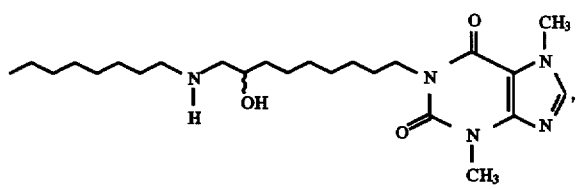
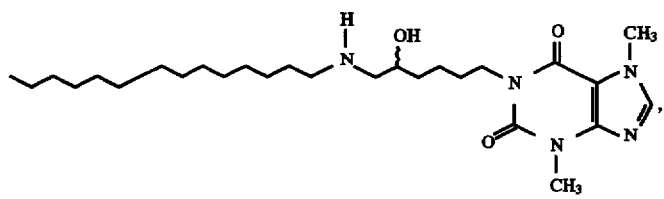
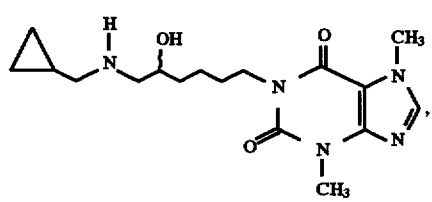
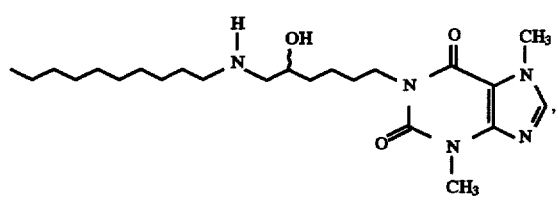
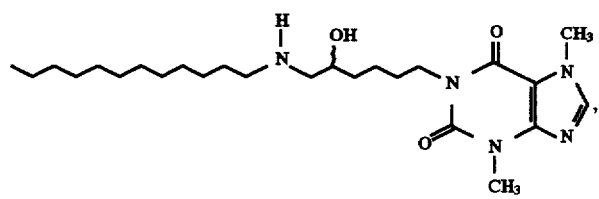
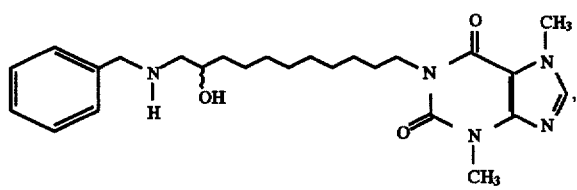

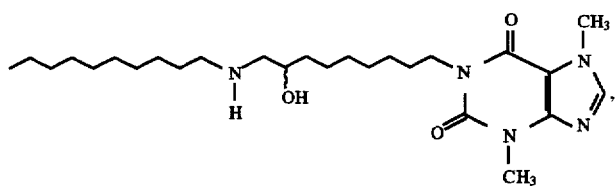
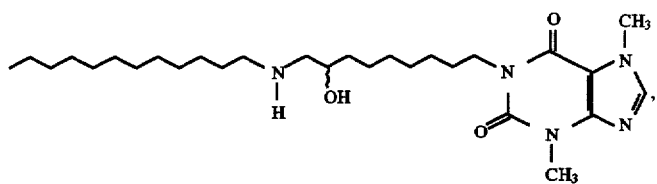
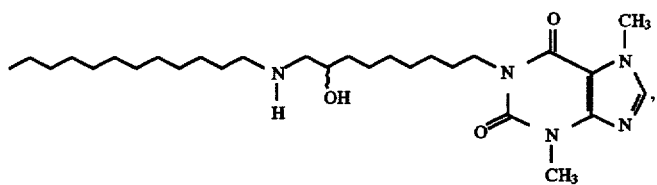
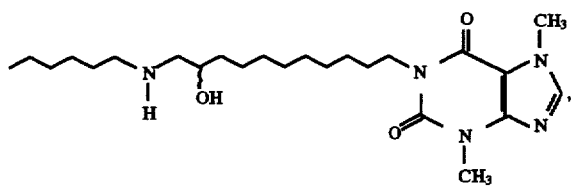
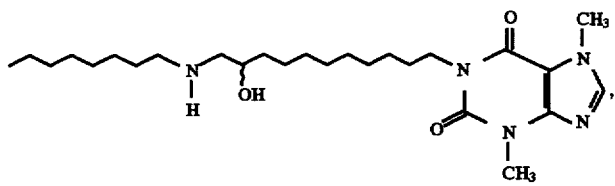
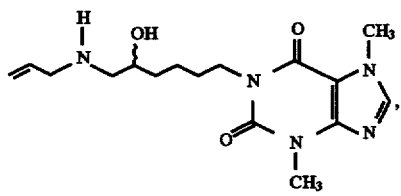
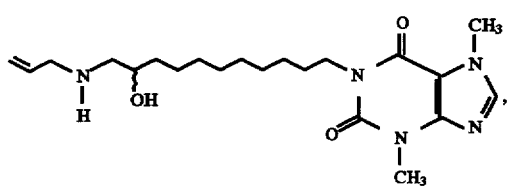
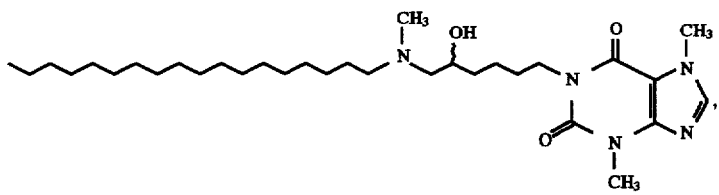

-continued
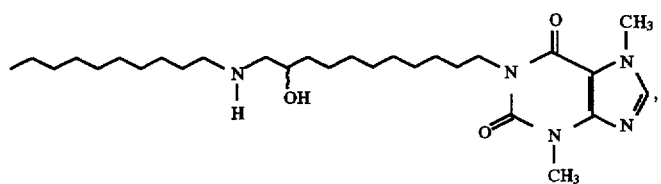
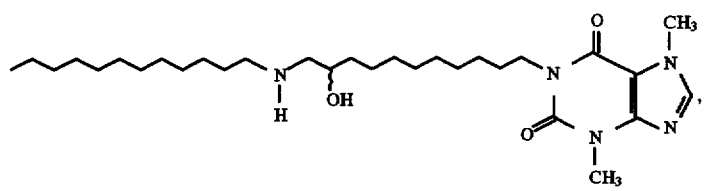
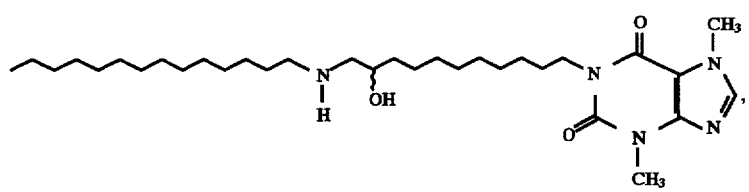
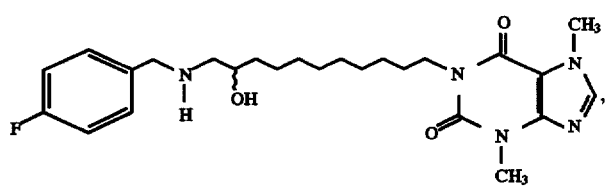
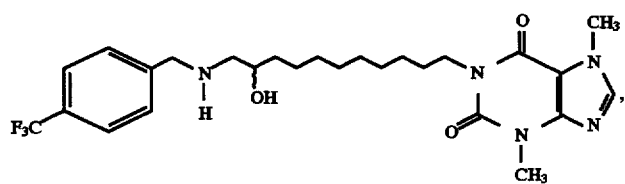
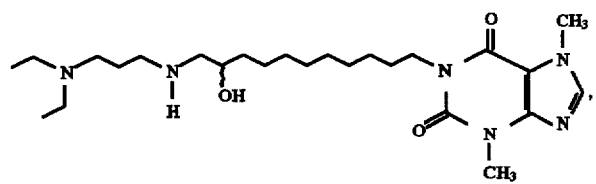
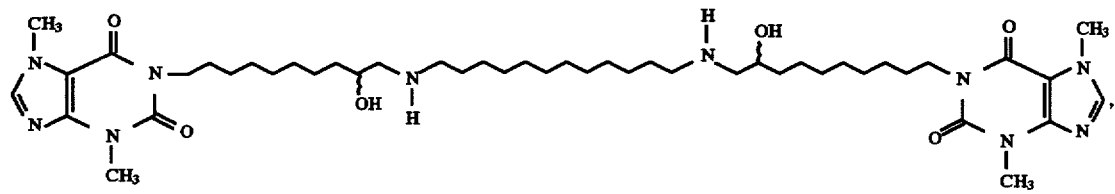
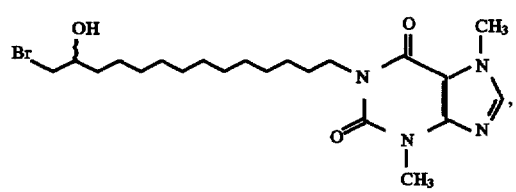

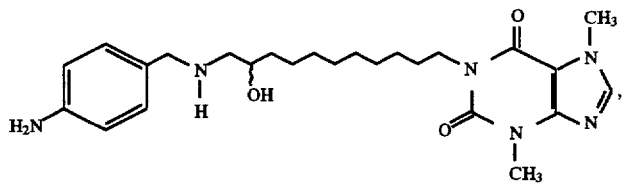
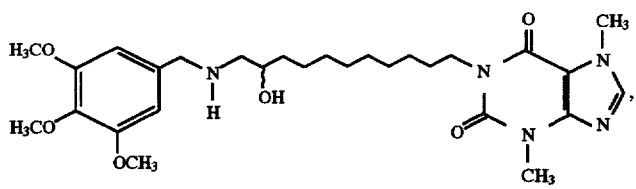
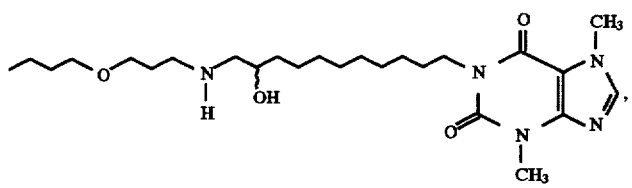
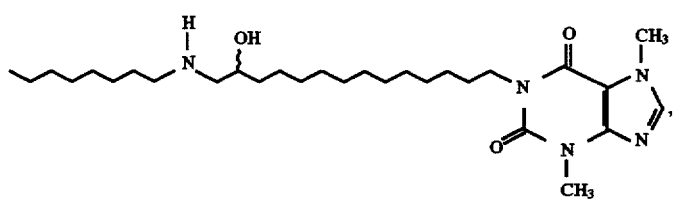
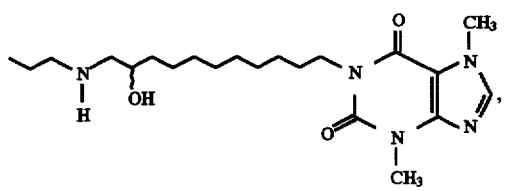
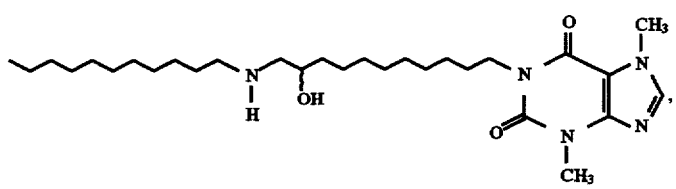
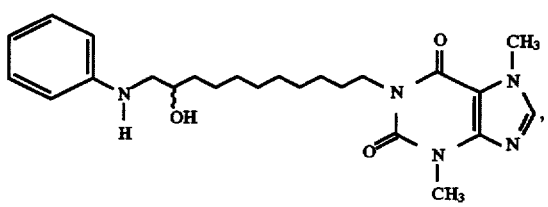
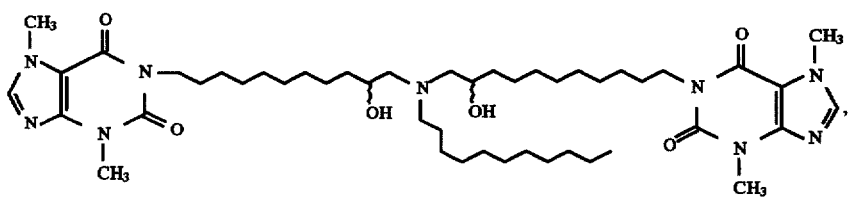

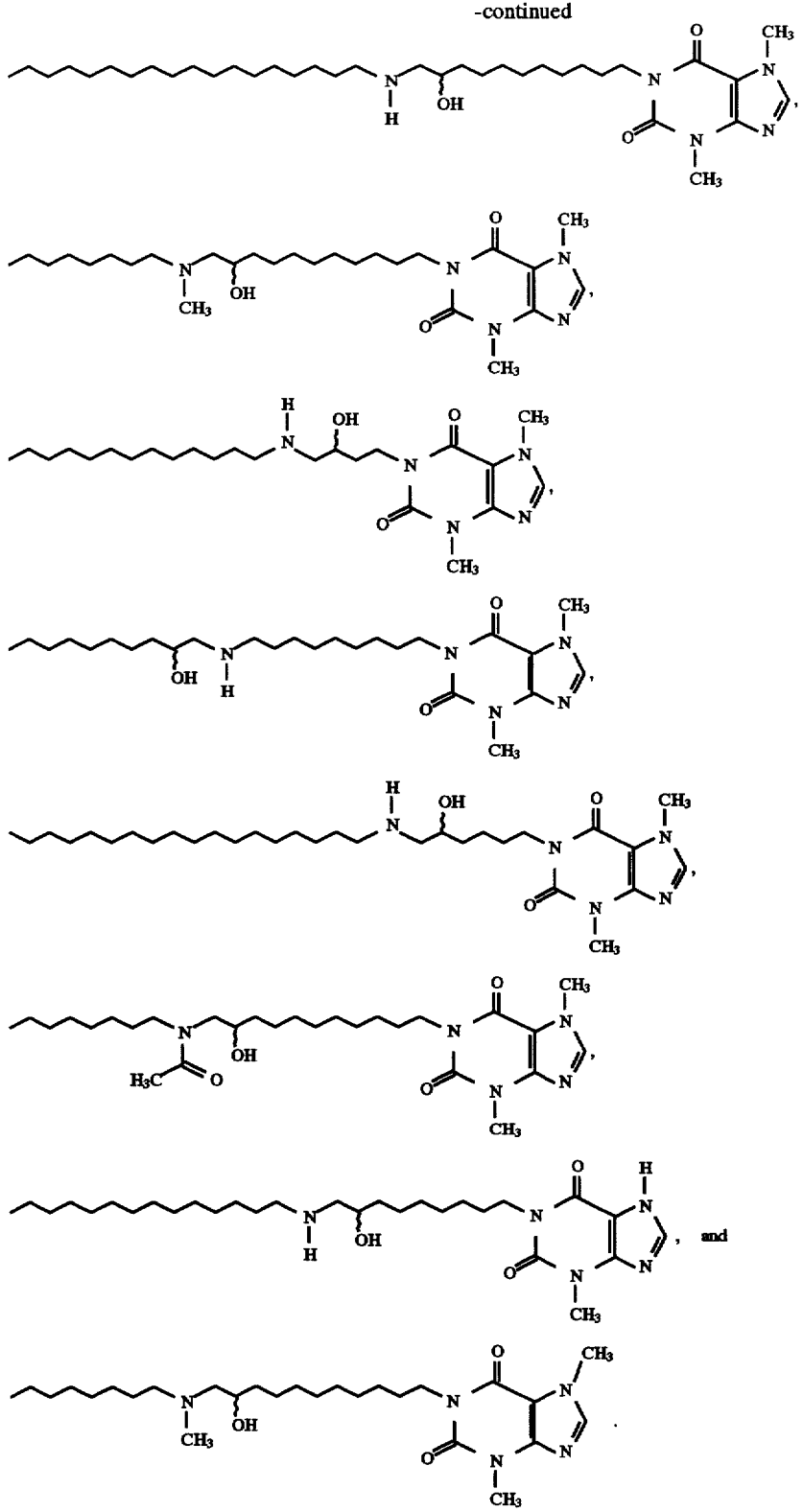
15. The method of claim 1, wherein the ring atom of the core moiety is a nitrogen atom.
16. The method of claim 1, wherein m is an integer from seven to fourteen.
17. A method for treating symptoms of an autoimmune disease selected from the group consisting of insulin-dependent diabetes mellitus (IDDM), multiple sclerosis, psoriasis, asthma, periodontal disease, osteoporosis, alcoholic hepatitis, premature labor secondary to uterine infection an autoimmune thyroiditis, the method comprising administering an effective amount of a compound to an individual suffering from the autoimmune disease whereby a cellular response mediated by a second messenger is affected, the compound having a formula:

(X)j—CORE MOIETY wherein:

j is an integer from one to three, the core moiety comprises a substituted or unsubstituted nitrogen-containing heterocycle having one ring or two fused rings, each ring having five to seven ring atoms and X is a racemic mixture, R or S enantiomer, solvate, hydrate, or salt of:

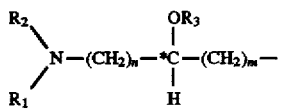

wherein:

*C is a chiral carbon atom; n is an integer from one to four;

one or more carbon atoms of $(CH_2)_n$ may be substituted by a carbonyl or hydroxyl group;

m is an integer from four to fourteen;

independently, $R_1$ and $R_2$ are hydrogen, a straight or branched chain alkyl or alkenyl group of up to twelve carbon atoms in length, or $-(CH_2)_w R_5$, w being an integer from two to fourteen and $R_5$ being a mono-, di- or tri-substituted or unsubstituted aryl group, substituents on $R_5$ being selected from the group consisting of hydroxyl, chloro, fluoro, bromo, or $C_{1-6}$ alkoxyl or a substituted or unsubstituted, saturated or unsaturated heterocyclic group having from four to seven carbon atoms; or $R_1$ and $R_2$ jointly form a substituted or unsubstituted, saturated or unsaturated heterocyclic group having from four to seven carbon atoms, N being a hetero atom; and $R_3$ is hydrogen or $C_{1-3}$; or jointly one of $R_1$ or $R_2$ and $R_3$ form a substituted or unsubstituted linking carbon chain, having from one to four carbon atoms, joining the O and N in a cyclic structure, an integer sum equal to n+a number of carbon atoms in the linking carbon chain being less than six; and wherein a ring atom of the core moiety is attached to a terminal carbon atom of $(CH_2)_m$.

18. The method of claim 17, wherein n is an integer from one to three.

19. The method of claim 17, wherein m is an integer from seven to fourteen.

20. The method of claim 17, wherein m is an integer from ten to fourteen.

21. The method of claim 17, wherein the core moiety is a member selected from the group consisting of substituted or unsubstituted: barbituric acid; benzamido; flutarimidyl; glutarimidyl; homophthalimidyl; imidazolylamido; isocarbostyrilyl; lumazinyl; pteridinyl; pthalimidyl; piperidinyl; pyridinyl; pyrimidinyl; pyrrolylamido; quinazolinedionyl; quinazolinonyl; quinolonyl; succinimidyl; theobrominyl; thyminyl; triazinyl; uracil and xanthinyl.

22. The method of claim 17, wherein the core moiety is selected from the group consisting of glutarimidyl, methylthyminyl, methyluracil, thyminyl, theobrominyl, uracil and xanthinyl.

23. The method of claim 22, wherein the core moiety is xanthinyl, the terminal carbon atom of $(CH_2)_n$ is attached to the $N_1$ xanthinyl nitrogen and $N_3$ and $N_7$ xanthinyl nitrogens are independently substituted by a member selected from the group consisting of hydrogen, methyl, fluoro, chloro and amino.

24. The method of claim 22, wherein the core moiety is glutarimidyl.

25. The method of claim 22, wherein the core moiety is uracil and the terminal carbon atom of $(CH_2)_n$ is attached to a uracil nitrogen atom.

26. The method of claim 22, wherein the core moiety is methylthyminyl or thyminyl and the terminal carbon atom of $(CH_2)_n$ is attached to a nitrogen atom.

27. The method of claim 17, wherein the core moiety is selected from the group consisting of 1-methyllumazinyl; methylbarbituric acid; 3,3-dimethylflutarimidyl; 2-hydroxypyridinyl; methyldihydroxypyrazolopyrimidinyl; methylpyrrolopyrimidinyl; 2-pyrrolylamido; 3-pyrrolylamido; 1,2,3,4-tetrahydroisoquinolonyl; 1-methyl-2,4(1H,3H)-quinazolinedionyl; quinazolin-4(3H)-onyl; alkyl-substituted $(C_{1-6})$ thyminyl; methylthyminyl; alkyl-substituted $(C_{1-6})$ uracil; 6-aminouracil; 1-methyl-5,6-dihydrouracil; 1-methyluracil; 5- and/or 6-position substituted uracils; 1,7-dimethylxanthinyl; 3,7-dimethylxanthinyl; 3-methylxanthinyl; 3-methyl-7-methylpivaloylxanthinyl; 8-amino-3-methylxanthinyl; and 7-methylhypoxanthinyl.

28. The method of claim 27, wherein the methyldihydroxypyrazolopyrimidinyl is 1,3-dimethyldihydroxypyrazolo[4,3-d]pyrimidinyl.

29. The method of claim 27, wherein the methylpyrrolopyrimidinyl is 1-methylpyrrolo[2,3-d]pyrimidinyl.

30. The method of claim 17, wherein the compound has a formula selected from the group consisting of:

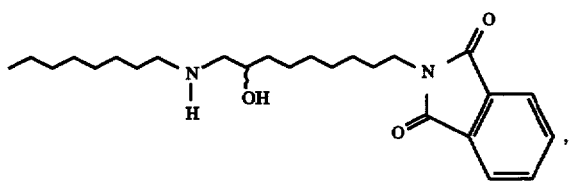

-continued
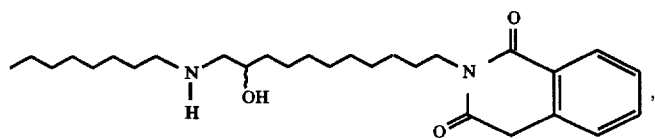
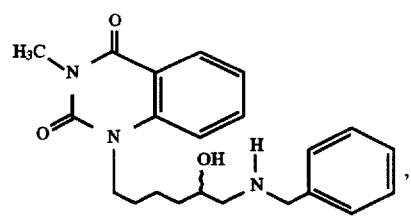
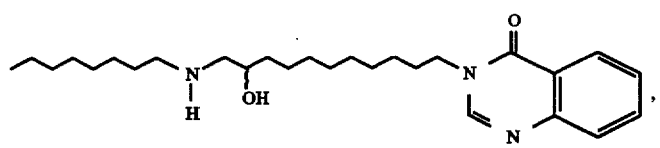
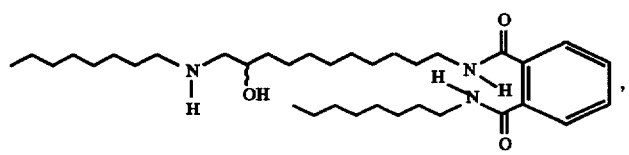
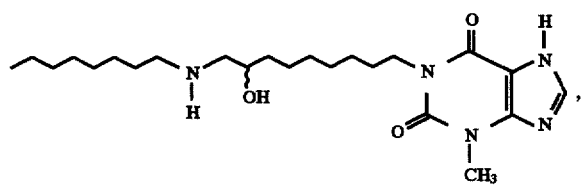
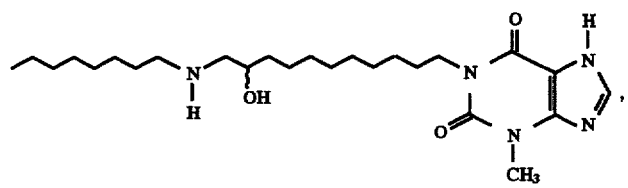
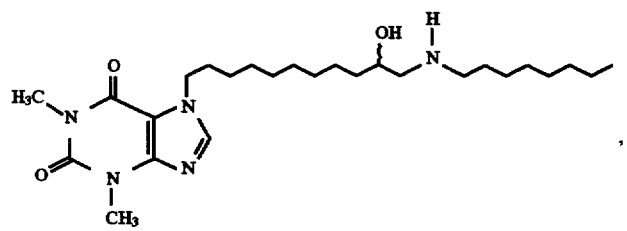
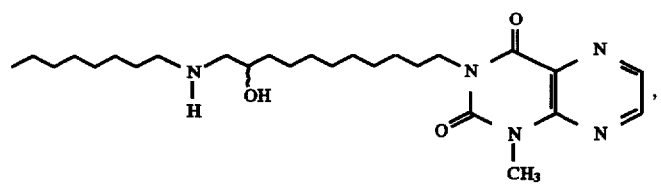

-continued
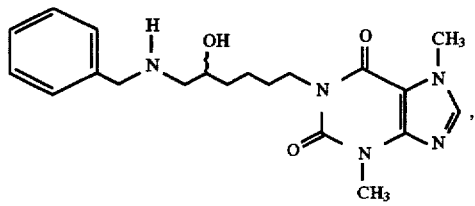
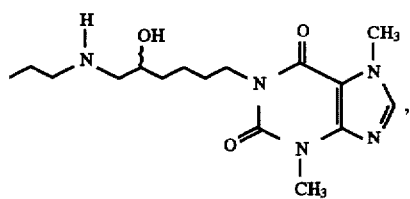
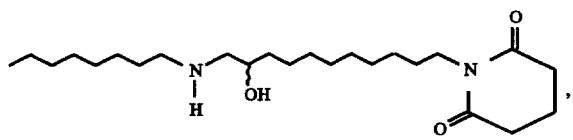
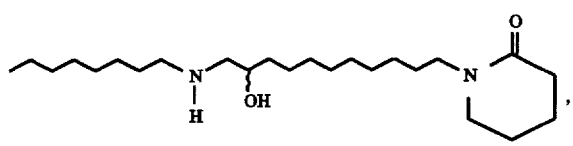
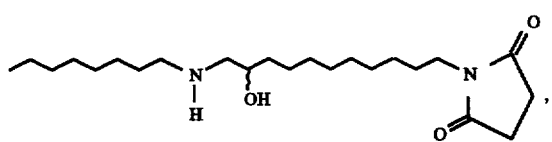
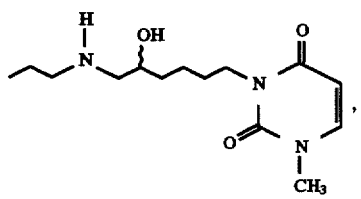
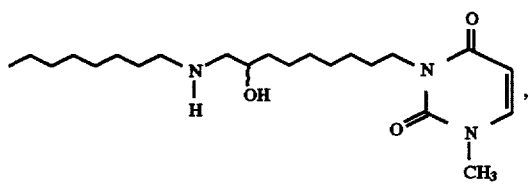
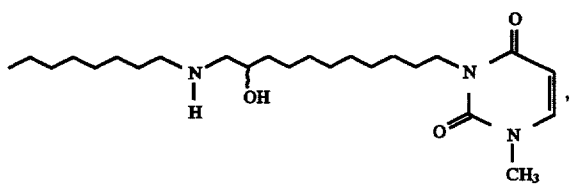
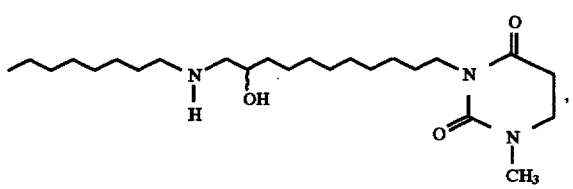

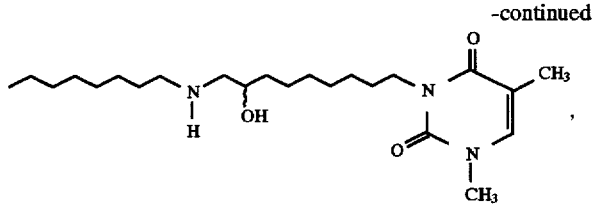,
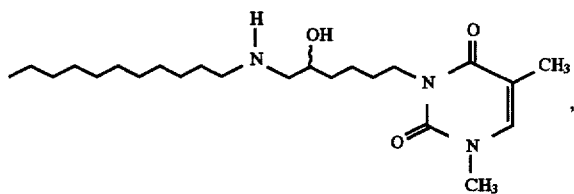,
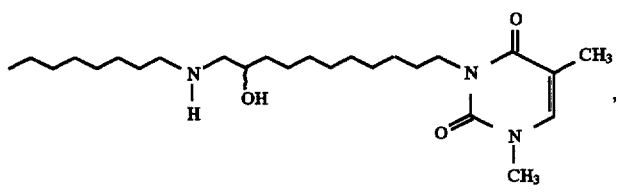,
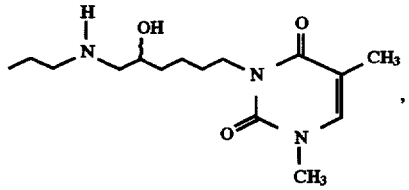,
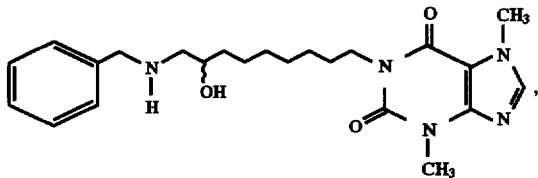,
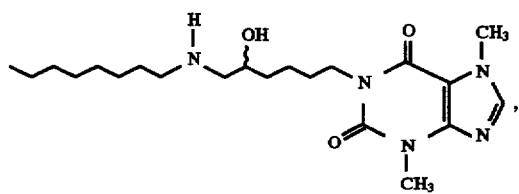,
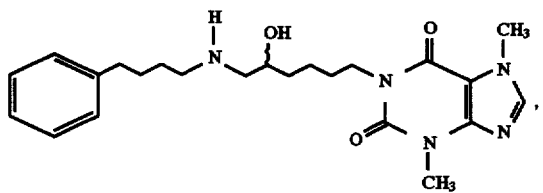,
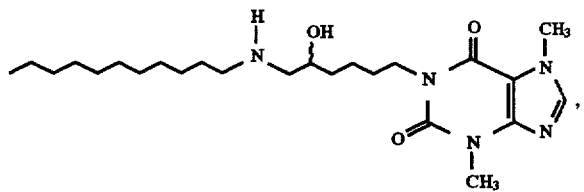, -continued
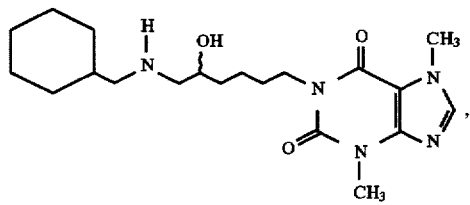
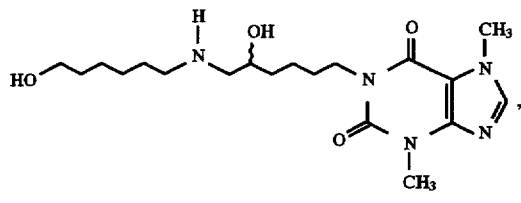
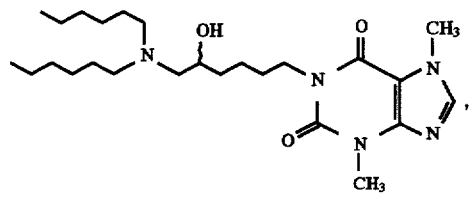
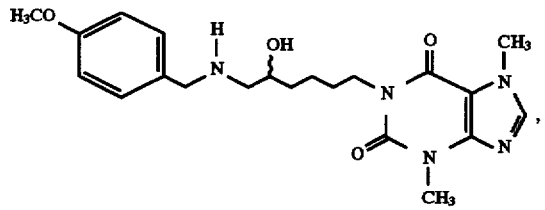
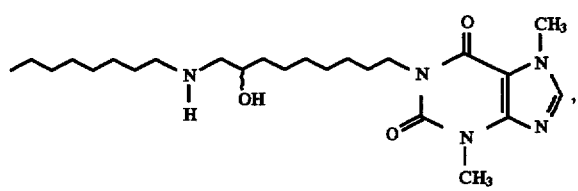
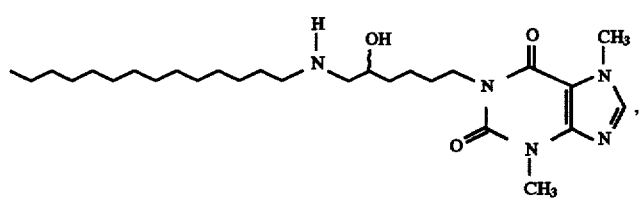
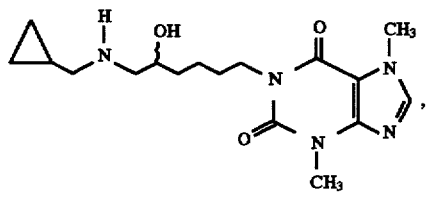
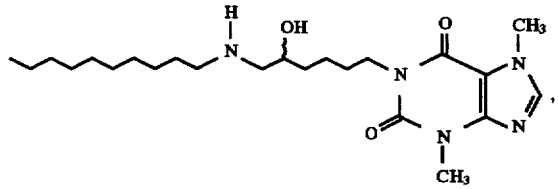

-continued
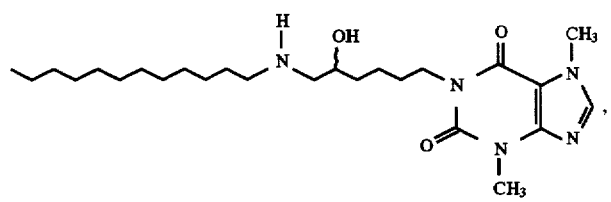
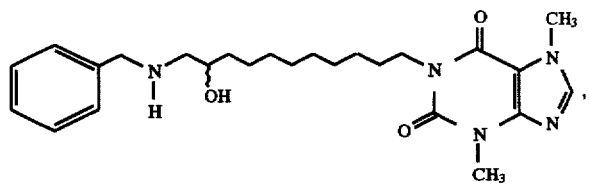
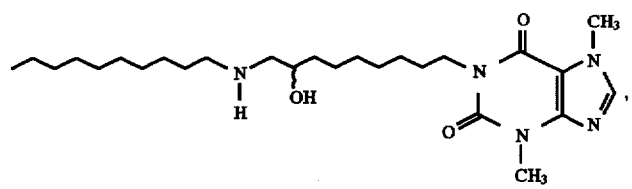
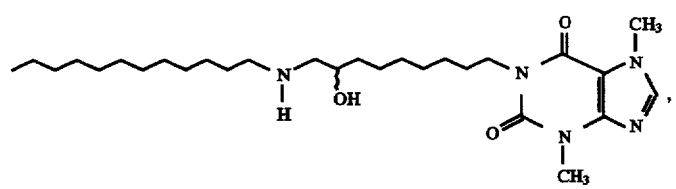
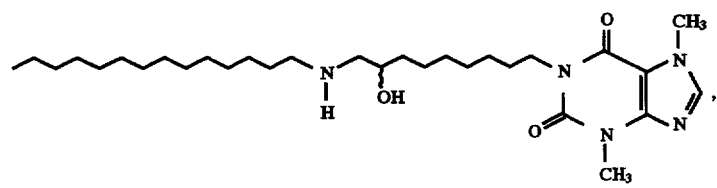
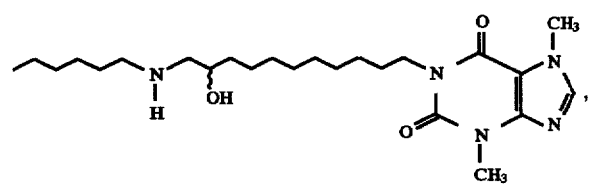
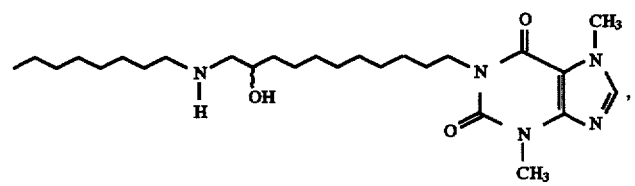
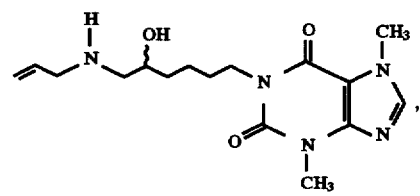

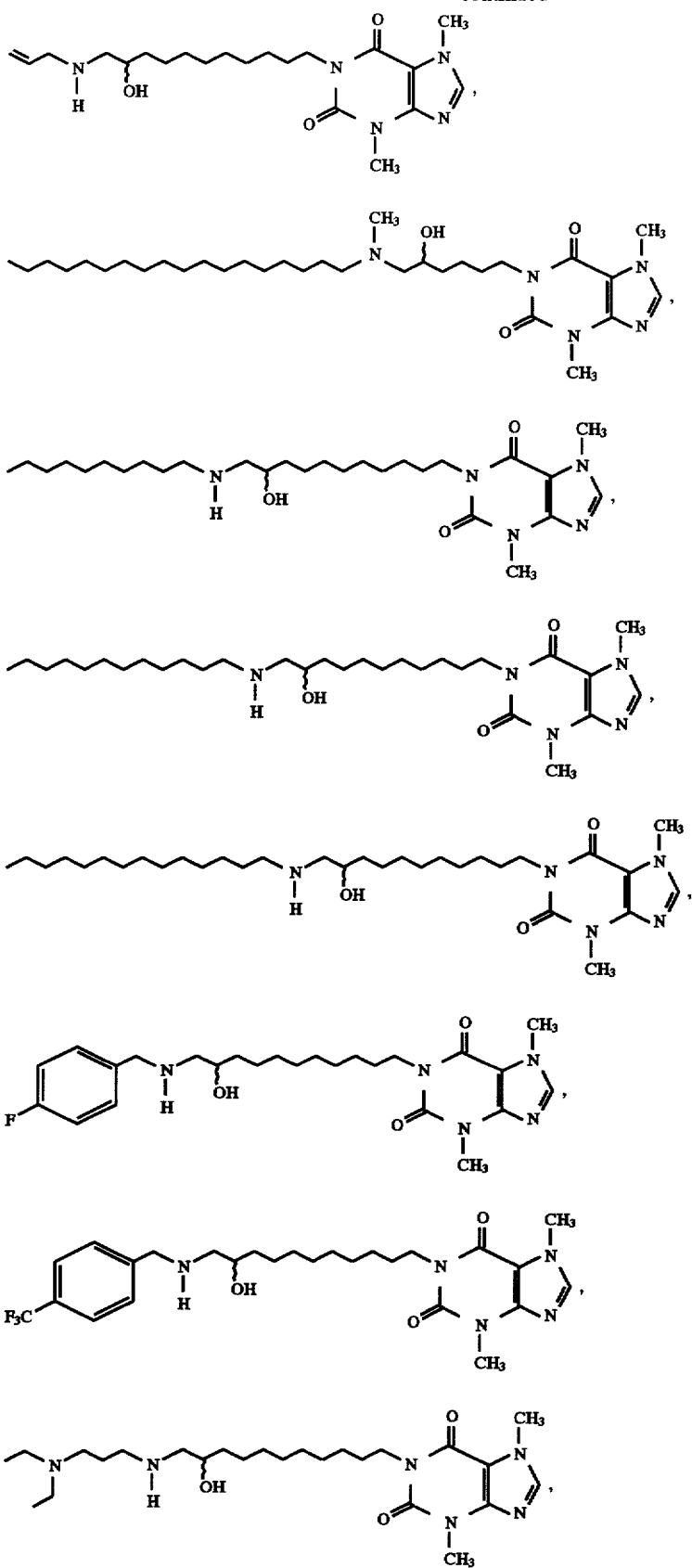

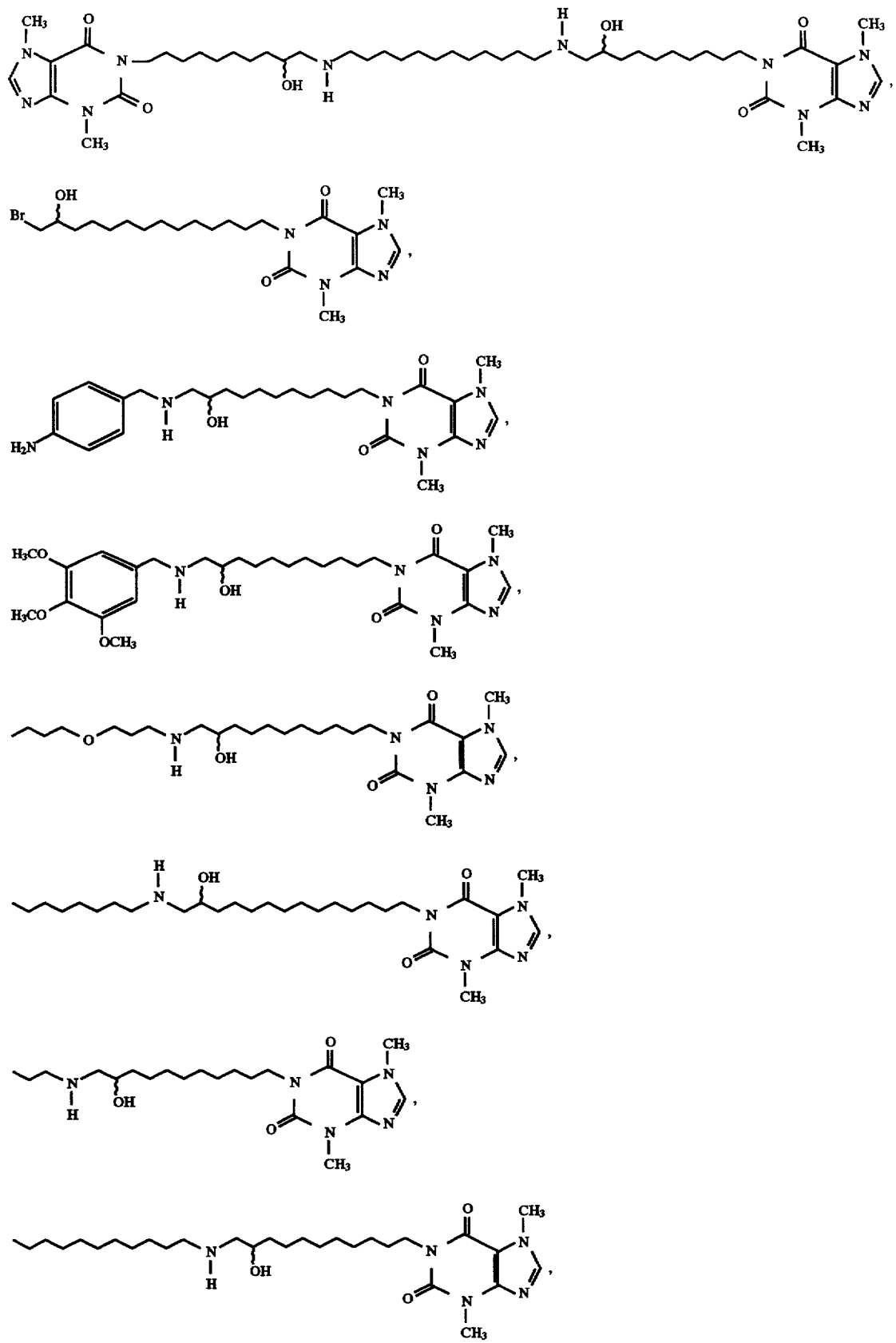

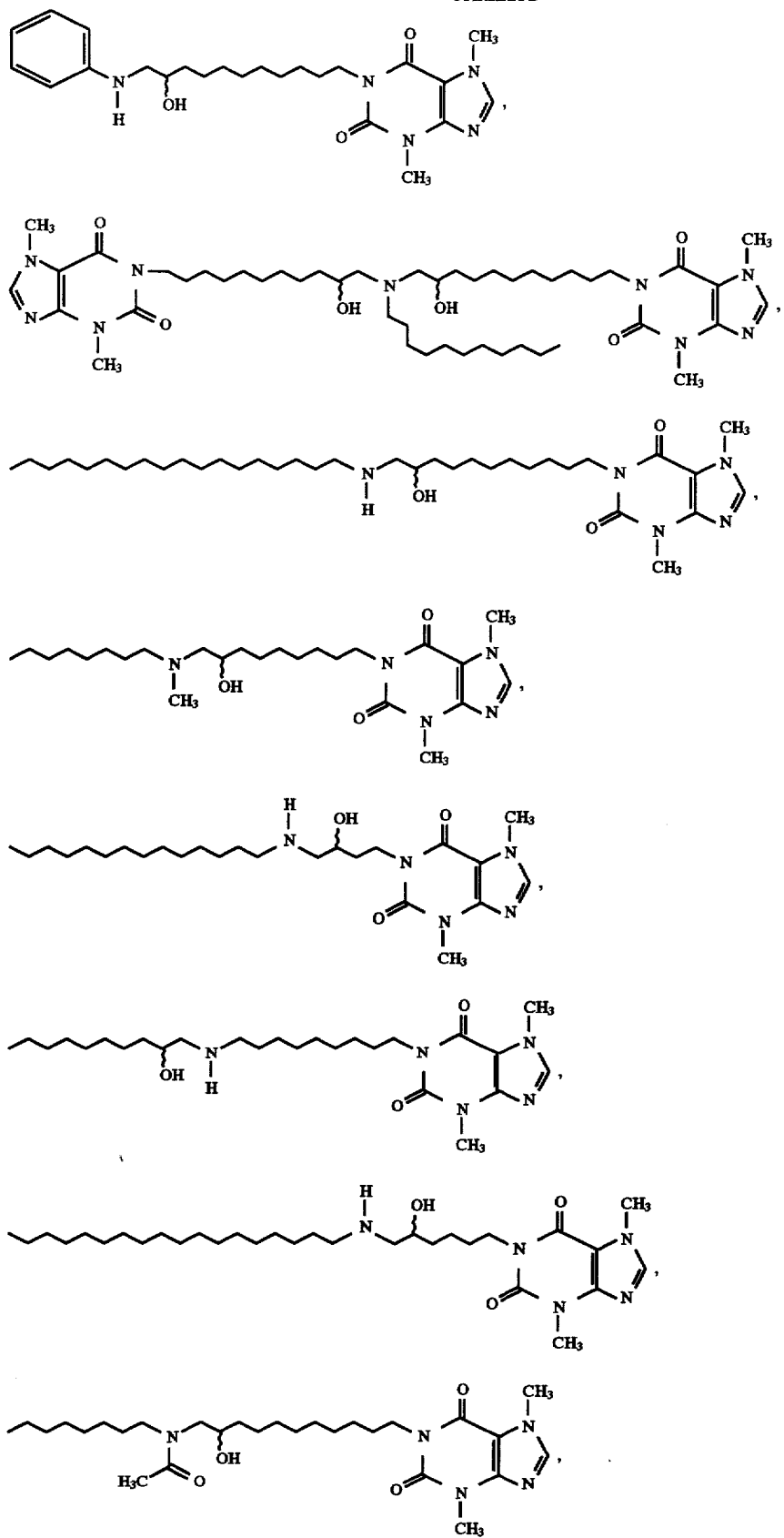

-continued

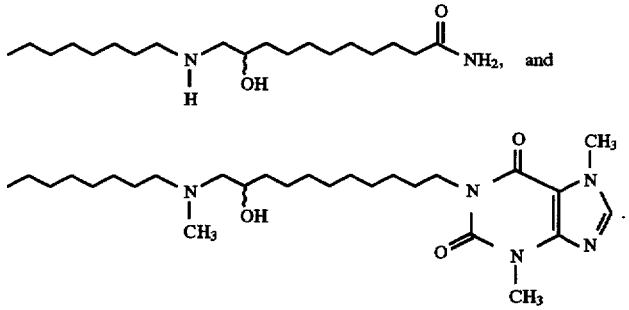

31. A method for treating symptoms of an acute or chronic inflammatory disease selected from the group consisting of: alcoholic hepatitis, allergies due to degranulation of mast cells and basophils, asthma, atherosclerosis, coronary artery disease, glomerula nephritis, inflammatory bowel disease, lung hypoxia, multiple sclerosis, organ or hematopoietic injury in response to cytotoxic therapy, osteoarthritis, osteoporosis, peridontal disease, rheumatoid arthritis, septic shock, sepsis syndrome, scleroderma and stroke, the method comprising the step of administering an effective amount of a compound to an individual having symptoms of the acute or chronic inflammatory disease whereby a cellular response mediated by a second messenger is affected, the compound having a formula:

$(X)_j$—CORE MOIETY wherein:
j is an integer from one to three, the core moiety comprises a substituted or unsubstituted nitrogen-containing heterocycle having one ring or two fused rings, each ring having five to six ring atoms and X is a racemic mixture, R or S enantiomer, solvate, hydrate, or salt of:

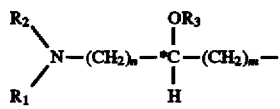

wherein:
*C is a chiral carbon atom; n is an integer from one to four;
one or more carbon atoms of $(CH_2)_n$ may be substituted by a carbonyl or hydroxyl group;
m is an integer from four to fourteen;
independently, $R_1$ and $R_2$ are hydrogen, a straight or branched chain alkyl or alkenyl group of up to twelve carbon atoms in length, or —$(CH_2)_w R_5$, w being an integer from two to fourteen and $R_5$ being a mono-, di- or tri-substituted or unsubstituted aryl group, substituents on $R_5$ being selected from the group consisting of hydroxyl, chloro, fluoro, bromo, or $C_{1-6}$ alkoxyl or a substituted or unsubstituted, saturated or unsaturated heterocyclic group having from four to seven carbon atoms; or
$R_1$ and $R_2$ jointly form a substituted or unsubstituted, saturated or unsaturated heterocyclic group having from four to seven carbon atoms, N being a hetero atom; and
$R_3$ is hydrogen or $C_{1-3}$; or
jointly one of $R_1$ or $R_2$ and $R_3$ form a substituted or unsubstituted linking carbon chain, having from one to four carbon atoms, joining the O and N in a cyclic structure, an integer sum equal to n+a number of carbon atoms in the linking carbon chain being less than six; and
wherein a ring atom of the core moiety is attached to a terminal carbon atom of $(CH_2)_m$.

32. The method of claim 31, wherein n is an integer from one to three.

33. The method of claim 31, wherein m is an integer from seven to fourteen.

34. The method of claim 31, wherein m is an integer from ten to fourteen.

35. The method of claim 31, wherein the ring atom of the core moiety is a nitrogen atom.

36. The method of claim 31, wherein the core moiety is a member selected from the group consisting of substituted or unsubstituted: barbituric acid; benzamido; flutarimidyl; glutarimidyl; homophthalimidyl; imidazolylamido; isocarbostyrilyl; lumazinyl; pteridinyl; pthalimidyl; piperidinyl; pyridinyl; pyrimidinyl; pyrrolylamido; quinazolinedionyl; quinazolinonyl; quinolonyl; succinimidyl; theobrominyl; thyminyl; triazinyl; uracil and xanthinyl.

37. The method of claim 31, wherein the core moiety is selected from the group consisting of glutarimidyl, methylthyminyl, methyluracil, thyminyl, theobrominyl, uracil and xanthinyl.

38. The method of claim 37, wherein the core moiety is xanthinyl, the terminal carbon atom of $(CH_2)_n$ is attached to the $N_1$ xanthinyl nitrogen and $N_3$ and $N_7$ xanthinyl nitrogens are independently substituted by a member selected from the group consisting of hydrogen, methyl, fluoro, chloro and amino.

39. The method of claim 37, wherein the core moiety is glutarimidyl.

40. The method of claim 37, wherein the core moiety is uracil and the terminal carbon atom of $(CH_2)_n$ is attached to a uracil nitrogen atom.

41. The method of claim 37, wherein the core moiety is methylthyminyl or thyminyl and the terminal carbon atom of $(CH_2)_n$ is attached to a nitrogen atom.

42. The method of claim 31, wherein the core moiety is selected from the group consisting of 1-methyllumazinyl; methylbarbituric acid; 3,3-dimethylflutarimidyl; 2-hydroxypyridinyl; methyldihydroxypyrazolopyrimidinyl; methylpyrrolopyrimidinyl; 2-pyrrolylamido; 3-pyrrolylamido; 1,2,3,4-tetrahydroisoquinolonyl; 1-methyl-2,4(1H,3H)-quinazolinedionyl; quinazolin-4(3H)-onyl; alkyl-substituted $(C_{1-6})$ thyminyl; methylthyminyl; alkyl-substituted $(C_{1-6})$ uracil; 6-aminouracil; 1-methyl-5,6-dihydrouracil; 1-methyluracil; 5- and/or 6-position substituted uracils; 1,7-dimethylxanthinyl; 3,7-dimethylxanthinyl; 3-methylxanthinyl; 3-methyl-7-methylpivaloylxanthinyl; 8-amino-3-methylxanthinyl; and 7-methylhypoxanthinyl.

43. The method of claim 42, wherein the methyldihydroxypyrazolopyrimidinyl is 1,3-dimethyldihydroxypyrazolo[4,3-d]pyrimidinyl.
44. The method of claim 42, wherein the methylpyrrolopyrimidinyl is 1-methylpyrrolo[2,3-d]pyrimidinyl.
45. The method of claim 31, wherein the compound has a formula selected from the group consisting of:
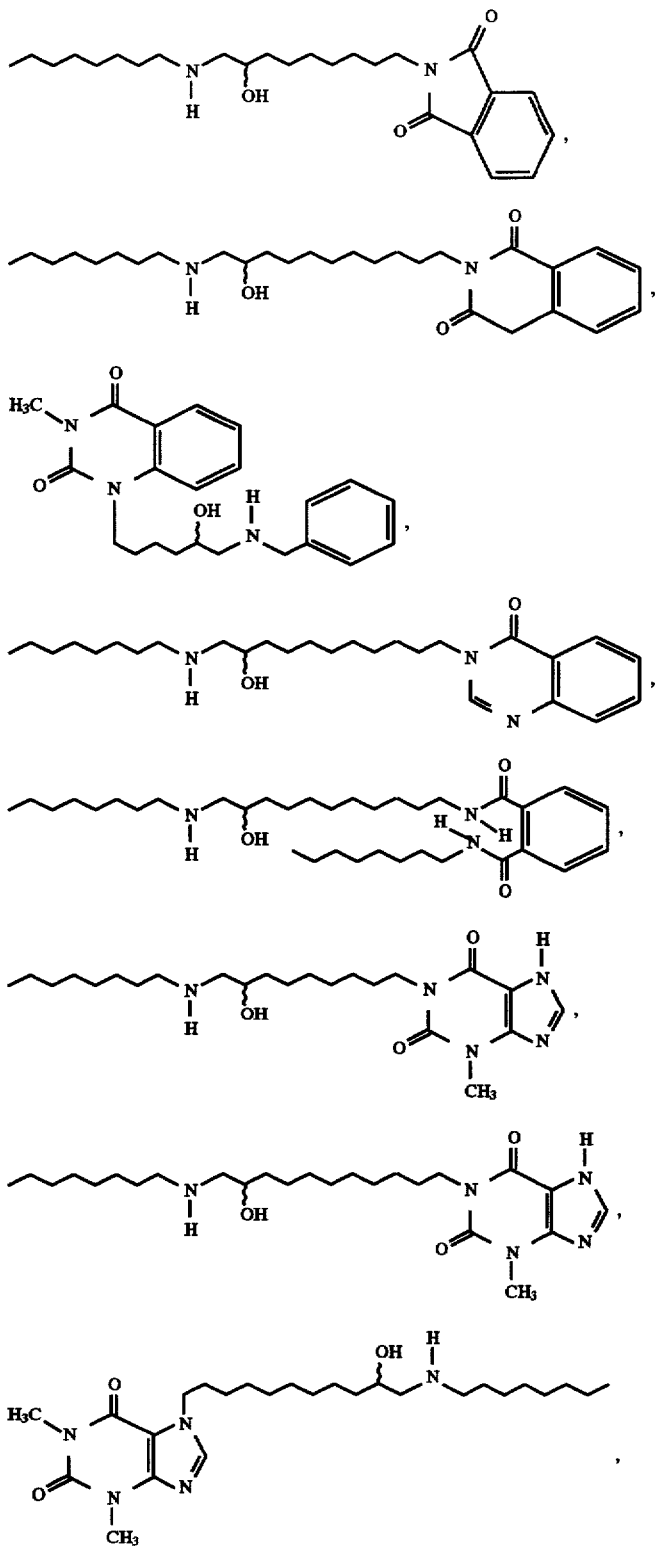

-continued
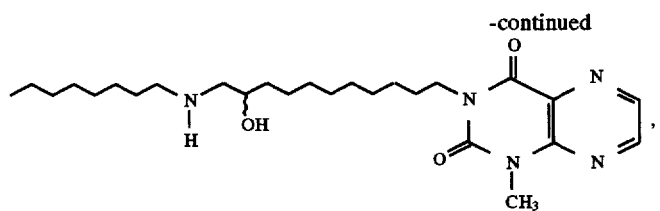
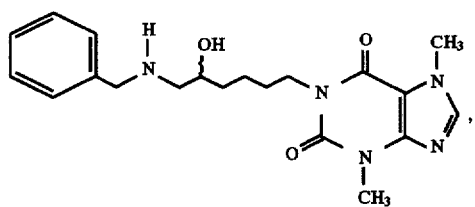
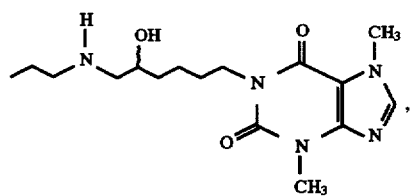
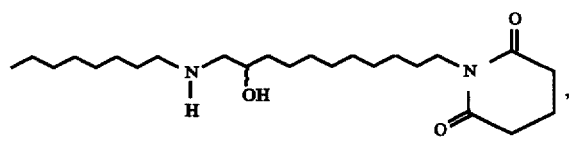
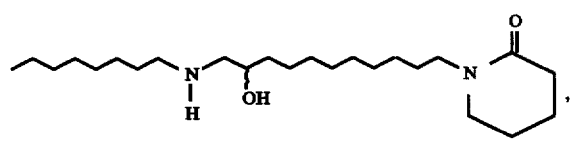
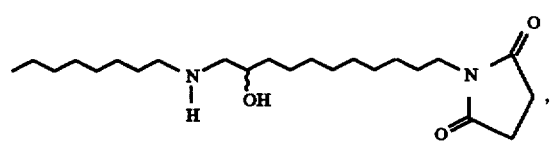
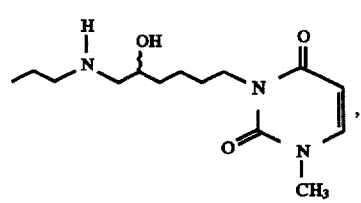
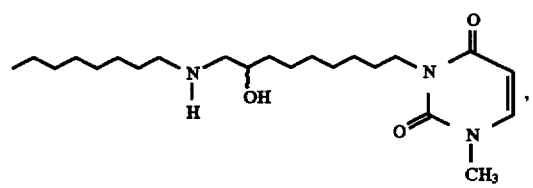
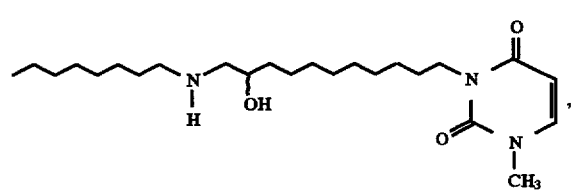

-continued
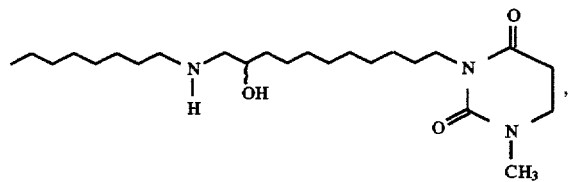,
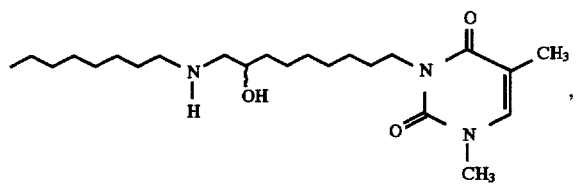,
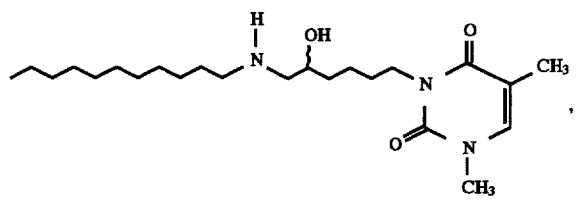,
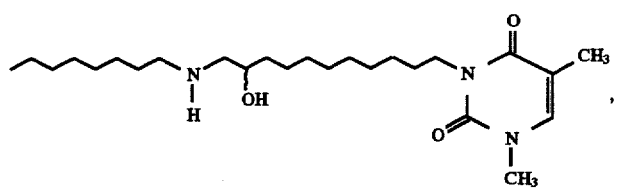,
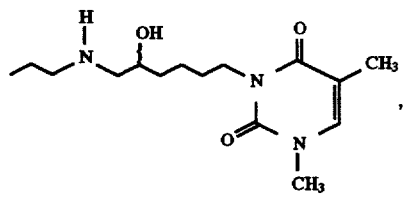,
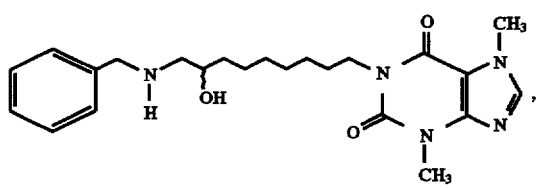,
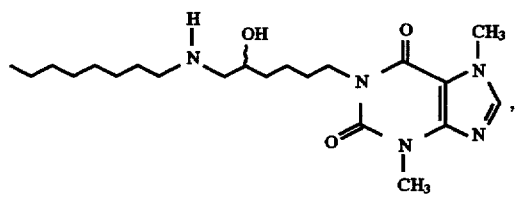,
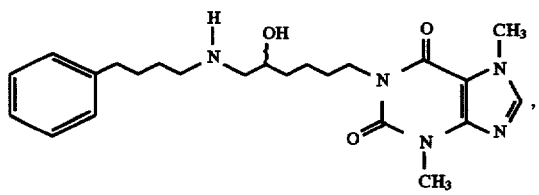, -continued
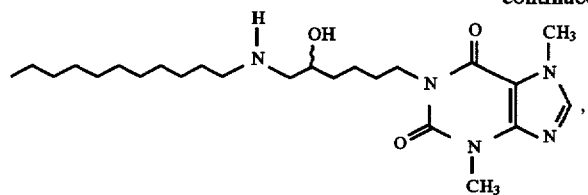
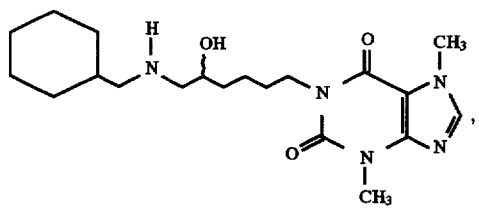
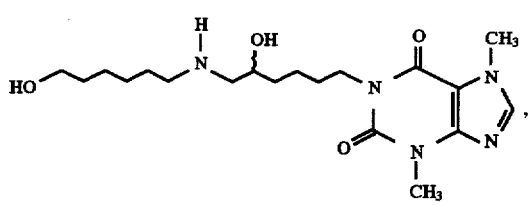
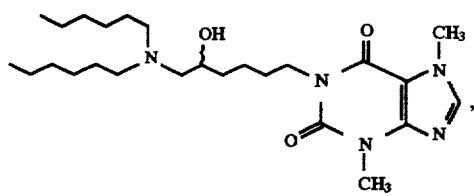
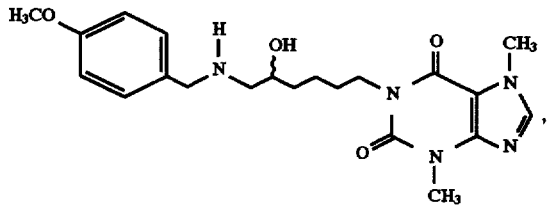
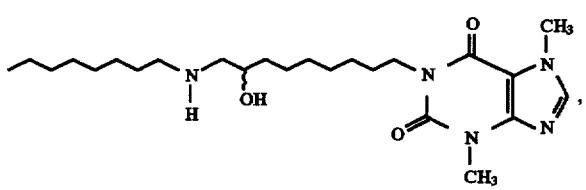
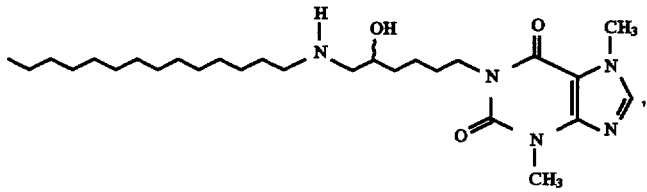
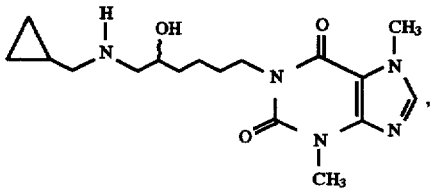

-continued
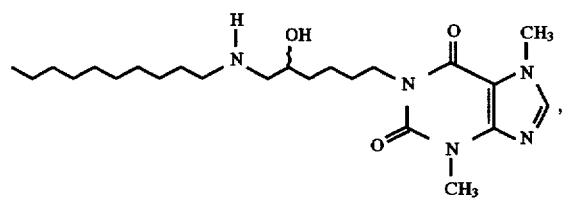
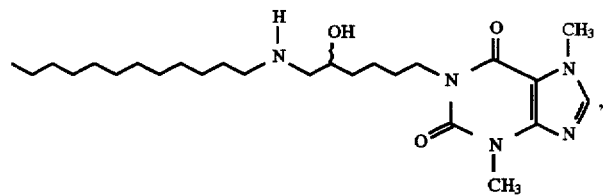
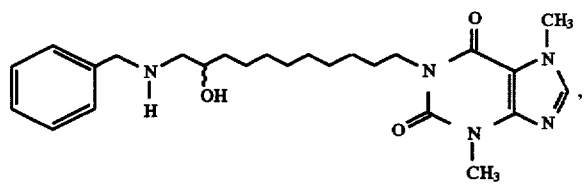
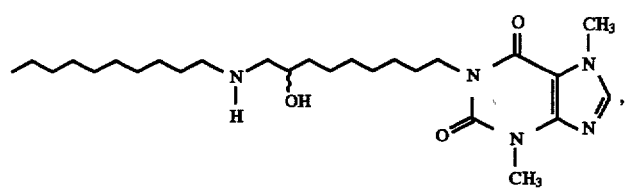
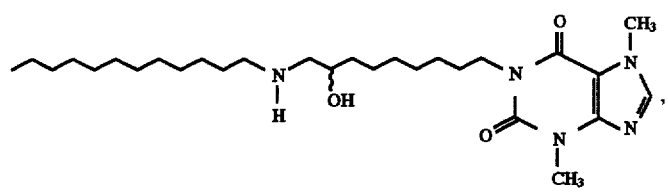
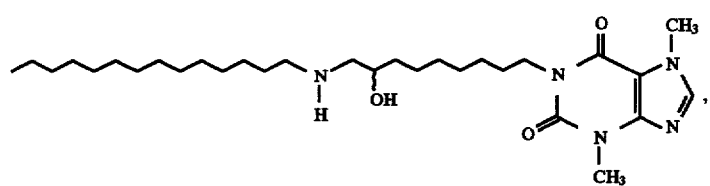
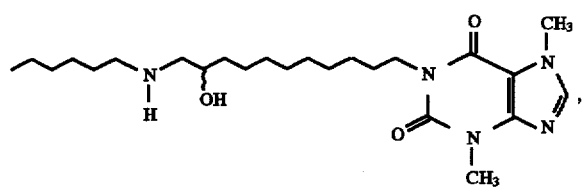
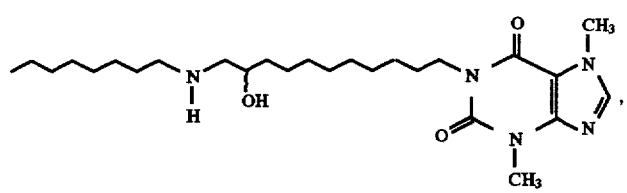

-continued
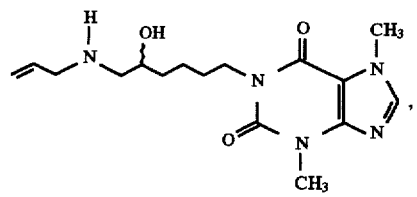
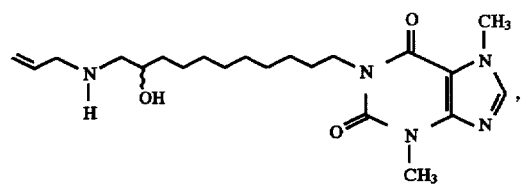
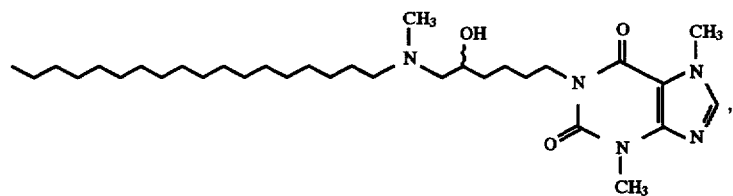
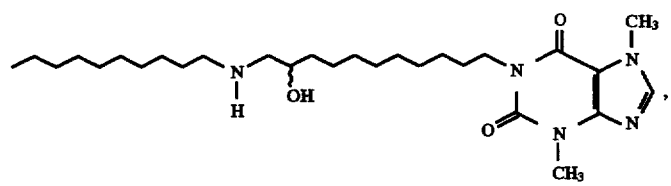
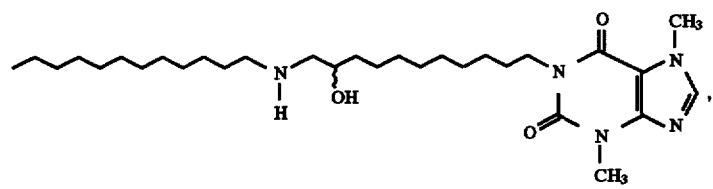
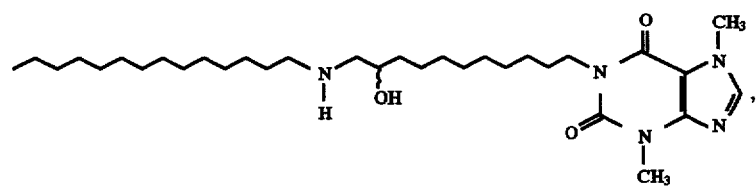
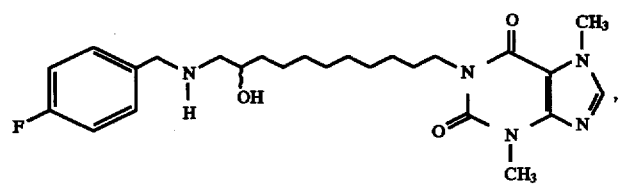
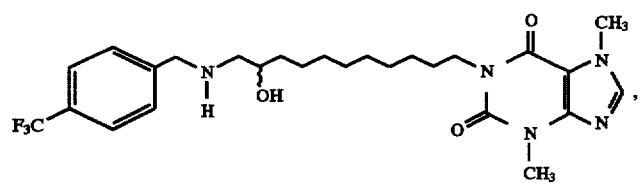

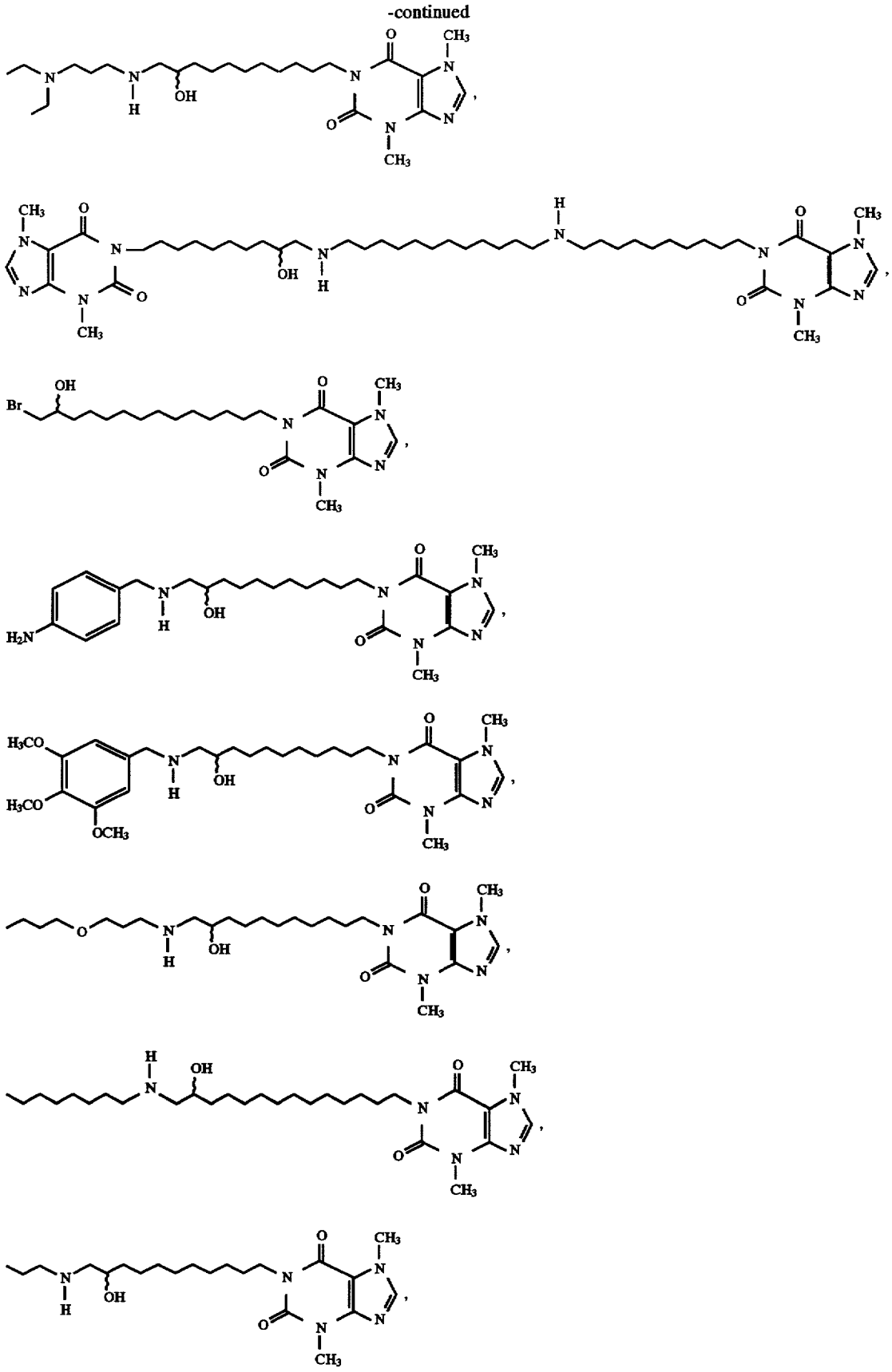

-continued
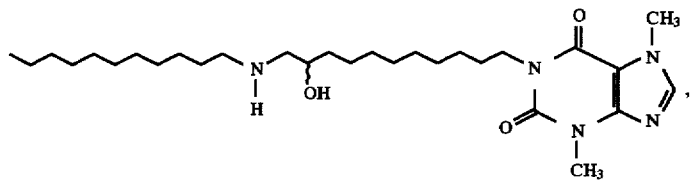
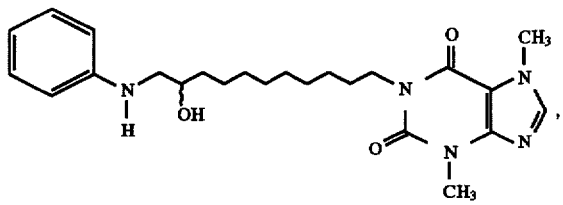
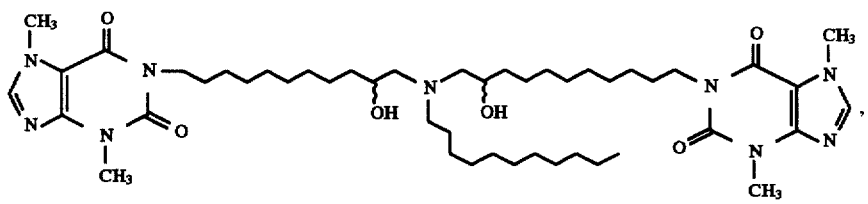
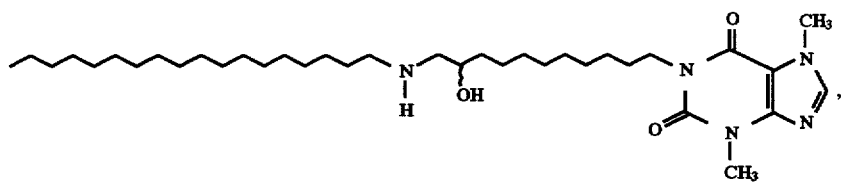
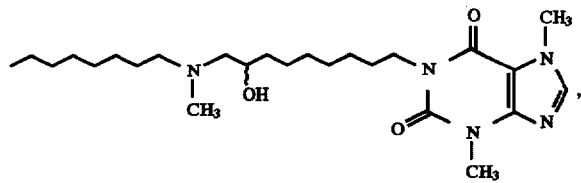
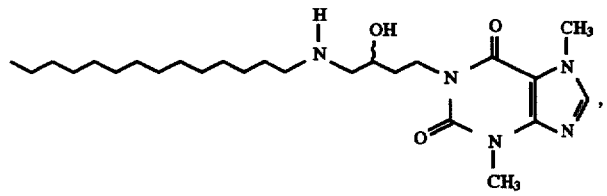
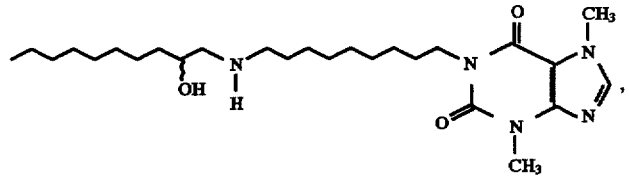
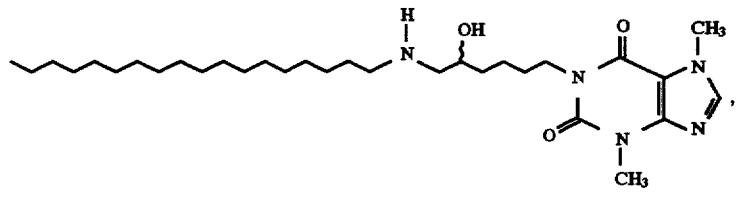

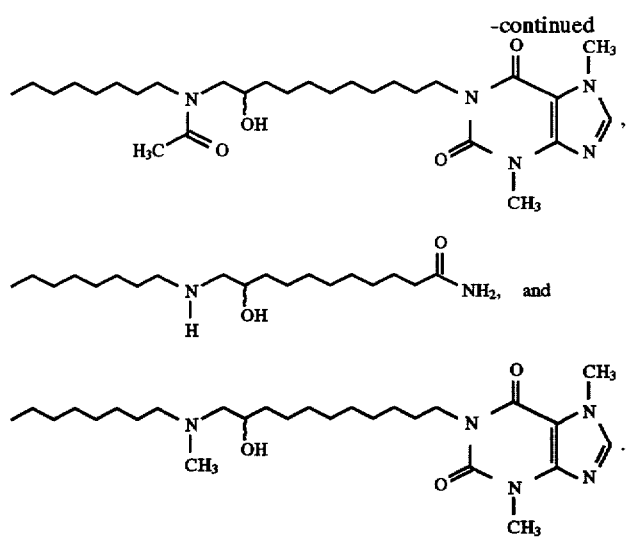
* * * * *